(12) United States Patent
Masuda

(10) Patent No.: US 8,236,017 B2
(45) Date of Patent: Aug. 7, 2012

(54) ULTRASONIC THERAPEUTIC APPARATUS

(75) Inventor: Shinya Masuda, Hino (JP)

(73) Assignee: Olympus Medical Systems Corp. (JP)

( * ) Notice: Subject to any disclaimer, the term of this patent is extended or adjusted under 35 U.S.C. 154(b) by 1167 days.

(21) Appl. No.: 12/057,586

(22) Filed: Mar. 28, 2008

(65) Prior Publication Data

US 2009/0088668 A1    Apr. 2, 2009

Related U.S. Application Data

(63) Continuation-in-part of application No. 11/862,562, filed on Sep. 27, 2007, now abandoned.

(51) Int. Cl.
*A61B 17/32* (2006.01)
*A61B 18/18* (2006.01)

(52) U.S. Cl. .......................................... 606/169; 600/37

(58) Field of Classification Search .................... 606/40, 606/46, 47, 49–52, 169
See application file for complete search history.

(56) References Cited

U.S. PATENT DOCUMENTS 6,193,709 B1 * 2/2001 Miyawaki et al. ............... 606/1
2005/0101965 A1 * 5/2005 Ryan ............................. 606/96

FOREIGN PATENT DOCUMENTS

| EP | 0 908 151 | 4/1999 |
| JP | 2000-254138 | 9/2000 |
| JP | 2005-278932 | 10/2005 |

* cited by examiner

*Primary Examiner* — Tuan V Nguyen
(74) *Attorney, Agent, or Firm* — Ostrolenk Faber LLP

(57) ABSTRACT

A surgical operating apparatus includes rod-shaped probe main body which is inserted into a sheath and has a distal end and which is configured to transmit ultrasonic vibration, a jaw pivoted to a distal end of the sheath, a probe distal end which is provided at the distal end of the probe main body and a driving member including a tubular main body portion configured to be inserted into the sheath slidably along an axial direction of the sheath and an acting portion which is provided at a distal end of the main body portion and has a connection portion connected to the jaw, the connection portion positioned. The sheath includes a notched portion positioned and configured to prevent the sheath from contacting the proximal portion of the jaw.

3 Claims, 40 Drawing Sheets

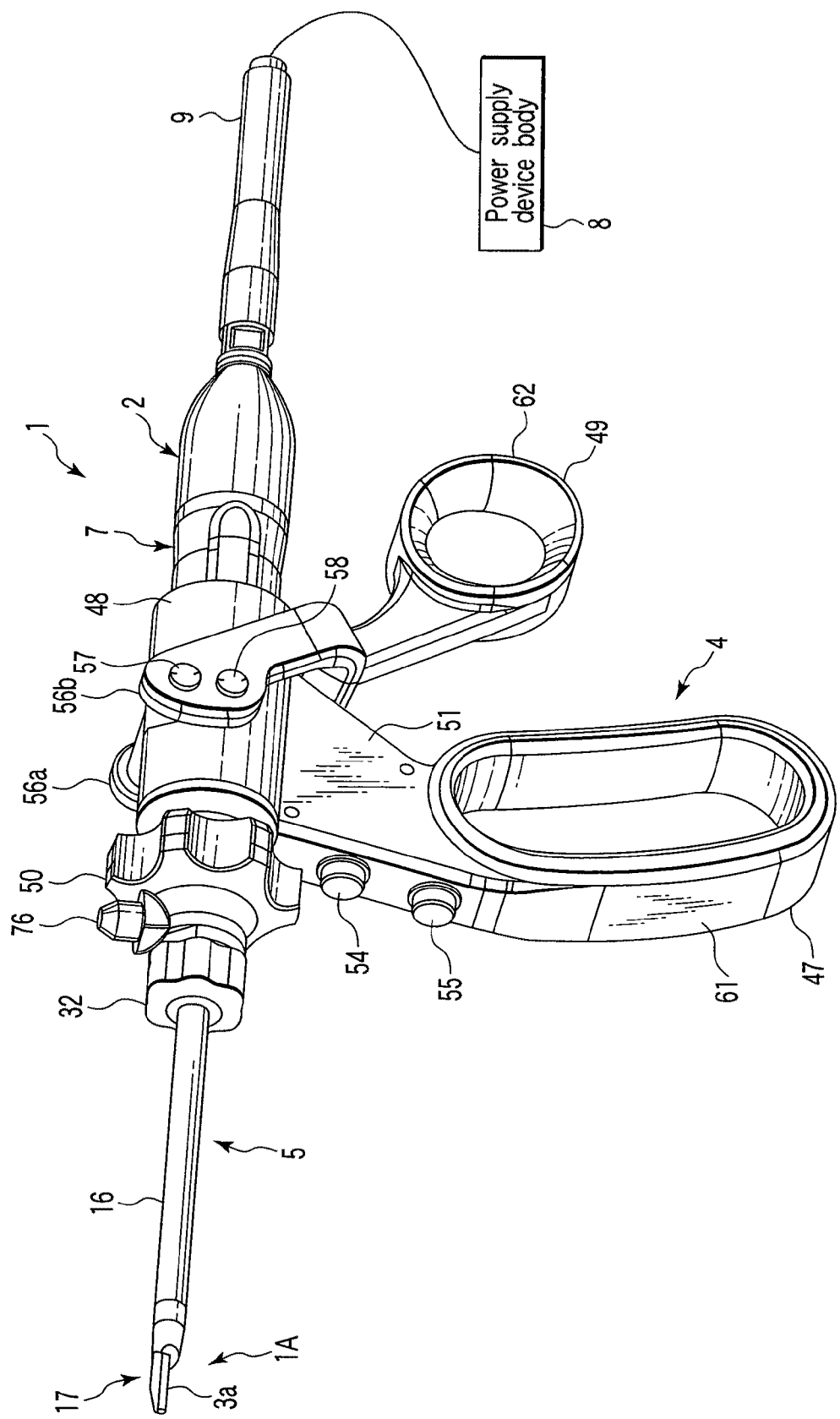
F I G. 1

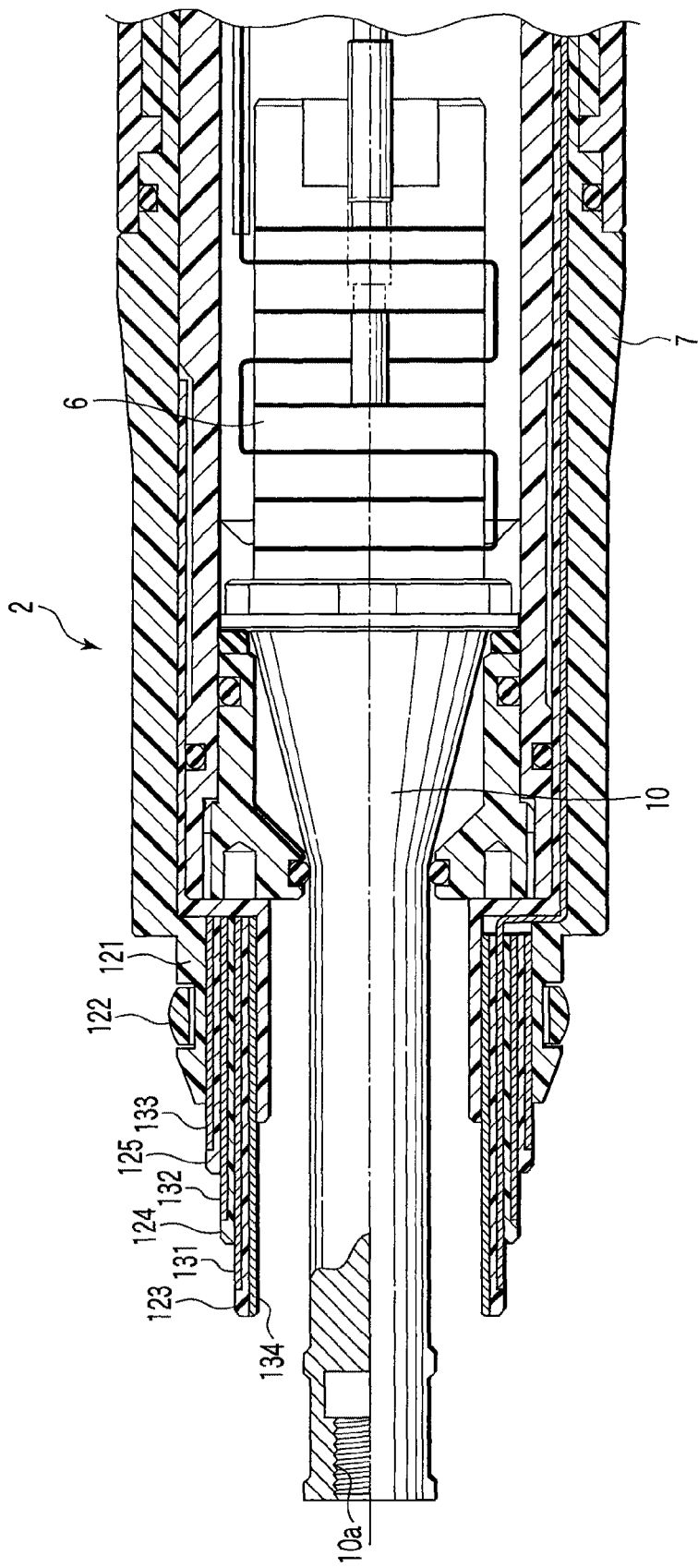
F I G. 4

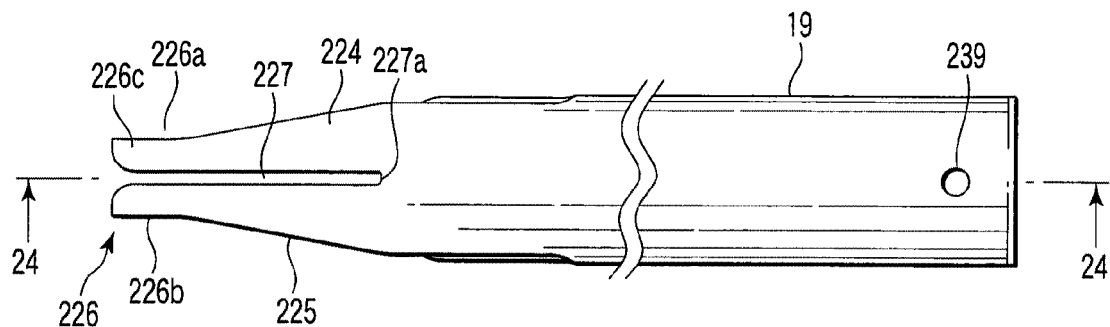
F I G. 23
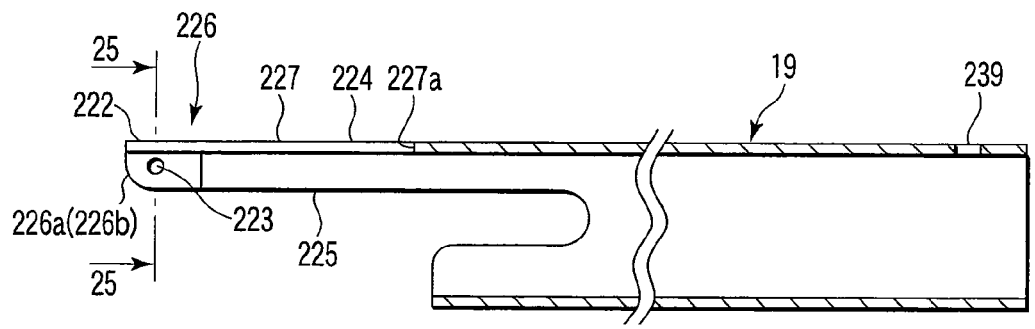
F I G. 24
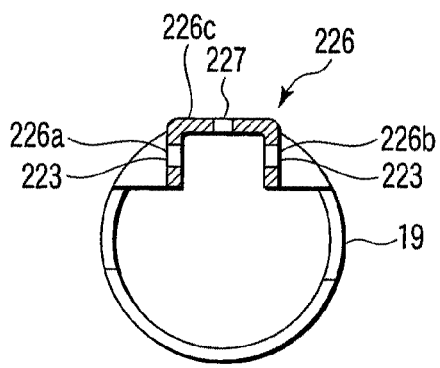
F I G. 25

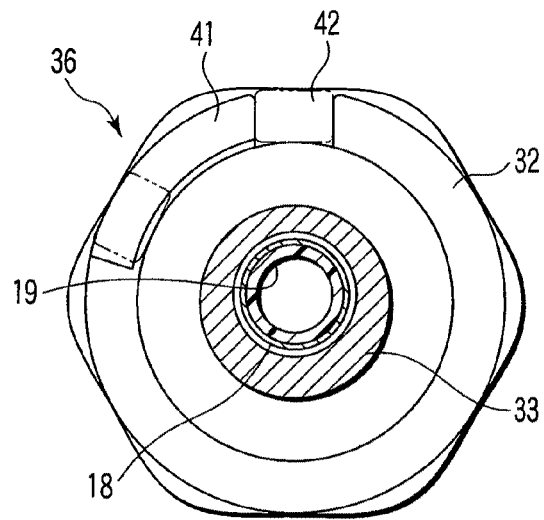
F I G. 33
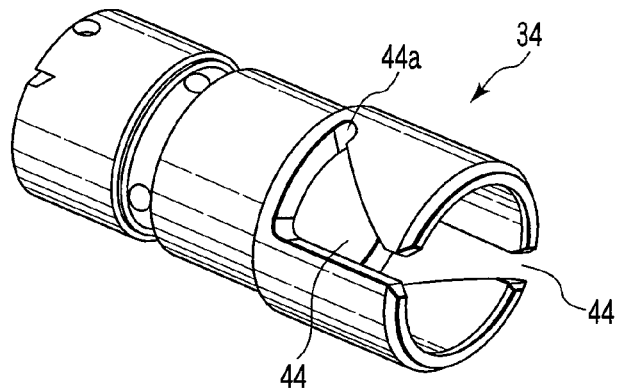
F I G. 34
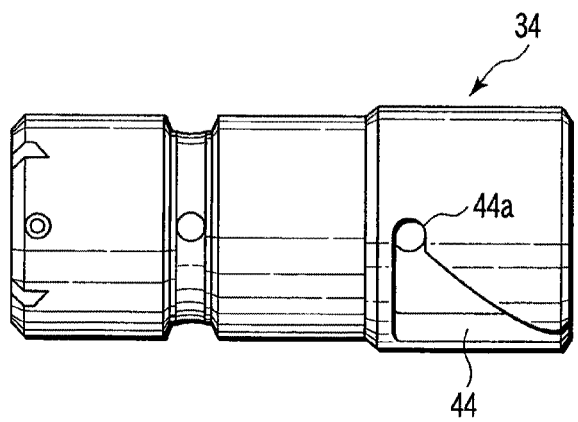
F I G. 35

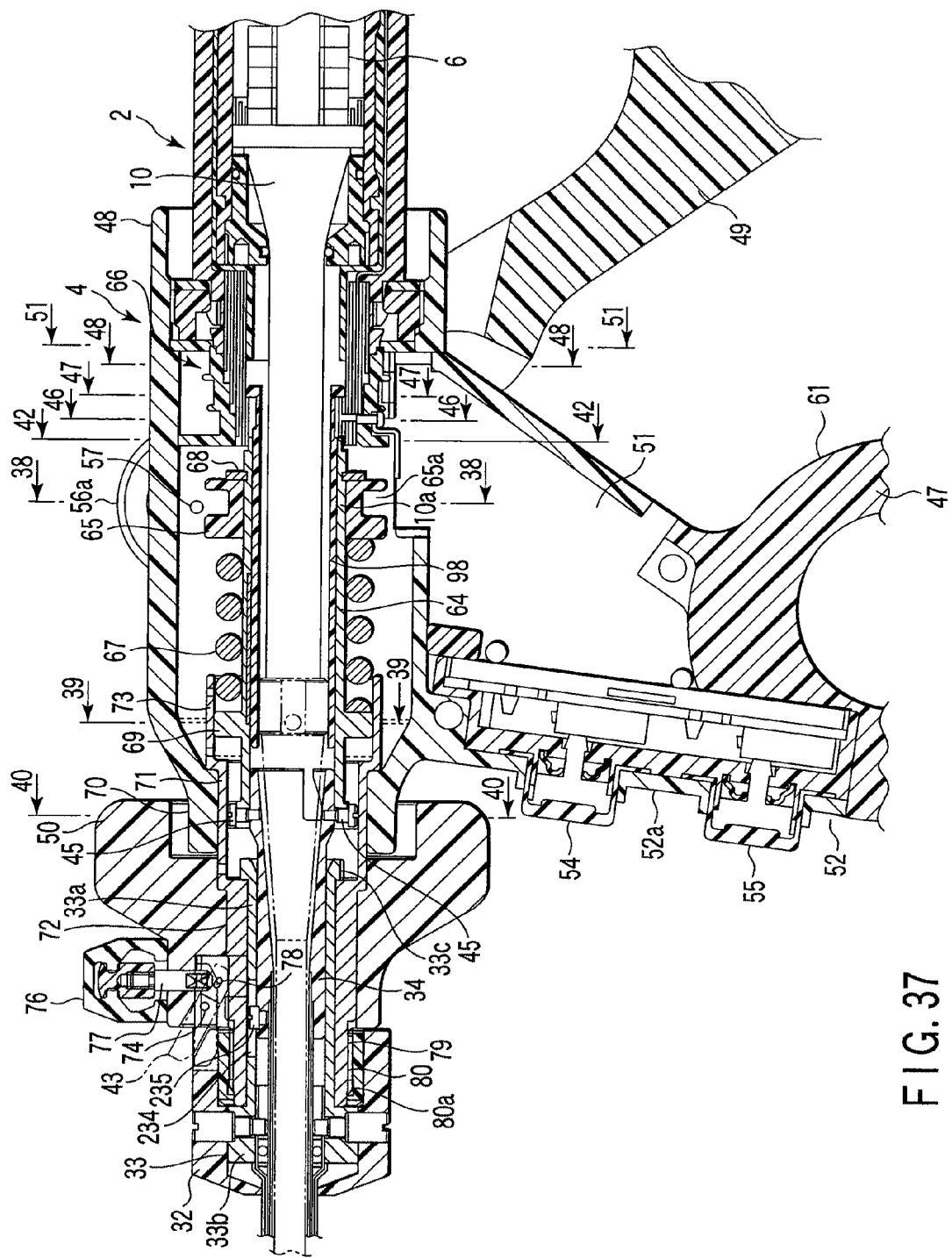
F I G. 37

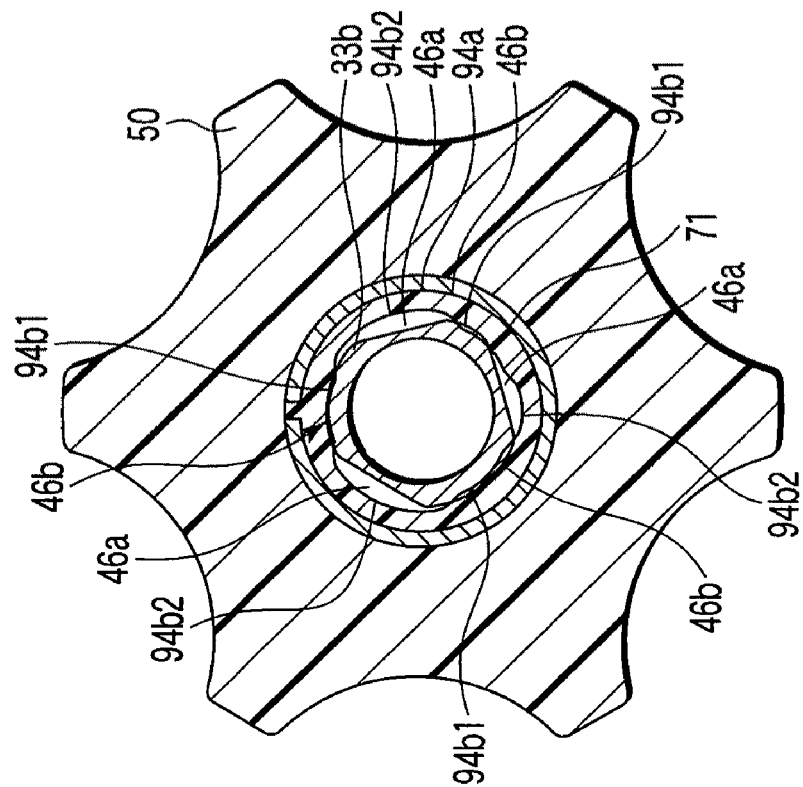
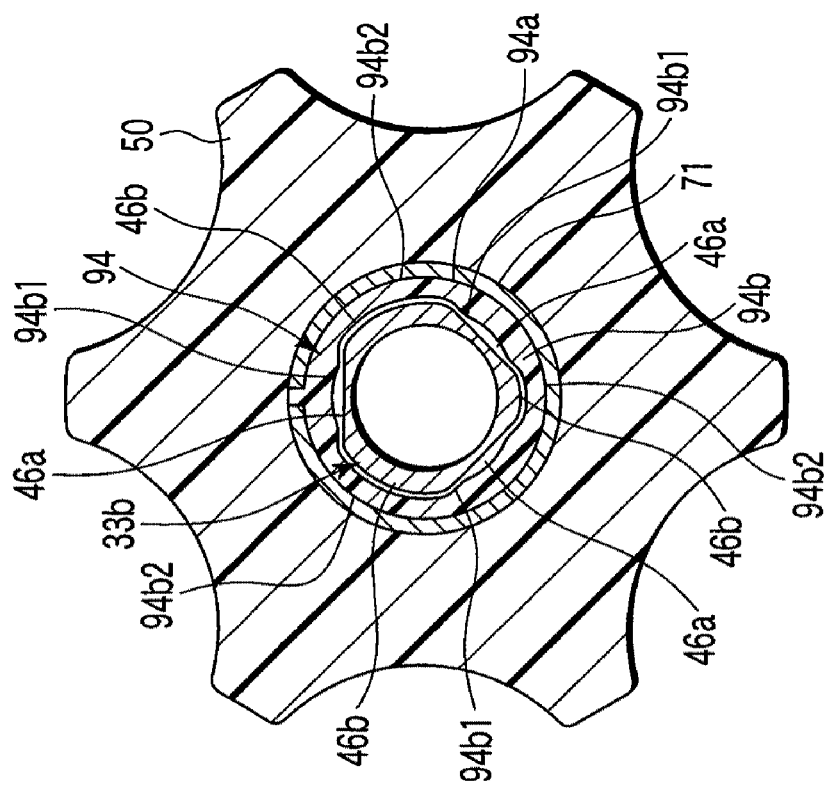
FIG. 41B
FIG. 41A

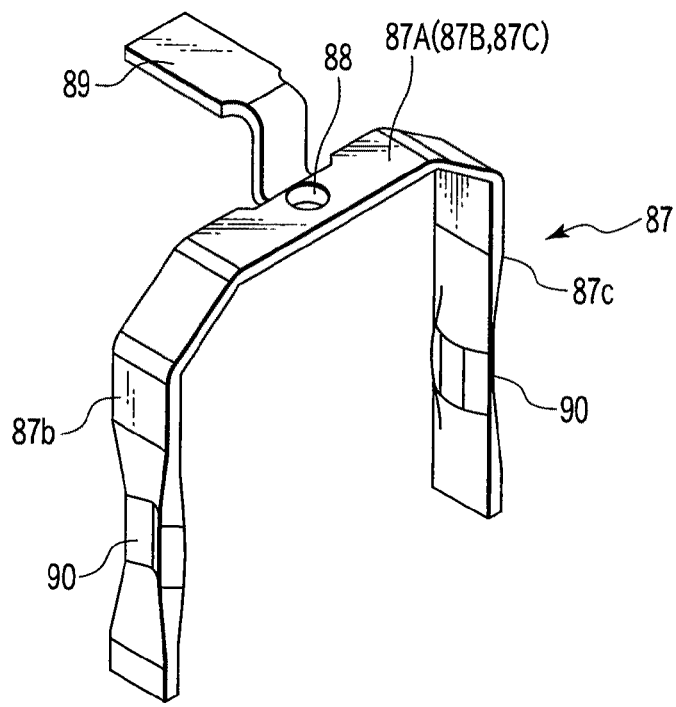
F I G. 49
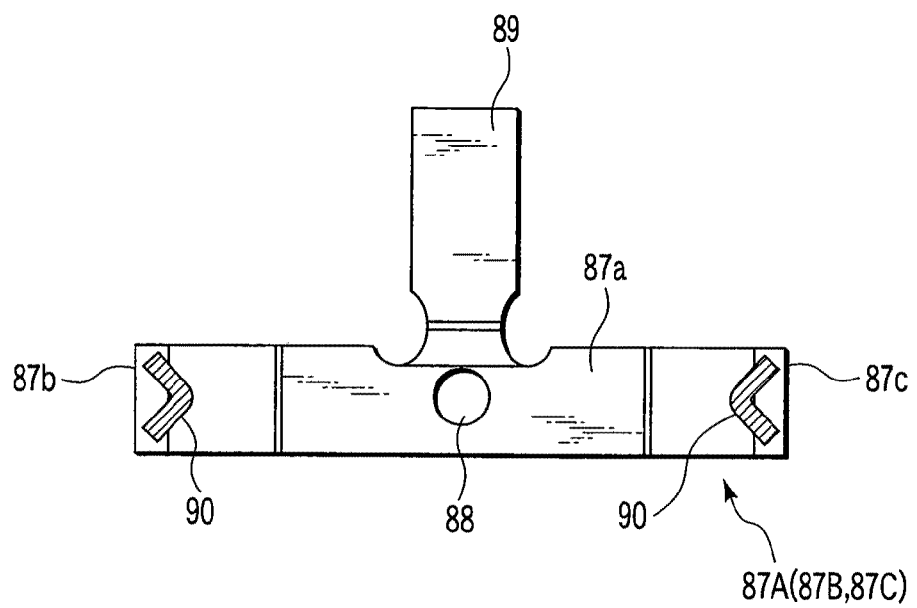
F I G. 50

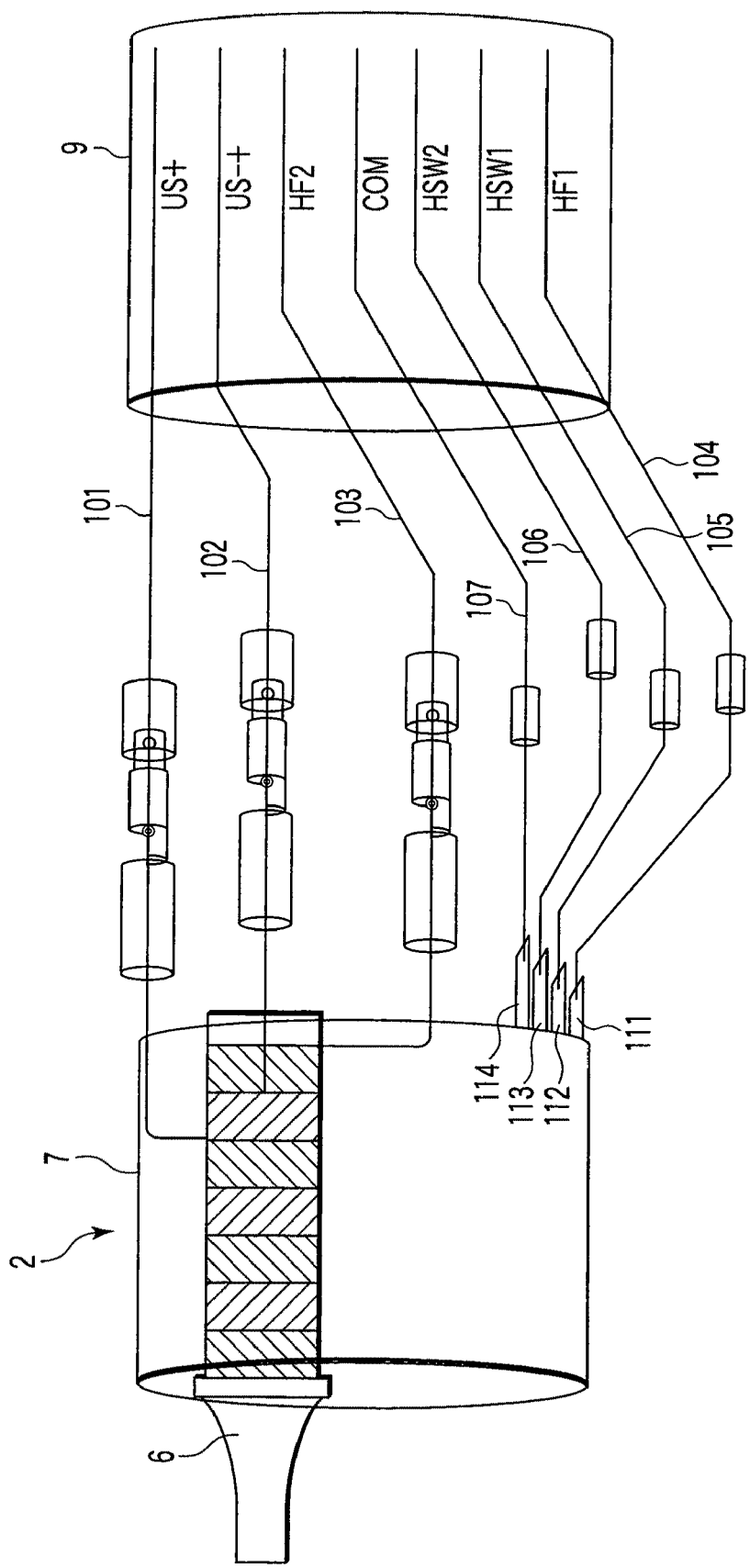
F I G. 52

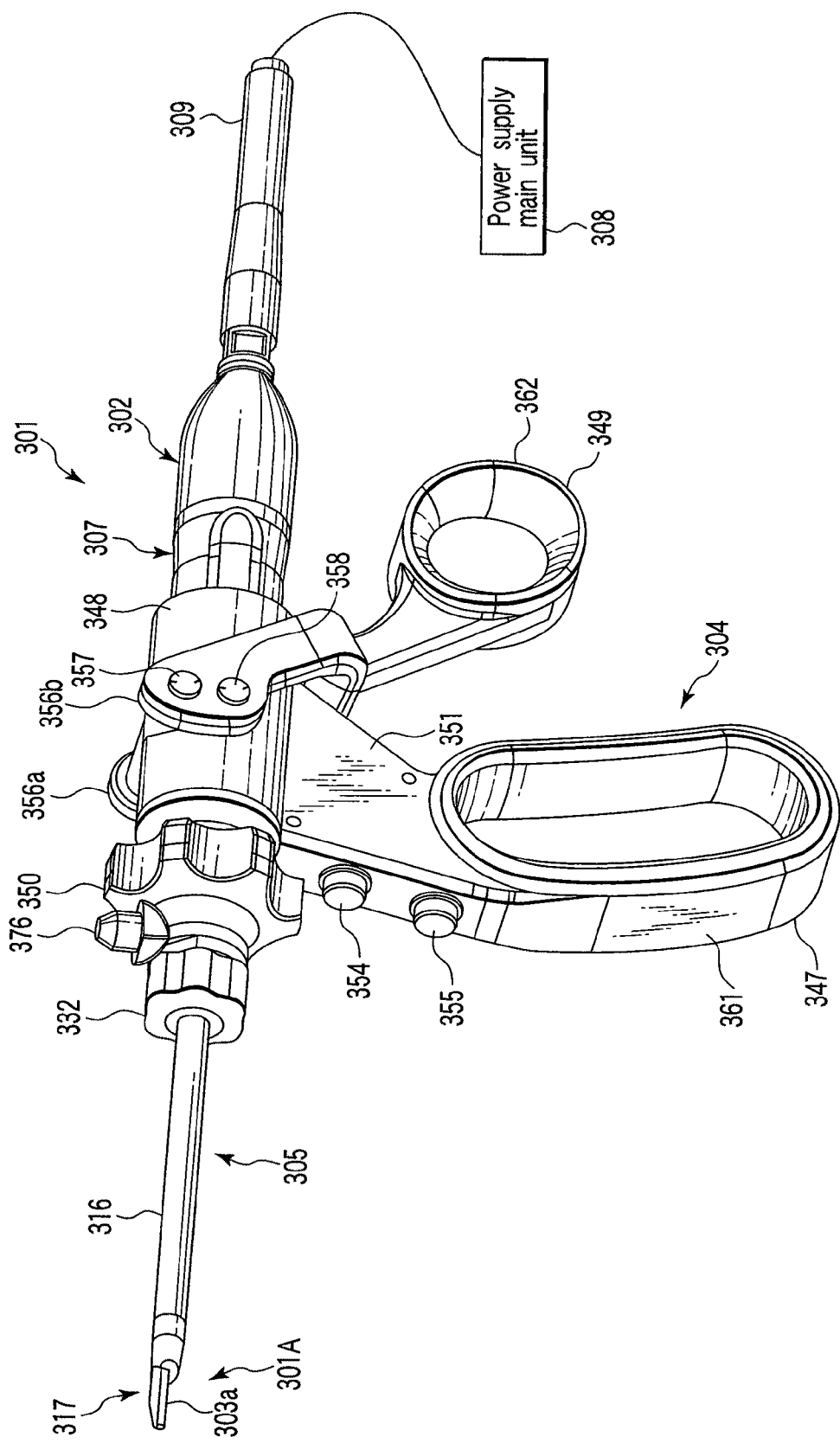
F I G. 53

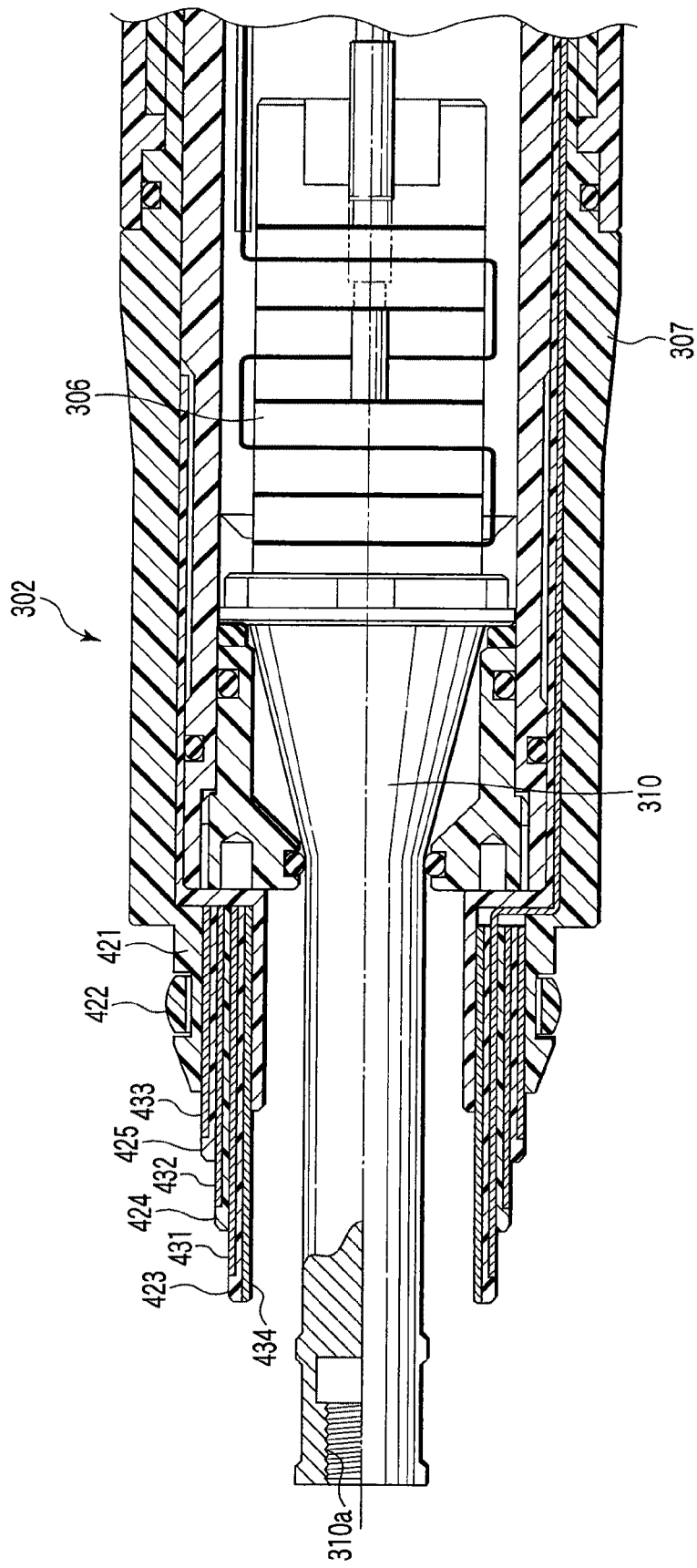
F I G. 56

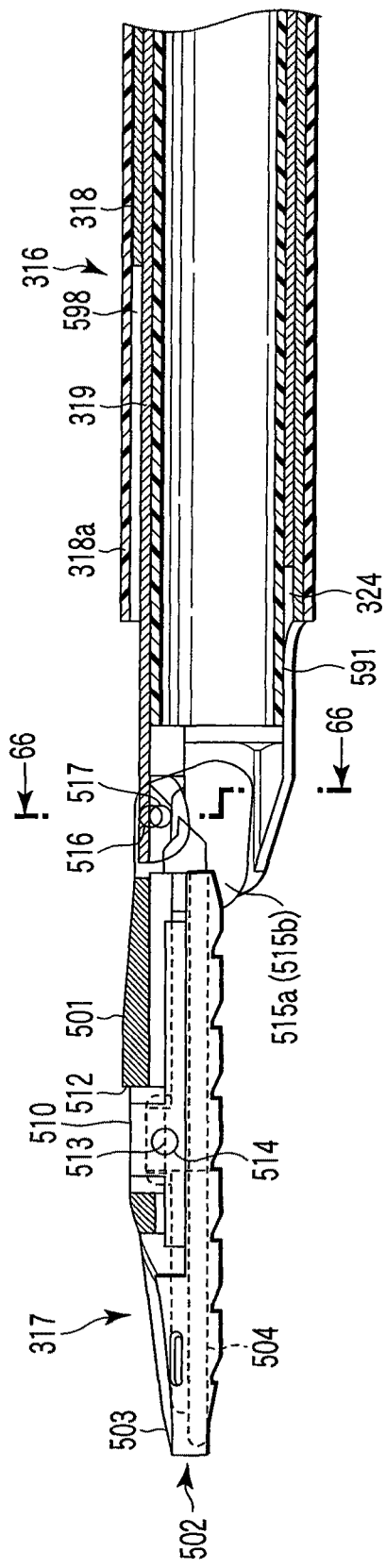
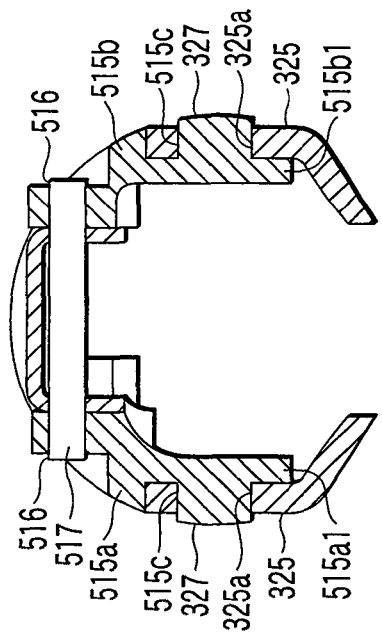
F I G. 65
F I G. 66

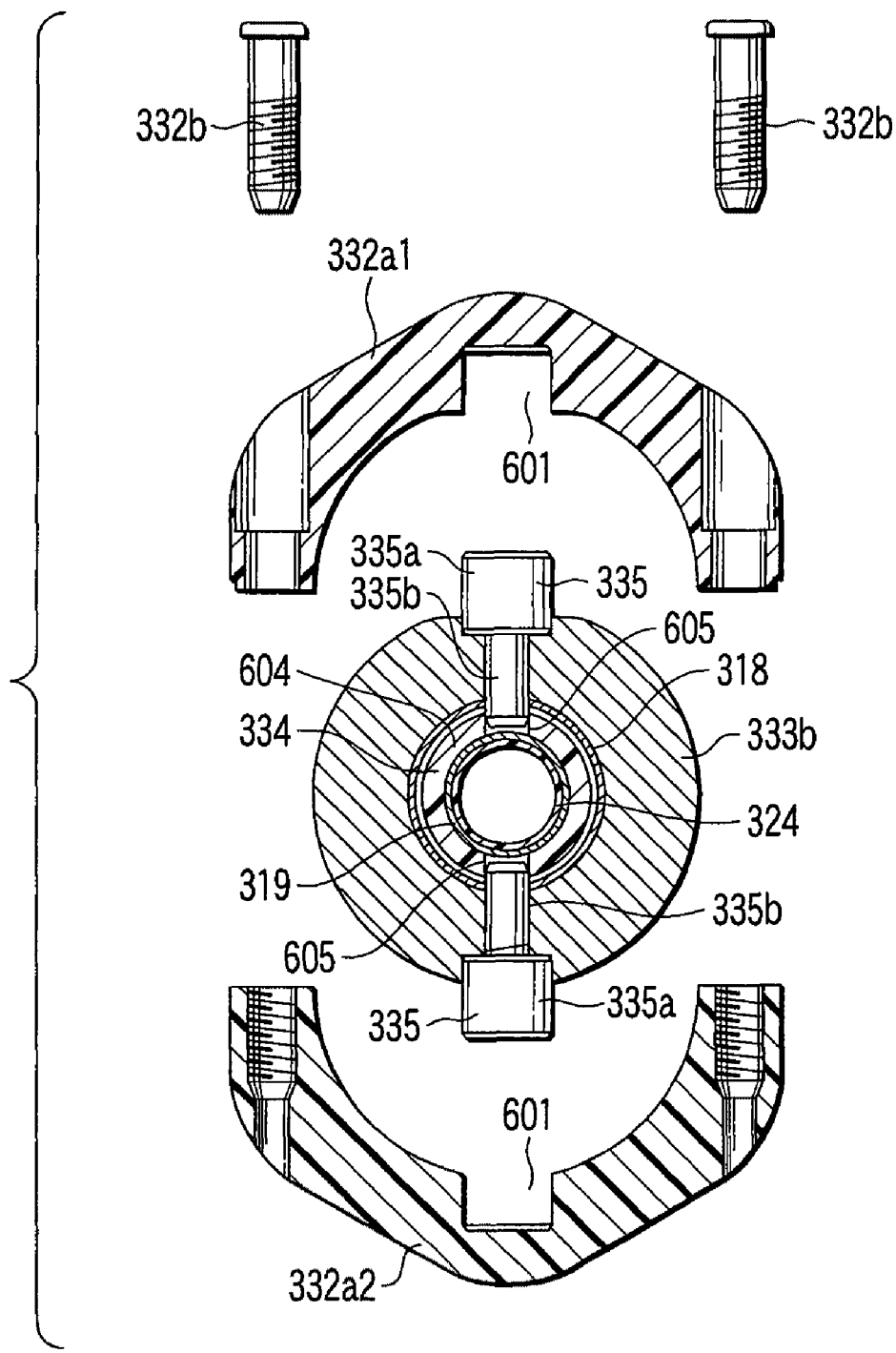
F I G. 73

ULTRASONIC THERAPEUTIC APPARATUS

CROSS-REFERENCE TO RELATED APLICATIONS

This application is a continuation-in-part of U.S. patent application Ser. No. 11/862,562, filed on Sep. 27, 2007, abandoned.

BACKGROUND OF THE INVENTION

The present invention relates to a surgical operating apparatus which performs therapeutic treatment, such as incision, resection or coagulation, of a living body tissue by making use of composite energy of ultrasonic and high-frequency waves, and which can also perform therapeutic treatment by high-frequency waves.

Jpn. Pat. Appln. KOKAI Publication No. 2005-278932 (Patent Document 1), for instance, discloses an ultrasonic therapeutic apparatus as a general example of an ultrasonic therapeutic apparatus which can perform therapeutic treatment, such as incision, resection or coagulation, of a living body tissue by making use of ultrasonic and can also perform therapeutic treatment by high-frequency waves.

In this apparatus, a proximal-side operation section is coupled to a proximal end portion of an elongated insertion section. An ultrasonic transducer which generates ultrasonic vibration is provided in the operation section. A therapeutic section for treating a living body tissue is provided at a distal end portion of the insertion section.

The insertion section has an elongated tubular sheath. A rod-shaped vibration transmission member (probe) is inserted in the sheath. A proximal end portion of the vibration transmission member is detachably attached to the ultrasonic transducer via a screw-type coupling section. Ultrasonic vibration, which is generated by the ultrasonic transducer, is transmitted to a probe distal end portion at the distal end side of the vibration transmission member.

In the therapeutic section, a jaw is provided so as to be opposed to the probe distal end portion. A proximal end portion of the jaw is rotatably supported on a distal end portion of the sheath via a support shaft. A driving pipe for driving the jaw is inserted in the sheath so as to be axially advancible/retreatable.

A pin receiving section is formed at a distal end portion of the driving pipe. The pin receiving section is formed in an extension portion which is extended, as one body with the driving pipe, to a distal end side from a distal end edge portion of the driving pipe. A coupling pin is provided at a distal end portion of the pin receiving section. The driving pipe and the jaw body are coupled by the coupling pin.

The operation section is provided with an operation handle. In accordance with the operation of the operation handle, the driving pipe is axially advanced/retreated. In interlock with the operation of the driving pipe, the jaw is opened/closed relative to the probe distal end portion.

At this time, a living body tissue is held between the probe distal end portion and the jaw in accordance with the closing operation of the jaw. In this state, ultrasonic vibration from the ultrasonic transducer is transmitted to the probe distal end portion on the therapeutic section side via the vibration transmission member. Thereby, using ultrasonic, therapeutic treatment, such as incision, resection or coagulation, of the living body tissue is performed.

In addition, in the apparatus of the above-described Patent Document 1, a proximal end portion of the sheath is detachably coupled to the operation handle of the operation section. Further, a high-frequency connection pin is attached to the operation section. An electric cord for supplying high-frequency current from a high-frequency cauterization power supply device is connected to the high-frequency connection pin. An inner end portion of the high-frequency connection pin is electrically connected to the probe distal end portion of the therapeutic section or to the jaw via an electric conduction path within the operation section and the sheath. High-frequency current is supplied, when necessary, to the probe distal end portion of the therapeutic section or to the jaw, and high-frequency therapeutic treatment, such as coagulation, of the living body tissue is performed.

In the apparatus of the above-described Patent Document 1, when high-frequency therapeutic treatment is performed, the driving pipe is axially advanced/retreated in accordance with the operation of the operation handle, and the jaw is opened/closed relative to the probe distal end portion in interlock with the operation of the driving pipe. In addition, the pin receiving section is formed at the distal end portion of the driving pipe. The pin receiving section is formed in the extension portion which is extended, as one body with the driving pipe, to the distal end side from the distal end edge portion of the driving pipe. The coupling pin is provided at the distal end portion of the pin receiving section. The driving pipe and the jaw body are coupled by the coupling pin.

BRIEF SUMMARY OF THE INVENTION

A surgical operating apparatus in one aspect of the present invention comprises: a sheath having a distal end and a proximal end; a rod-shaped probe main body which is inserted into the sheath and has a distal end and a proximal end, and which is transmitted with ultrasonic vibration; a jaw pivoted to the distal end of the sheath; a probe distal end which is provided at the distal end of the probe main body and meshes with the jaw; and a driving member which is provided with a tubular main body portion which is inserted into the sheath slidably along an axial direction of the sheath and an acting portion which is provided at a distal end of the main body portion and has a connection portion connected to the jaw, for rotating the jaw according to a sliding action of the main body portion, wherein the sheath includes a notched portion for preventing the sheath from contacting the driving member when the connection portion of the driving member with the jaw moves in a direction perpendicular to a sliding direction of the driving member at a rotation time of the jaw.

Preferably, the notched portion is formed on a peripheral wall face of the distal end of the sheath corresponding to a moving direction of the jaw at the moving time of the jaw in an opening operation direction of the jaw.

Preferably, the sheath is covered with an outer skin formed from insulating material, and the notched portion is covered with the outer skin.

Preferably, the acting portion has a tapered shape portion which is gradually and gently narrowed toward a distal end of a tubular body of the main body portion, the tapered shape portion has a U-shaped extension portion with U shape in sectional configuration at the distal end of the tubular body of the main body portion, the U-shaped extension portion has two side faces disposed so as to be opposed to each other and a connected face connecting the two side faces, the connected face has an inclined face where a distance between the two side faces is gradually tapered toward a distal end of the connected face, and the connection portion is formed on each of the two side faces disposed at distal ends of the connected face.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view that schematically shows the entire structure of an ultrasonic therapeutic apparatus according to a first embodiment of the present invention;

FIG. 4 is a longitudinal cross-sectional view showing an internal structure of the transducer unit of the ultrasonic therapeutic apparatus according to the first embodiment;

FIG. 23 is a plan view showing the driving pipe of the ultrasonic therapeutic apparatus according to the first embodiment;

FIG. 24 is a cross-sectional view taken along line 24-24 in FIG. 23;

FIG. 25 is a front view showing the driving pipe of the ultrasonic therapeutic apparatus according to the first embodiment;

FIG. 33 is an explanatory view for explaining a positional relationship between a guide groove and an engaging recess portion at the coupling section between the handle unit and sheath unit of the ultrasonic therapeutic apparatus according to the first embodiment;

FIG. 34 is a perspective view showing a connection tube body of the sheath unit of the ultrasonic therapeutic apparatus according to the first embodiment;

FIG. 35 is a perspective view showing the connection tube body of the sheath unit of the ultrasonic therapeutic apparatus according to the first embodiment;

FIG. 37 is a longitudinal cross-sectional view showing a state after engagement between the handle unit and sheath unit of the ultrasonic therapeutic apparatus according to the first embodiment;

FIG. 41A is a vertical cross-sectional view showing a state prior to engagement of the engagement section between the handle unit and sheath unit of the ultrasonic therapeutic apparatus according to the first embodiment;

FIG. 41B is a vertical cross-sectional view showing a state prior to engagement of the engagement section between the handle unit and sheath unit of the ultrasonic therapeutic apparatus according to the first embodiment;

FIG. 49 is a perspective view showing an electrode member of the ultrasonic therapeutic apparatus according to the first embodiment;

FIG. 50 is a transverse cross-sectional view showing the electrode member of the ultrasonic therapeutic apparatus according to the first embodiment;

FIG. 52 is a schematic view showing an internal structure of a cable of the transducer unit of the ultrasonic therapeutic apparatus according to the first embodiment of the present invention;

FIG. 53 is a perspective view that schematically shows the entire structure of a surgical operating apparatus according to a second embodiment of the present invention;

FIG. 56 is a longitudinal cross-sectional view showing an internal structure of the transducer unit of the surgical operating apparatus according to the second embodiment;

FIG. 65 is a longitudinal cross-sectional view showing a coupled state between the jaw and the driving pipe of the surgical operating apparatus according to the second embodiment;

FIG. 66 is a cross-sectional view taken along line 66-66 in FIG. 65;

FIG. 73 is a longitudinal cross-sectional view showing a state before assembly of a knob member of the surgical operating apparatus according to the second embodiment.

DETAILED DESCRIPTION OF THE INVENTION

A first embodiment of the present invention will now be described with reference to FIG. 1 to FIG. 52. FIG. 1 schematically shows the entire structure of a handpiece 1 of an ultrasonic therapeutic apparatus which is a surgical operating apparatus according to the first embodiment. The ultrasonic therapeutic apparatus of the present embodiment is an ultrasonic coagulation/incision apparatus. This ultrasonic coagulation/incision apparatus can perform therapeutic treatment, such as incision, resection or coagulation, of a living body tissue by making use of ultrasonic, and can also perform therapeutic treatment by high-frequency waves.

Figure 2:
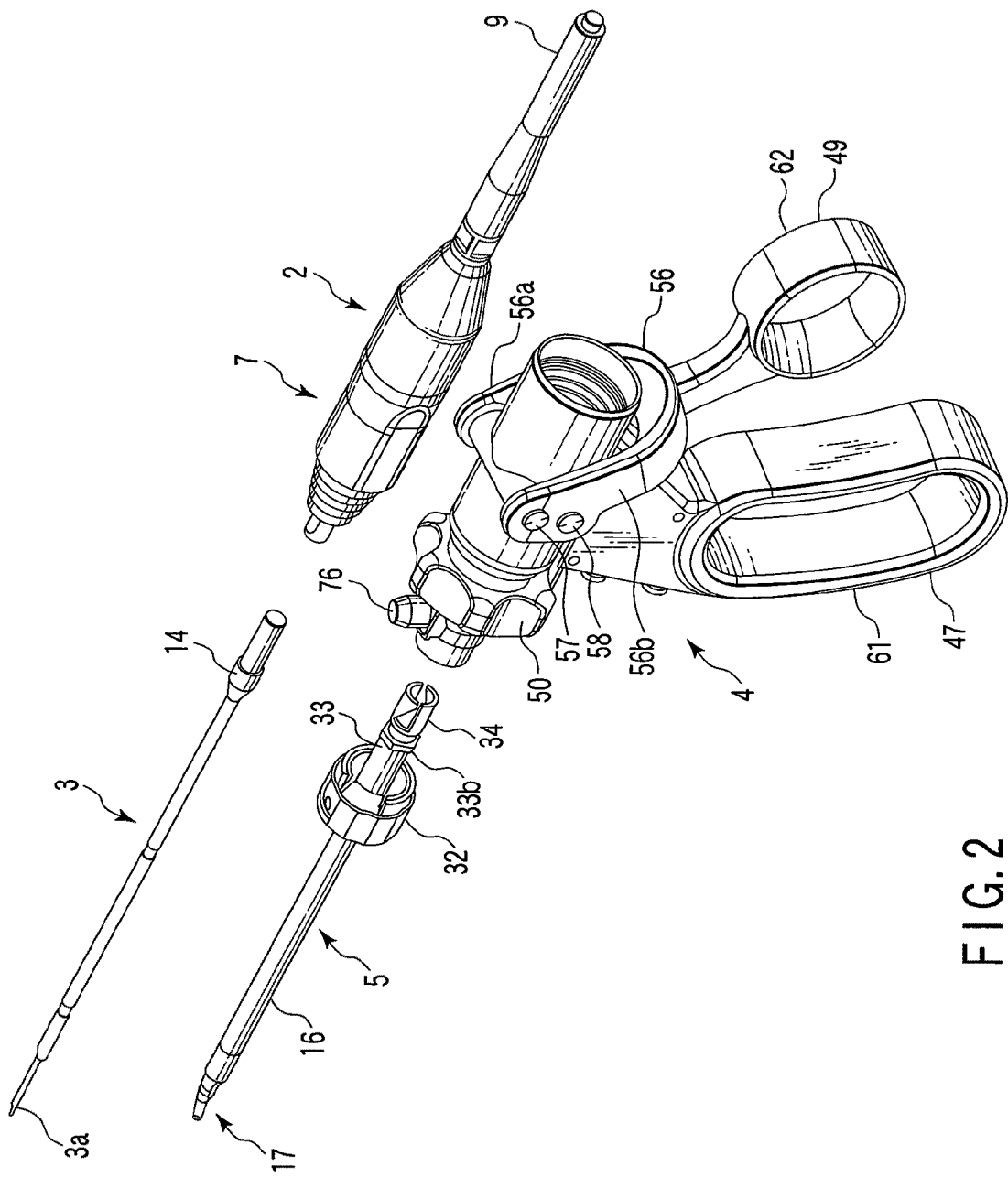
FIG. 2 is a perspective view showing a disassembled state of the ultrasonic therapeutic apparatus according to the first embodiment, with coupling sections of assembly units of the ultrasonic therapeutic apparatus being disconnected.

The handpiece 1, as shown in FIG. 2, comprises four units, namely, a transducer unit 2, a probe unit (probe section) 3, a handle unit (operation section) 4 and a sheath unit (sheath section) 5. These units are detachably coupled.

As shown in FIG. 4, an ultrasonic transducer 6 for generating ultrasonic vibration by a piezoelectric oscillator, which converts an electric current to ultrasonic vibration, is built in the transducer unit 2. An outside of the ultrasonic transducer 6 is covered with a cylindrical transducer cover 7. As shown in FIG. 1, a cable 9 for supplying an electric current for generating ultrasonic vibration from a power supply device body 8 extends from a rear end of the transducer unit 2.

A proximal end portion of a horn 10, which increases the amplitude of ultrasonic vibration, is coupled to a front end portion of the ultrasonic transducer 6. A screw hole portion 10*a* for attaching the probe is formed at a distal end portion of the horn 10.

Figure 5:
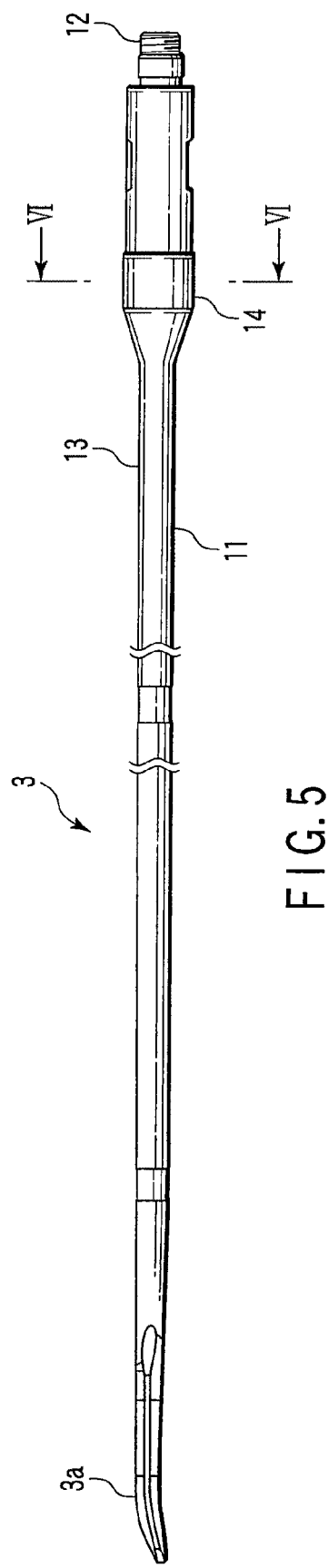
FIG. 5 is a plan view showing a probe unit of the ultrasonic therapeutic apparatus according to the first embodiment.

FIG. 5 shows the external appearance of the entire probe unit 3. The probe unit 3 is designed such that the entire length thereof may become an integer number of times of half-wave length of the ultrasonic vibration. The probe unit 3 has a distal end portion and a proximal end portion, and includes a metallic rod-shaped vibration transmission member 11 having a long axis. A proximal end portion of the vibration transmission member 11 is provided with a screw portion 12 which is to be engaged with the screw hole portion 10*a* of the horn 10. The screw portion 12 is engaged with the screw hole portion 10*a* of the horn 10 of the transducer unit 2. Thereby, the probe unit 3 and the transducer unit 2 are assembled. At this time, a first high-frequency electric path 13, through which a high-frequency current is transmitted, is formed in the coupled body of the ultrasonic transducer 6 and the probe unit 3.

Figure 7:
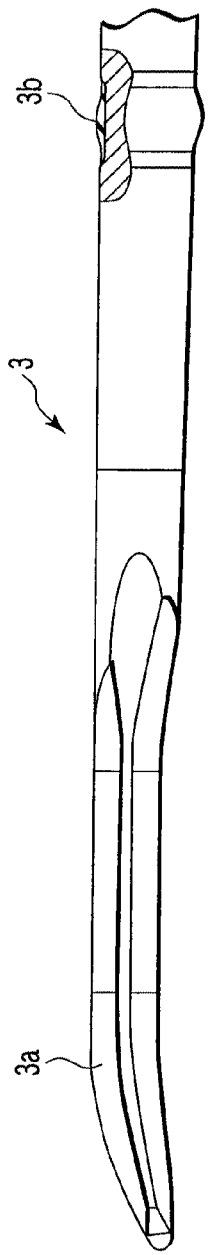
FIG. 7 is a plan view showing a distal end portion of the probe unit of the ultrasonic therapeutic apparatus according to the first embodiment.

A probe distal end portion 3*a* is provided at a distal end portion of the vibration transmission member 11. The probe distal end portion 3*a* is formed in a substantially J-shaped curved form. The probe distal end portion 3*a* constitutes a first electrode section which is one of bipolar electrodes. The cross-sectional area of the probe unit 3 is decreased in the axial direction at several nodes of vibration in the axial direction, so that an amplitude necessary for therapeutic treatment can be obtained at the probe distal end portion 3*a*. Rubber rings 3*b* (see FIG. 7), which are formed of elastic material in an annular shape, are attached to several positions of nodes of vibration along the axial direction of the probe unit 3. The rubber rings 3*b* prevent interference between the probe unit 3 and the sheath unit 5.

Figure 6:
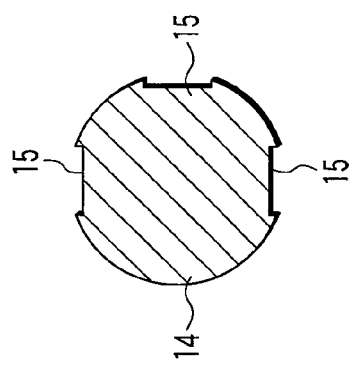
FIG. 6 is a cross-sectional view taken along line VI-VI in FIG. 5.

A flange portion 14 is provided at the position of the node of vibration on the most proximal end side in the axial direction of the probe unit 3. As shown in FIG. 6, engaging recess portions 15 each having a key groove shape are formed on the outer peripheral surface of the flange portion 14 at three positions in the circumferential direction thereof.

Figure 8B:
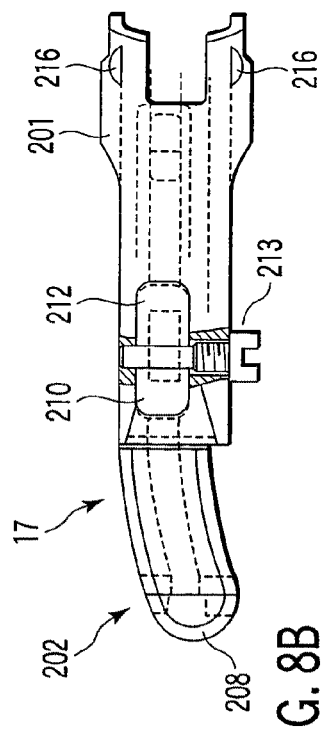
FIG. 8B is a plan view showing a jaw of the sheath unit of the ultrasonic therapeutic apparatus according to the first embodiment.
Figure 8A:
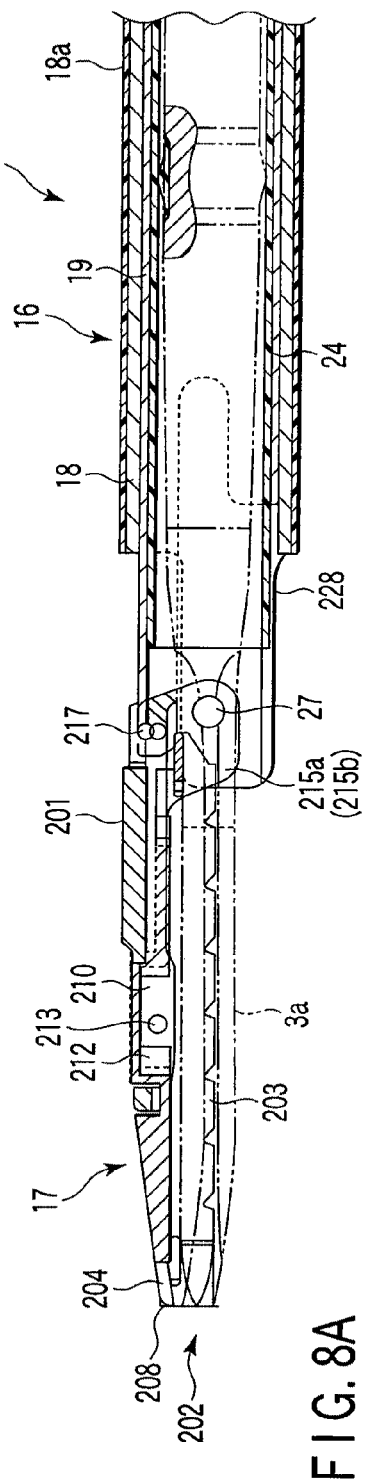
FIG. 8A is a longitudinal cross-sectional view showing a distal end portion of a sheath unit of the ultrasonic therapeutic apparatus according to the first embodiment.
Figure 9A:
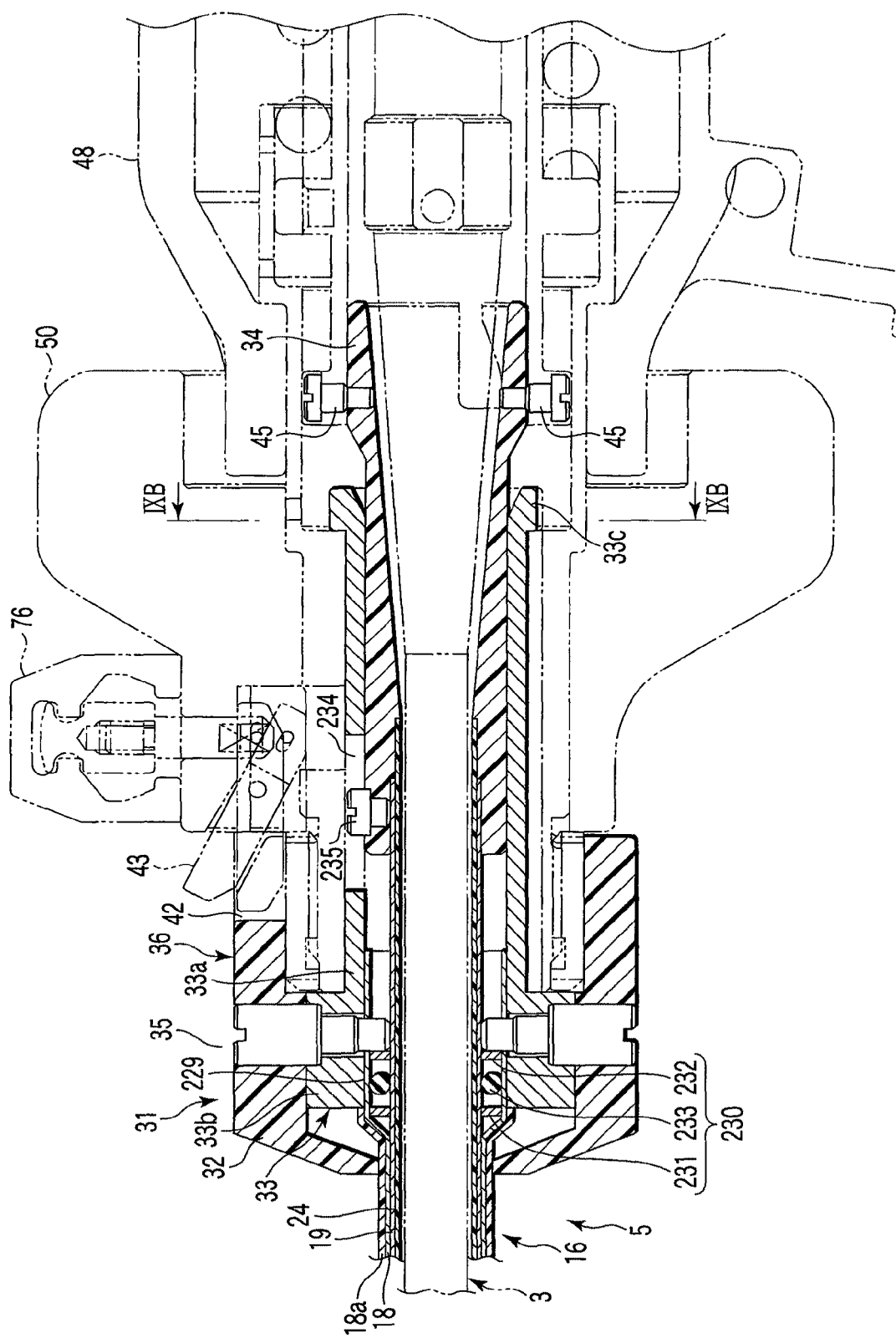
FIG. 9A is a longitudinal cross-sectional view showing a proximal end portion of the sheath unit of the ultrasonic therapeutic apparatus according to the first embodiment.

FIG. 8A shows a distal end portion of the sheath unit 5, and FIG. 9A shows a proximal end portion of the sheath unit 5. As shown in FIG. 8A, the sheath unit 5 includes a sheath body 16, which is formed of a cylindrical body, and a jaw 17 which is provided at a distal end of the sheath body 16. The sheath body 16 includes a metallic sheath 18 which is an outer cylinder, and a metallic driving pipe 19 which is an inner cylinder. The driving pipe 19 is axially movably inserted in the sheath 18.

As shown in FIG. 8A, the outer peripheral surface of the sheath 18 is covered with an outer coating 18*a* which is formed of an insulating material such as a resin. An insulation tube 24, which is formed of an insulating material, is provided on the inner peripheral side of the driving pipe 19.

Figure 10:
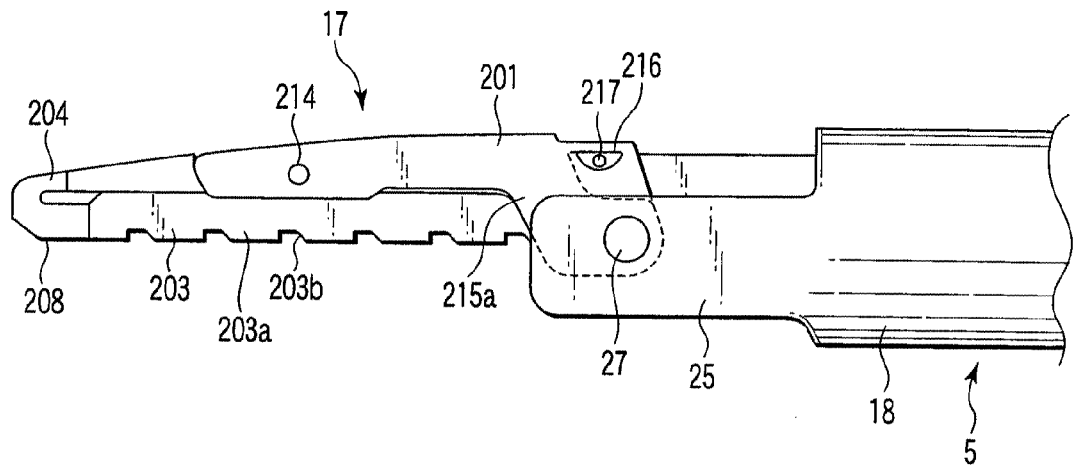
FIG. 10 is a side view showing an attachment section of the jaw of the ultrasonic therapeutic apparatus according to the first embodiment.
Figure 11:
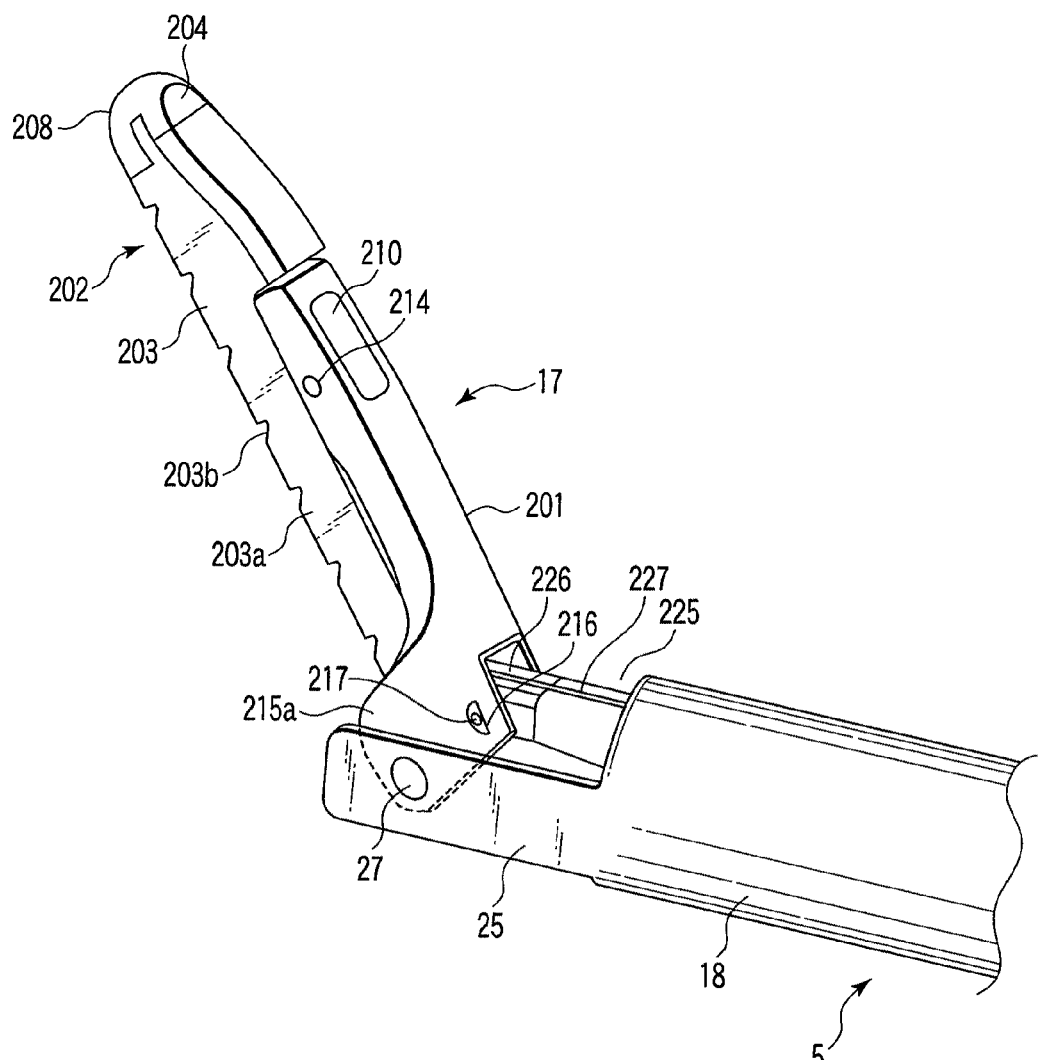
FIG. 11 is a perspective view showing a state in which the jaw of the ultrasonic therapeutic apparatus according to the first embodiment is opened.
Figure 12:
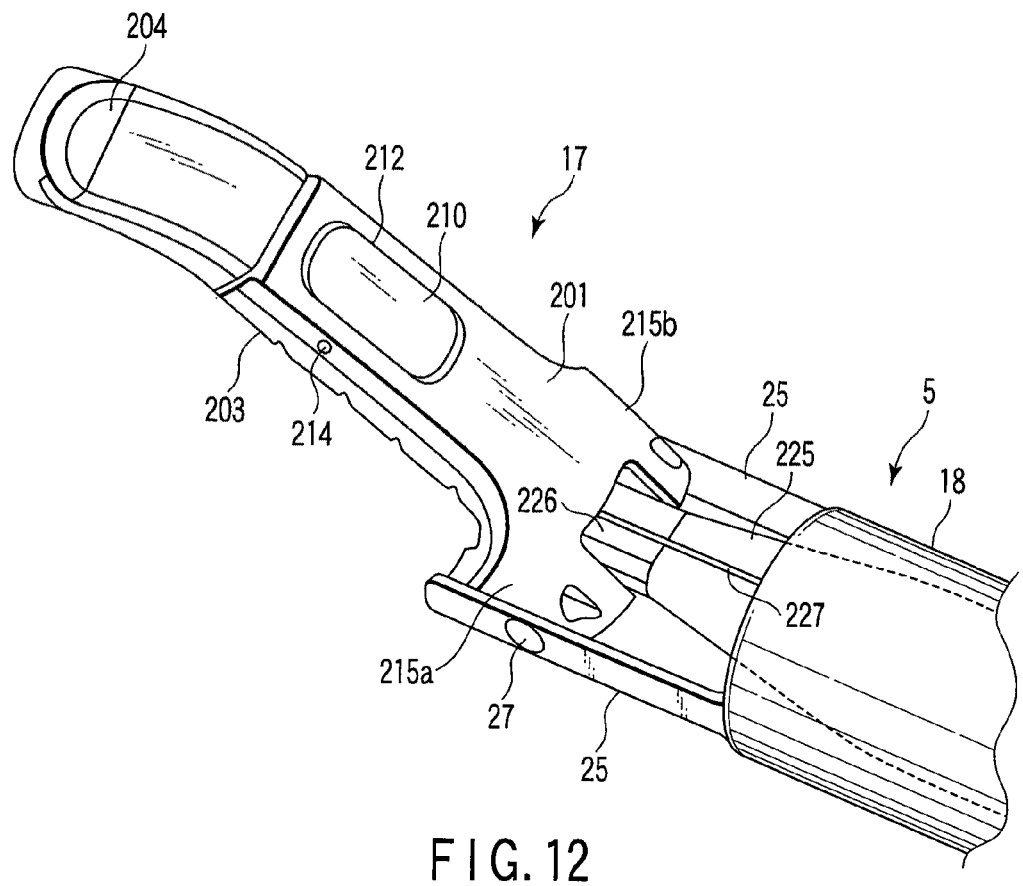
FIG. 12 is a perspective view showing, in a direction different from the direction in FIG. 11, the state in which the jaw of the ultrasonic therapeutic apparatus according to the first embodiment is opened.
Figure 13:
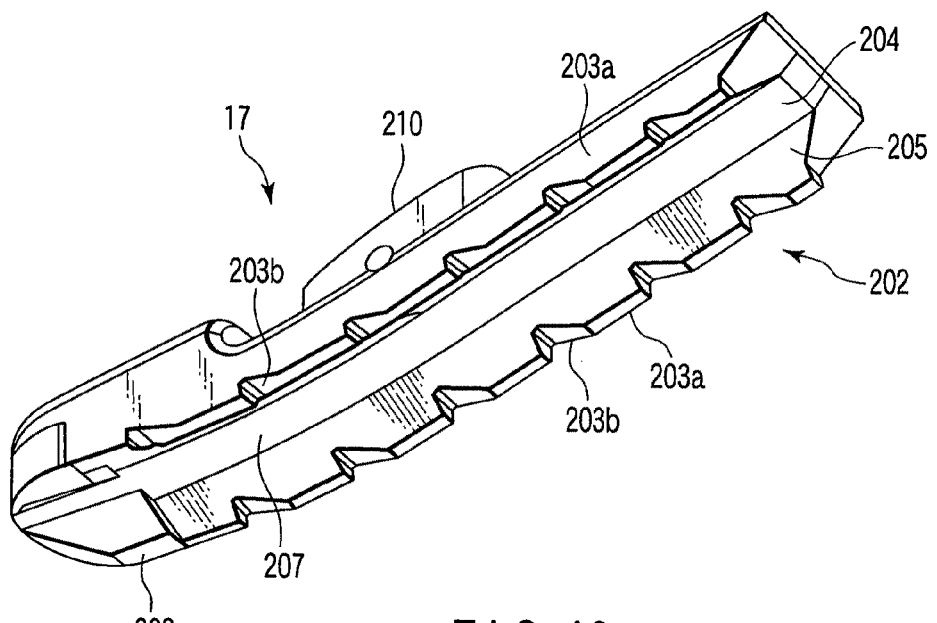
FIG. 13 is a perspective view showing a hold member of the jaw of the ultrasonic therapeutic apparatus according to the first embodiment.

As shown in FIGS. 10 to 12, a pair of right and left projection portions 25 are provided at a distal end portion of the sheath 18 so as to project in a forward direction of the sheath 18. A proximal end portion of the jaw 17 is rotatably attached to the projection portions 25 via a support pin 27. When the probe unit 3 and the sheath unit 5 are assembled, the jaw 17 is positioned to be opposed to the probe distal end portion 3*a* of the probe unit 3.

As shown in FIG. 8B, the jaw 17 is formed in a substantially J-shaped curved form, which corresponds to the curved shape of the probe distal end portion 3*a*, in accordance with the curved shape of the probe distal end portion 3*a* of the probe unit 3. The jaw 17 is configured to be rotated about the support pin 27 by the advancing/retreating movement of the driving pipe 19 in the axial direction. A therapeutic section 1A of the handpiece 1 is constituted by the jaw 17 and the probe distal end portion 3*a*.

Figure 14:
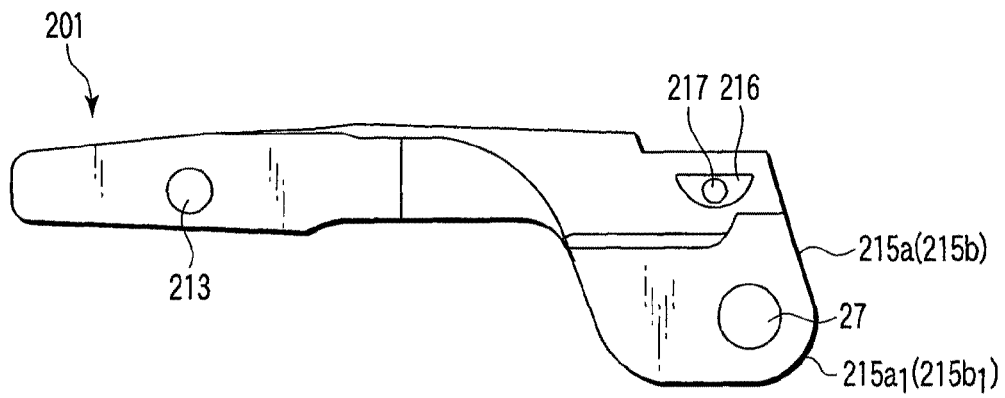
FIG. 14 is a side view showing a jaw body of the jaw of the ultrasonic therapeutic apparatus according to the first embodiment.
Figure 15:
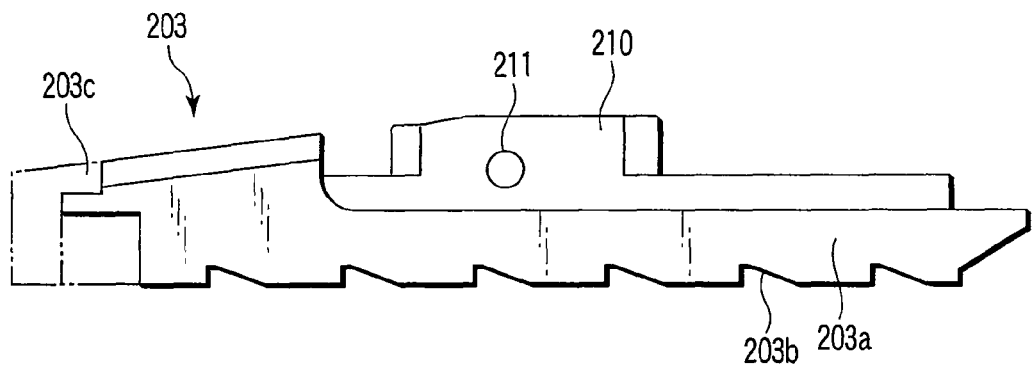
FIG. 15 is a side view showing an electrode member of the jaw of the ultrasonic therapeutic apparatus according to the first embodiment.

The jaw 17 includes a metallic jaw body 201 (see FIG. 14) which is an electrically conductive member, and a hold member 202 which is attached to the jaw body 201. The hold member 202 is composed of an electrode member 203 (see FIG. 15) for high-frequency therapeutic treatment, and an insulation member 204 (see FIG. 16) for ultrasonic therapeutic treatment. The electrode member 203 constitutes a second electrode section which is the other electrode of the bipolar electrodes.

Figure 17:
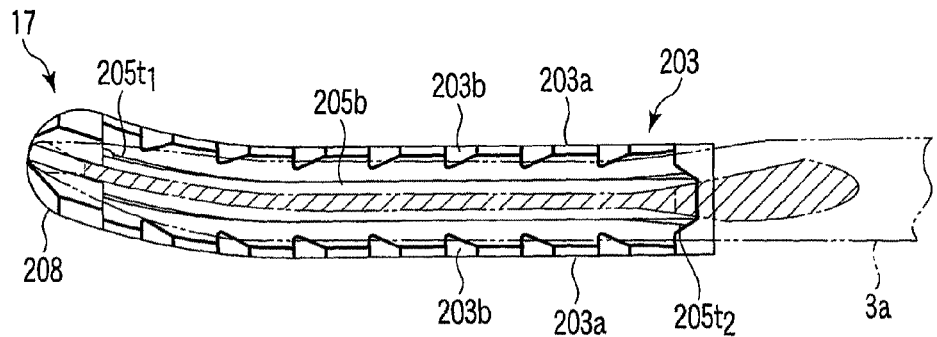
FIG. 17 is a plan view showing an engaged state between the electrode member of the jaw and the probe distal end portion of the ultrasonic therapeutic apparatus according to the first embodiment.
Figure 18:
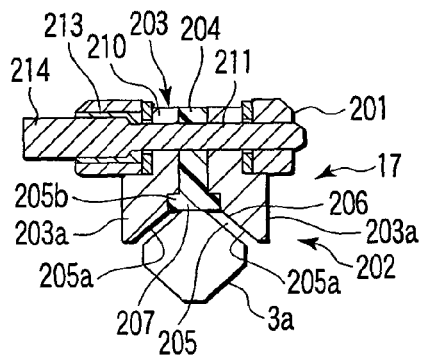
FIG. 18 is a vertical cross-sectional view showing an engaged state between the electrode member of the jaw and the probe distal end portion of the ultrasonic therapeutic apparatus according to the first embodiment.

As shown in FIGS. 17 and 18, a groove portion 205, which is formed in accordance with the curved shape of the probe distal end portion 3*a*, is formed on the lower surface of the electrode member 203. An engaging surface 206, which is to be engaged with the probe distal end portion 3*a*, is formed by the groove portion 205. A groove width W of the groove portion 205 is set in consideration of the diameter dimension of the probe distal end portion 3*a*. Specifically, the groove width W is set to be greater than the diameter dimension of the probe distal end portion 3*a* by a predetermined ratio, thereby preventing contact between the engaging surface 206 of the electrode member 203 and the probe distal end portion 3*a*.

Figure 19:
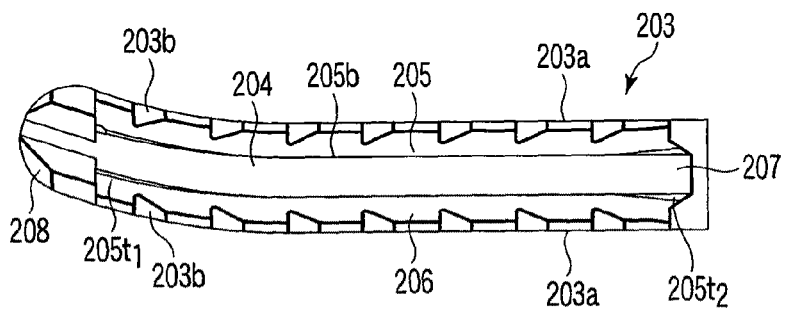
FIG. 19 is a plan view showing a living body tissue contact surface of the hold member of the jaw of the ultrasonic therapeutic apparatus according to the first embodiment.
Figure 20:
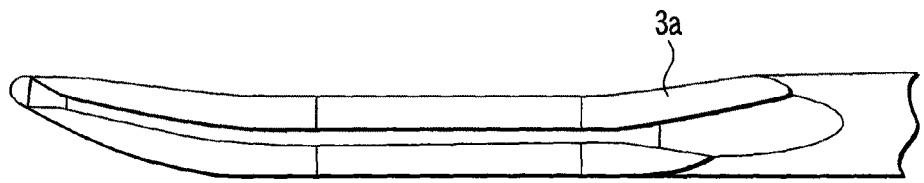
FIG. 20 is a plan view showing the probe distal end portion of the ultrasonic therapeutic apparatus according to the first embodiment.

Inclined surfaces 205*a*, which are configured to gradually increase the groove width toward a lower-side opening surface, as shown in FIG. 18, are formed on both side wall surfaces of the groove portion 205. In addition, as shown in FIG. 19, tooth portions 203*b* for preventing a slip are formed on both side walls 203*a* of the groove portion 205 on the lower-side opening surface side. The tooth portions 203*b* form a slip-preventing section for preventing a slip of a clamped object between the probe distal end portion 3*a* and the jaw 17 when the jaw 17 and probe distal end portion 3*a* are engaged. A wall thickness T of the electrode member 203 is properly determined in consideration of the rigidity and coagulation performance.

Further, in the electrode member 203, a notch portion 205*b* is formed at a bottom portion of the groove portion 205. The notch portion 205*b* is formed in accordance with the curved shape of the probe distal end portion 3*a*. A pad member 207, which is formed of an insulating material, for instance, a resin material such as polytetrafluoroethylene, is disposed in the notch portion 205*b*. As shown in FIG. 18, the pad member 207 is a probe contact member which is in contact with the probe distal end portion 3a. The probe distal end portion 3a comes in contact with the pad member 207, thus securing a clearance between the second electrode section of the electrode member 203 and the probe distal end portion 3a.

In addition, the jaw 17 has a block-shaped distal end chip 208 at a distal end portion of the engaging surface 206 for engagement with the probe distal end portion 3a. The distal end chip 208 is formed of an insulating material, for instance, a resin material such as polytetrafluoroethylene. When the jaw 17 and probe distal end portion 3a are engaged, a positional displacement relative to the probe distal end portion 3a is tolerated by the distal end chip 208.

Figure 16:
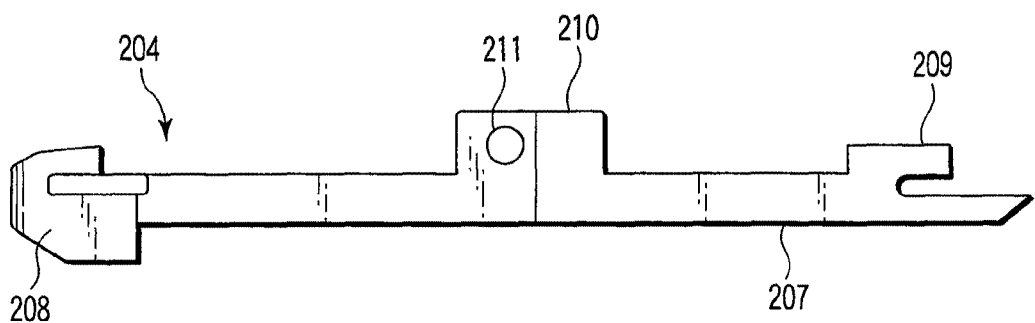
FIG. 16 is a side view showing an insulation member of the jaw of the ultrasonic therapeutic apparatus according to the first embodiment.

As shown in FIG. 16, in the insulation member 204, the distal end chip 208 is coupled to the distal end portion of the pad member 207. In the insulation member 204, the pad member 207 and the distal end chip 208 are provided as one body.

The electrode member 203 and insulation member 204 are integrally assembled to form the hold member 202. A hook-shaped engaging portion 209 is formed at a rear end portion of the insulation member 204. In addition, a distal end chip engaging portion 203c, which engages the distal end chip 208, is formed at the distal end portion of the electrode member 203. When the electrode member 203 and the insulation member 204 are assembled, the distal end chip 208 is engaged with the distal end chip engaging portion 203c, and also the engaging portion 209 at the rear end portion of the insulation member 204 is engaged with the rear end portion of the electrode member 203 in the state in which the pad member 207 is inserted in the notch portion 205b of the groove portion 205 of the electrode member 203.

A projection portion 210 for attachment is provided on that side of the hold member 202, which is opposed to the engaging surface 206 for engagement with the probe distal end portion 3a. A screw insertion hole 211 is formed in the projection portion 210.

A hold member engaging portion 212, which engages the projection portion 210 of the hold member 202, is provided on a distal end side of the jaw body 201. The hold member 202 is engaged with the hold member engaging portion 212. Further, a screw hole 213 is formed in side wall portions of the hold member engaging portion 212. As shown in FIG. 18, when the hold member engaging portion 212 of the jaw body 201 and the projection portion 210 of the hold member 202 are engaged, a fixing screw 214, which is engaged in the screw hole 213 of the jaw body 201, is inserted in the screw insertion hole 211 of the hold member 202. In this state, the fixing screw 214 is fastened in the screw hole 213, and thereby the hold member 202 is attached to the jaw body 201. The electrode member 203 of the hold member 202 and the jaw body 201 are electrically connected via the fixing screw 214.

A proximal end portion of the jaw body 201 has two-forked arm portions 215a and 215b. The respective arm portions 215a and 215b have extension portions 215a1 and 215b1, which extend obliquely downward from a position of a center line of the jaw body 201. The extension portions 215a1 and 215b1 are rotatably attached by the support pin 27 to the right and left projection portions 25 at the distal end portion of the sheath 18.

A coupling pin insertion hole 216 is formed in a proximal portion of each of the two arm portions 215a and 215b. A coupling pin 217 for coupling the jaw body 201 and the driving pipe 19 is inserted in the coupling pin insertion holes 216. The jaw body 201 and the driving pipe 19 are electrically connected via the coupling pin 217.

Thereby, the driving force of the driving pipe 19 is transmitted to the jaw 17 via the coupling pin 217 by the advancing/retreating in the axial direction of the driving pipe 19. Accordingly, the jaw 17 is rotated about the support pin 27. In this case, when the driving pipe 19 is pulled rearward, the jaw 17 is rotated about the support pin 27 and driven (to an open position) in a direction away from the probe distal end portion 3a. Conversely, when the driving pipe 19 is pushed forward, the jaw 17 is rotated about the support pin 27 and driven (to a closed position) in a direction toward the probe distal end portion 3a. A living body tissue is held between the jaw 17 and the probe distal end portion 3a of the probe unit 3 when the jaw 17 is rotated to the closed position.

The therapeutic section 1A of the handpiece 1 is constituted by the jaw 17 and the probe distal end portion 3a of the probe unit 3. The therapeutic section 1A is configured to selectively perform a plurality of therapeutic functions, for example, two therapeutic functions (a first therapeutic function and a second therapeutic function) in this embodiment. For instance, the first therapeutic function is set to be a function of simultaneously outputting an ultrasonic therapeutic output and a high-frequency therapeutic output. The second therapeutic function is set to be a function of outputting only the high-frequency therapeutic output.

The first therapeutic function and second therapeutic function of the therapeutic section 1A are not limited to the above-described configuration. For example, the first therapeutic function may be set to be a function of outputting an ultrasonic therapeutic output in a maximum output state, and the second therapeutic function may be set to be a function of outputting the ultrasonic therapeutic output in a preset arbitrary output state which is lower than the maximum output state.

As shown in FIGS. 17 and 19, the jaw 17 has, at a distal end portion of the groove portion 205, a distal-end-side groove width varying section 205t1 which has such a tapering shape that the groove width of the groove portion 205 gradually increases toward the distal end. In addition, the jaw 17 has, at a proximal end portion of the groove portion 205, a proximal-end-side groove width varying section 205t2 which has such a tapering shape that the groove width of the groove portion 205 gradually increases toward the proximal end. In the distal-end-side groove width varying section 205t1 and proximal-end-side groove width varying section 205t2, a positional displacement in assembly between the probe distal end portion 3a and the electrode member 203 of the jaw 17 can be tolerated in a case where the assembly position of the electrode member 203 of the jaw 17 is slightly displaced, relative to the probe distal end portion 3a, in the axial direction of the sheath unit 5 when the probe unit 3 and the sheath unit 5 are assembled.

Figure 21:
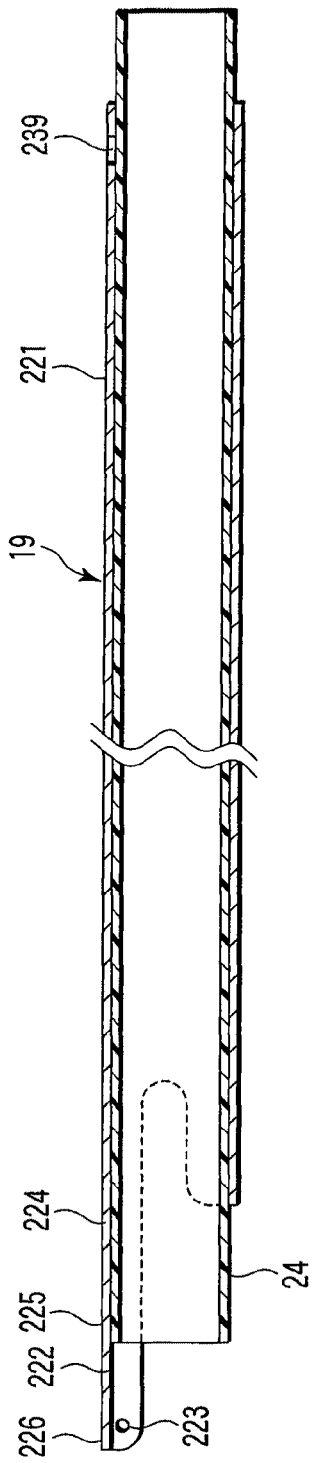
FIG. 21 is a longitudinal cross-sectional view showing a driving pipe of the ultrasonic therapeutic apparatus according to the first embodiment.

FIG. 21 shows the driving pipe 19. The driving pipe 19 includes a tubular body section 221 and an operating section 222. The body section 221 is inserted in the sheath 18 so as to be slidable in the axial direction of the sheath 18. The operating section 222 is disposed on the distal end side of the body section 221, and includes a connection section 223 which is connected to the jaw 17.

Figure 22:
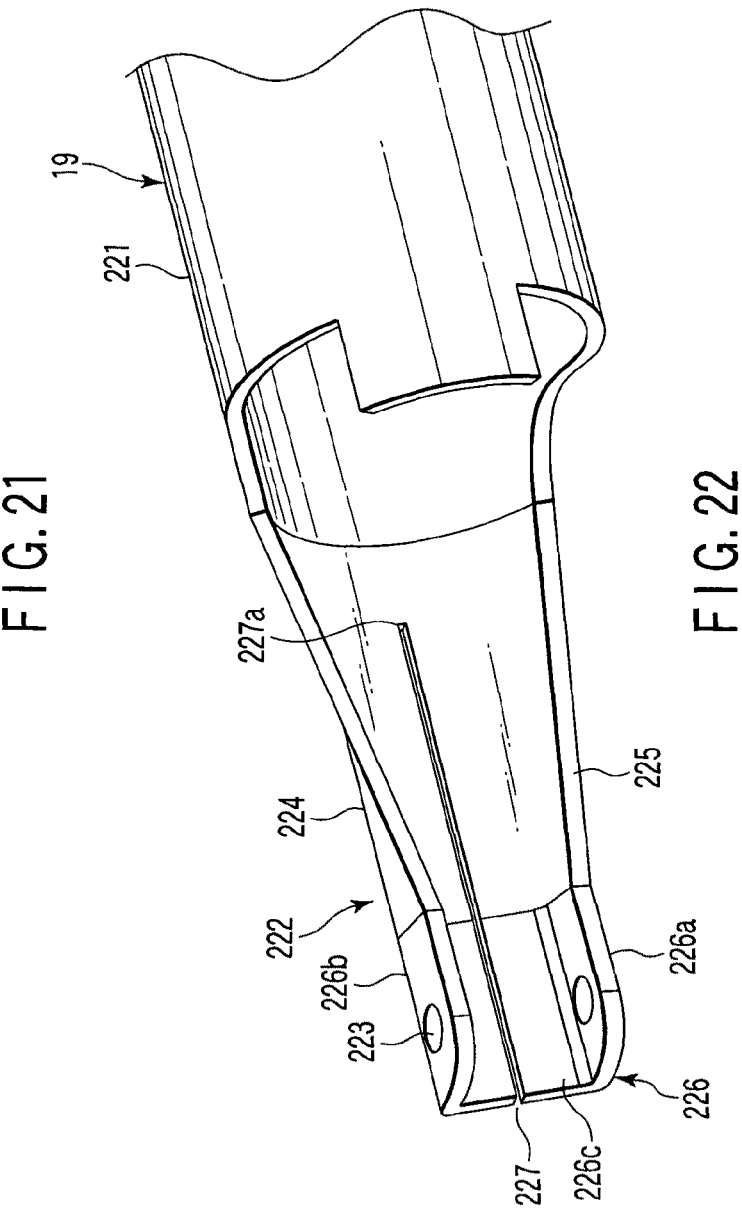
FIG. 22 is a perspective view showing a distal end portion of the driving pipe of the ultrasonic therapeutic apparatus according to the first embodiment.

As shown in FIG. 22, the peripheral wall of a tubular distal end portion of the body section 221 includes a crescent-shaped arcuate cross-sectional portion 224, which is formed by leaving a substantially crescent-shaped arcuate cross-sectional portion over a predetermined length in the axial direction, and cutting out the other portion. As shown in FIG. 23, the arcuate cross-sectional portion 224 includes a taper portion 225 with a tapered distal end portion, which is gradually tapered toward the distal end side. As shown in FIG. 22 and FIG. 25, a U-shaped portion 226 having a U-shaped cross section is formed at a distal end of the taper portion 225. The operating section 222 is constituted by the U-shaped portion 226.

As shown in FIG. 22, the U-shaped portion 226 has two side surfaces 226a and 226b, which are opposed to each other, and a connecting surface 226c which connects the two side surfaces 226a and 226b. The connection section 223 is formed in each of the two side surfaces 226a and 226b of the U-shaped portion 226.

The operating section 222 has a slit 227 extending in the axial direction of the sheath 18 in a distal end portion of the connecting surface 226c. As shown in FIG. 23, the slit 227 has a terminal end portion 227a which is located at a position corresponding to a proximal end portion of the taper portion 225.

As shown in FIG. 8A, the insulation tube 24 includes a projection portion 228 which projects forward of the body section 221 of the driving pipe 19. The projection portion 228 extends up to a rear end position of the U-shaped portion 226.

Further, a proximal end portion of the insulation tube 24 extends to a proximal end side of the sheath body 16. The driving pipe 19 and probe unit 3 are electrically insulated by the insulation tube 24.

FIG. 9 shows a proximal end portion of the sheath body 16. The proximal end portion of the sheath 18 includes a flare portion 229 which has a greater inside diameter than the other portion. A proximal end portion of the driving pipe 19 extends more rearward than the flare portion 229 of the sheath 18.

Seal means 230 for effecting sealing between the sheath 18 and the driving pipe 19 is provided between the flare portion 229 and the driving pipe 19. The seal means 230 includes two backup rings 231 and 232 and one O ring 233. The two backup rings 231 and 232 are disposed between the flare portion 229 and the driving pipe 19 in the state in which the two backup rings 231 and 232 are paired in a back-and-forth direction along the axis of the sheath 18. The O ring 233 is provided between the backup rings 231 and 232 so as to be movable in the axial direction of the sheath 18.

In addition, the proximal end portion of the sheath body 16 is provided with an attachment/detachment mechanism section 31 for attachment/detachment to/from the handle unit 4. The attachment/detachment mechanism section 31 includes a cylindrical large-diameter handle member 32 which is formed of a resin material, a guide cylindrical body (first tubular member) 33 which is formed of a metallic cylindrical body, and a cylindrical connection tube body (second tubular member) 34 which is formed of a resin material.

The guide cylindrical body 33 includes a tubular body 33a which is fitted on the flare portion 229 of the proximal end portion of the sheath 18 and extends rearward. A distal end portion of the tubular body 33a is provided with a large-diameter 33b which has a greater outside diameter than the other portion thereof. The handle member 32 is fitted on the large-diameter portion 33b. A connection flange portion 33c, which projects outward, is formed on an outer peripheral surface of a rear end portion of the guide cylindrical body 33.

Figure 27:
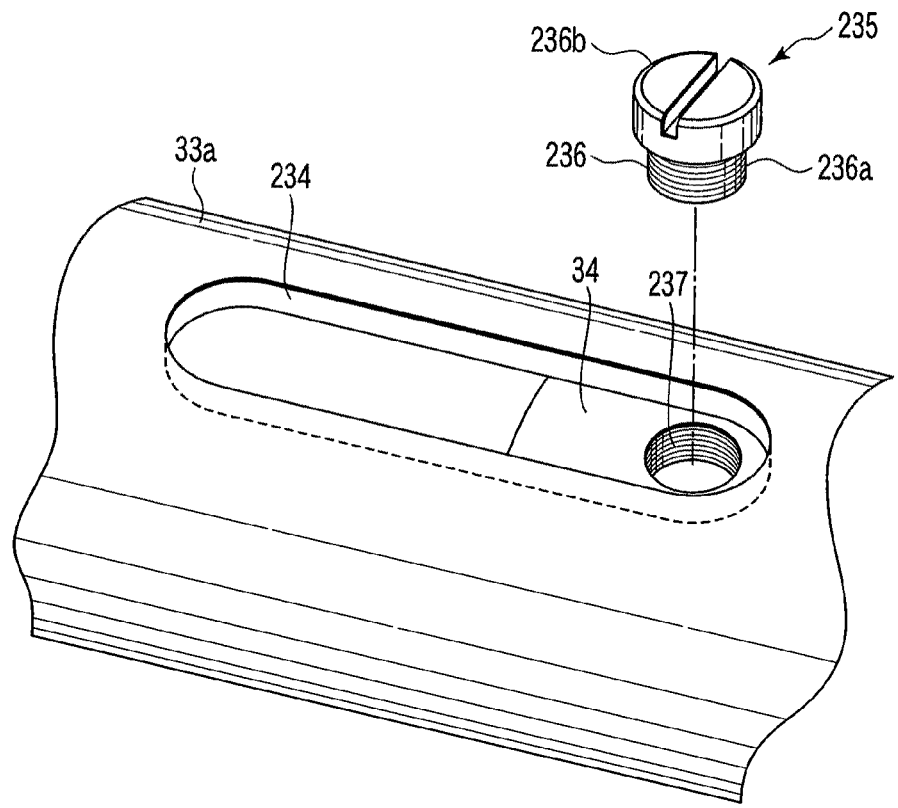
FIG. 27 is a perspective view showing the state before the threaded pin is engaged in the assembly section at the proximal end portion of the sheath unit of the ultrasonic therapeutic apparatus according to the first embodiment.

As shown in FIG. 27, an outer peripheral wall portion of the tubular 33a has an elongated slit 234 extending in the axial direction of the sheath 18. In addition, on the rear end portion side of the guide cylindrical body 33, a distal end portion of the connection tube body 34 is inserted so as to be slidable in the axial direction of the sheath 18. A proximal end portion of the driving pipe 19 is fitted and inserted inside the inner peripheral surface of the distal end portion of the connection tube body 34.

Figure 26:
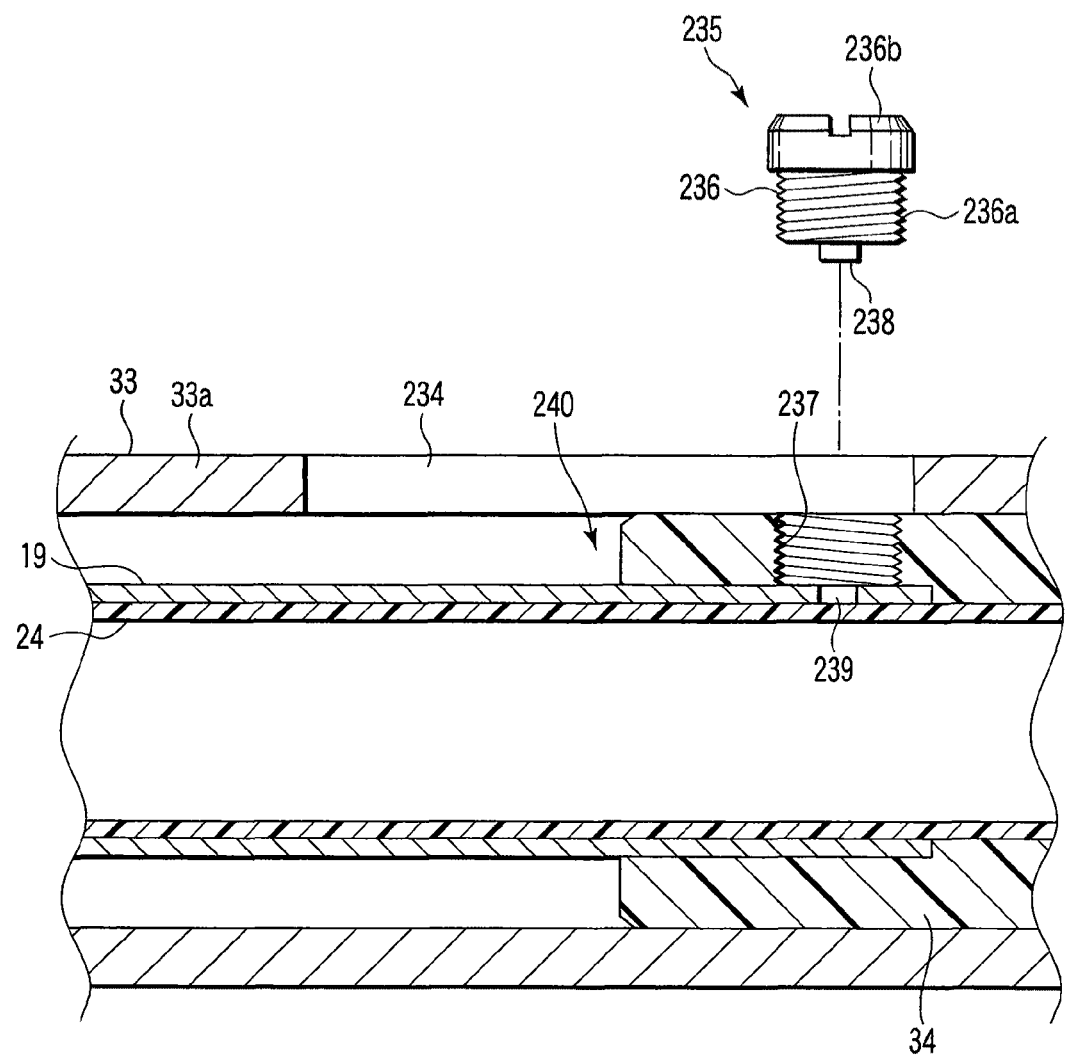
FIG. 26 is a longitudinal cross-sectional view showing a state before a threaded pin is engaged in an assembly section at the proximal end portion of the sheath unit of the ultrasonic therapeutic apparatus according to the first embodiment.
Figure 28:
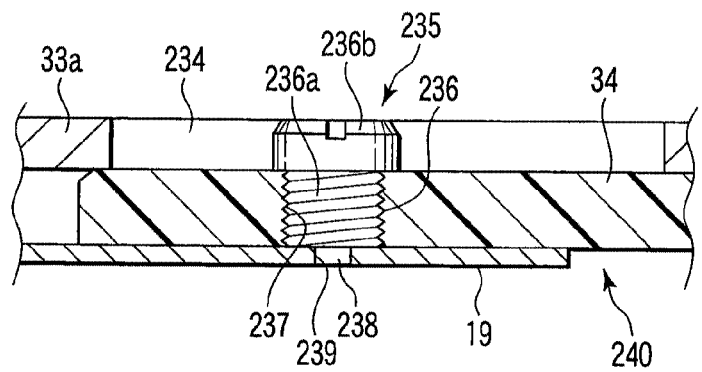
FIG. 28 is a longitudinal cross-sectional view showing the state in which the threaded pin is engaged in the assembly section at the proximal end portion of the sheath unit of the ultrasonic therapeutic apparatus according to the first embodiment.

As shown in FIG. 28, a threaded pin (projection body) 235 is fixed to a proximal end portion of the driving pipe 19. As shown in FIG. 26, the threaded pin 235 includes a male screw member 236. A threaded hole portion 237, which is engaged with a male screw portion 236a of the threaded pin 235, is formed in the connection tube body 34.

A large-diameter portion 236b, which has a greater diameter than the male screw portion 236a, is formed on a head portion of the screw member 236. The large-diameter portion 236b of the threaded pin 235 is an engaging portion which is engaged in the slit 234 of the guide cylindrical body 33.

A small-diameter portion 238, which has a smaller diameter than the male screw portion 236a, is provided on the threaded pin 235 so as to project on a side opposite to the head portion of the screw member 236. The small-diameter portion 238 is inserted and fitted in a fixing hole 239 which is formed in a proximal end portion of the driving pipe 19. Thereby, the male screw portion 236a of the threaded pin 235 is engaged in and passed through the screw hole portion 237 of the connection tube body 34, and a coupling body 240, in which the driving pipe 19 and the connection tubular body 34 are coupled, is formed. Further, the large-diameter portion 236b of the threaded pin 235 is engaged with the slit 234 of the guide cylindrical body 33, and thereby the coupling body 240 is coupled to the guide cylindrical body 33 so as to be movable as one body along the slit 234 in the axial direction of the sheath 18.

A fixing section 35 of the guide cylindrical body 33 is formed by an engaging section between the handle member 32 and the large-diameter portion 33b of the guide cylindrical body 33. Further, in the handle member 32, an attachment/detachment section 36 for attachment/detachment to/from the handle unit 4 is disposed on the rear side of the fixing section 35.

Figure 29:
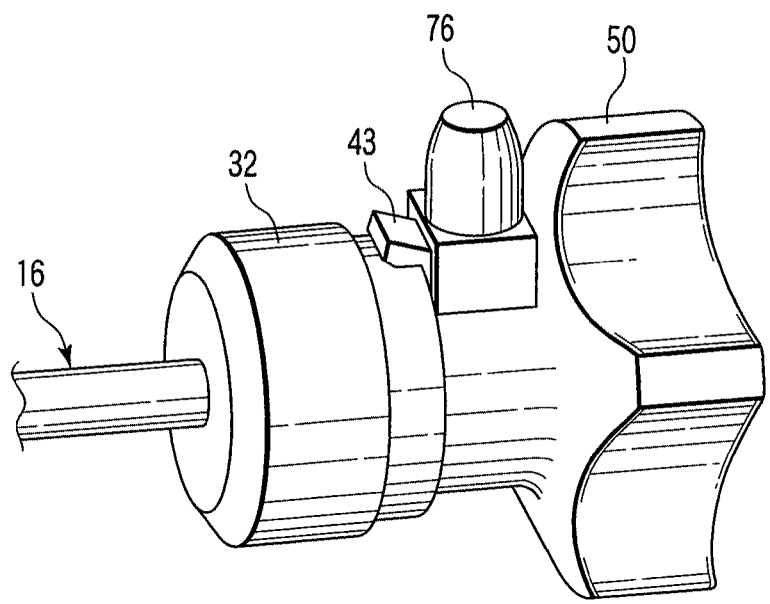
FIG. 29 is a perspective view showing a state prior to rotational engagement at the time when the handle unit and sheath unit of the ultrasonic therapeutic apparatus according to the first embodiment are coupled.
Figure 30:
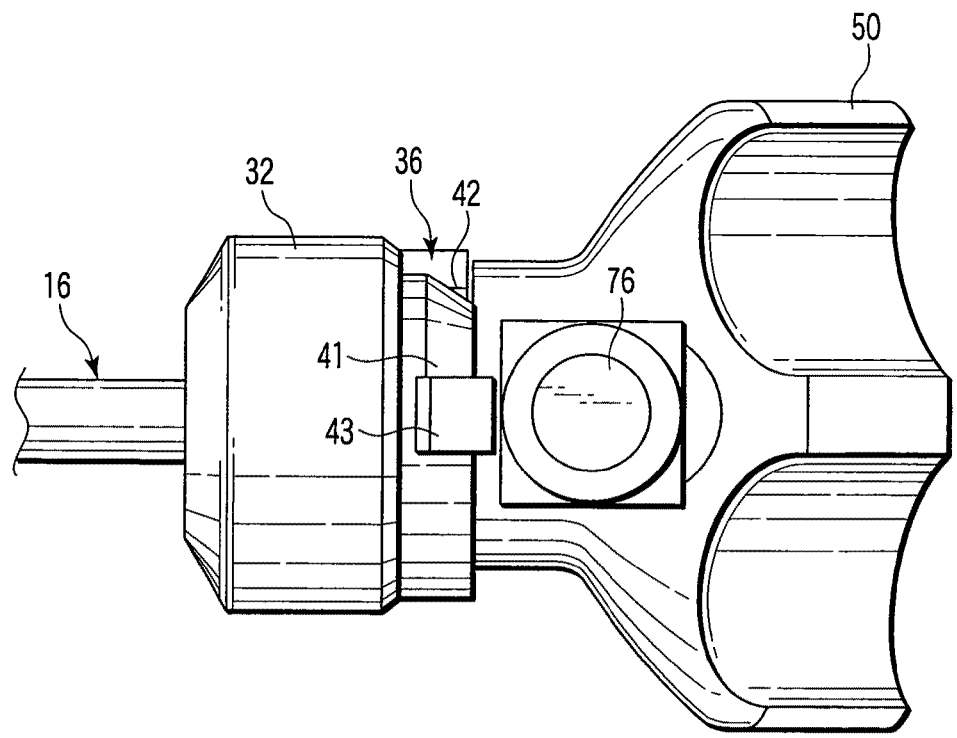
FIG. 30 is a plan view showing the state prior to rotational engagement at the time when the handle unit and sheath unit of the ultrasonic therapeutic apparatus according to the first embodiment are coupled.
Figure 31:
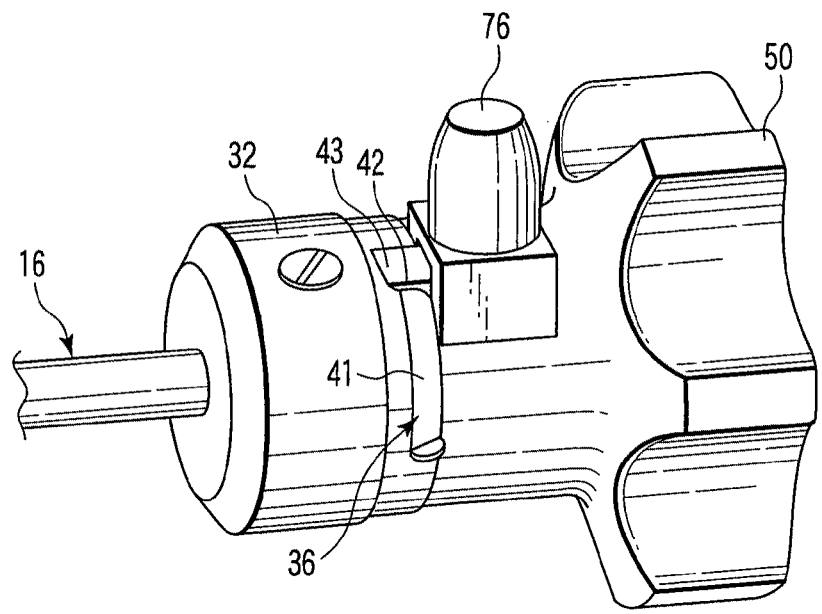
FIG. 31 is a perspective view showing a state after the rotational engagement at the time when the handle unit and sheath unit of the ultrasonic therapeutic apparatus according to the first embodiment are coupled.
Figure 32:
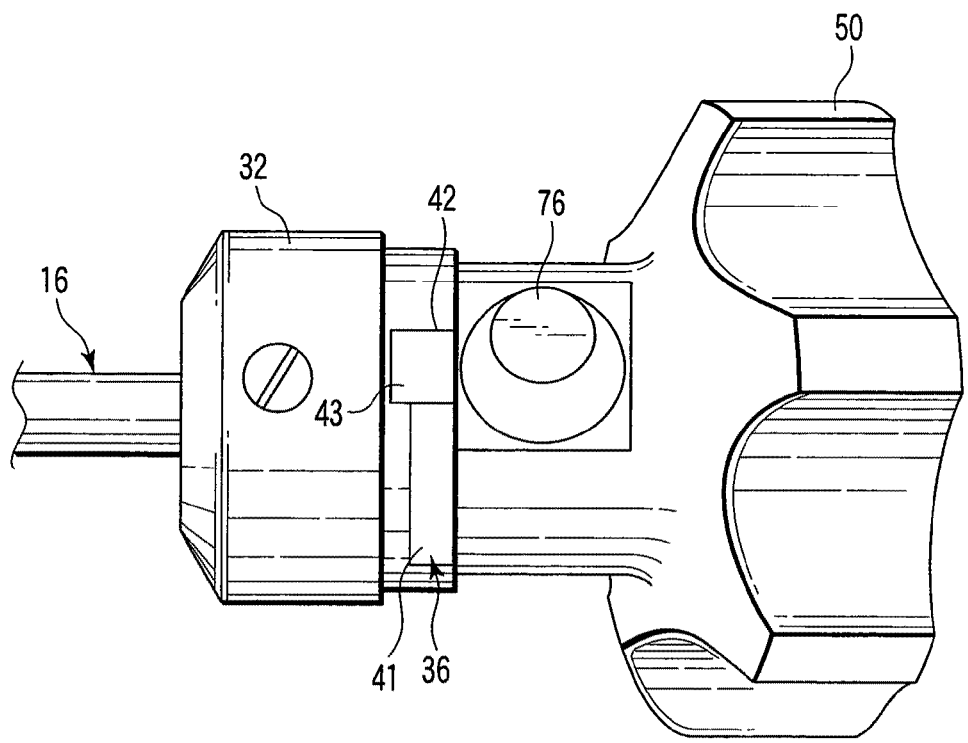
FIG. 32 is a plan view showing the state after the rotational engagement at the time when the handle unit and sheath unit of the ultrasonic therapeutic apparatus according to the first embodiment are coupled.

FIG. 29 to FIG. 32 show the structure of the attachment/detachment part between the handle member 32 and the handle unit 4. As shown in FIGS. 30 to 32, the attachment/detachment section 36 of the handle member 32 has a guide groove 41 with an inclined surface, and an engaging recess portion 42. The guide groove 41 is provided to extend in a circumferential direction on the outer peripheral surface of the proximal end portion of the handle member 32. In addition, the guide groove 41 has a tapered inclined surface with an outside diameter decreasing toward the rear end portion side of the handle member 32.

As shown in FIG. 33, the engaging recess portion 42 is formed at one end portion of the guide groove 41. The engaging recess portion 42 is formed of a recess portion having a smaller diameter than the inclined surface of the guide groove 41. The engaging recess portion 42 is configured such that the engaging lever 43 (to be described later) on the handle unit 4 side is disengageably engaged in the engaging recess portion 42. FIGS. 31 and 32 show the state in which the engaging lever 43 is engaged in the engaging recess portion 42, and FIGS. 29 and 30 show the disengaged state in which the engaging lever 43 is pulled out of the engaging recess portion 42.

As shown in FIGS. 34 and 35, a proximal end portion of the connection tube body 34 has two guide grooves 44 which are used at a time of attachment/detachment to/from the handle unit 4 side. The guide grooves 44 are configured such that two engaging pins 45 (to be described later) on the handle unit 4 side are disengageably engaged in the guide grooves 44, respectively. An engaging groove 44a, which restricts movement of the engaging pin 45 in the axial direction of the sheath body 16, is formed at a terminal end portion of the guide groove 44.

Figure 9B:
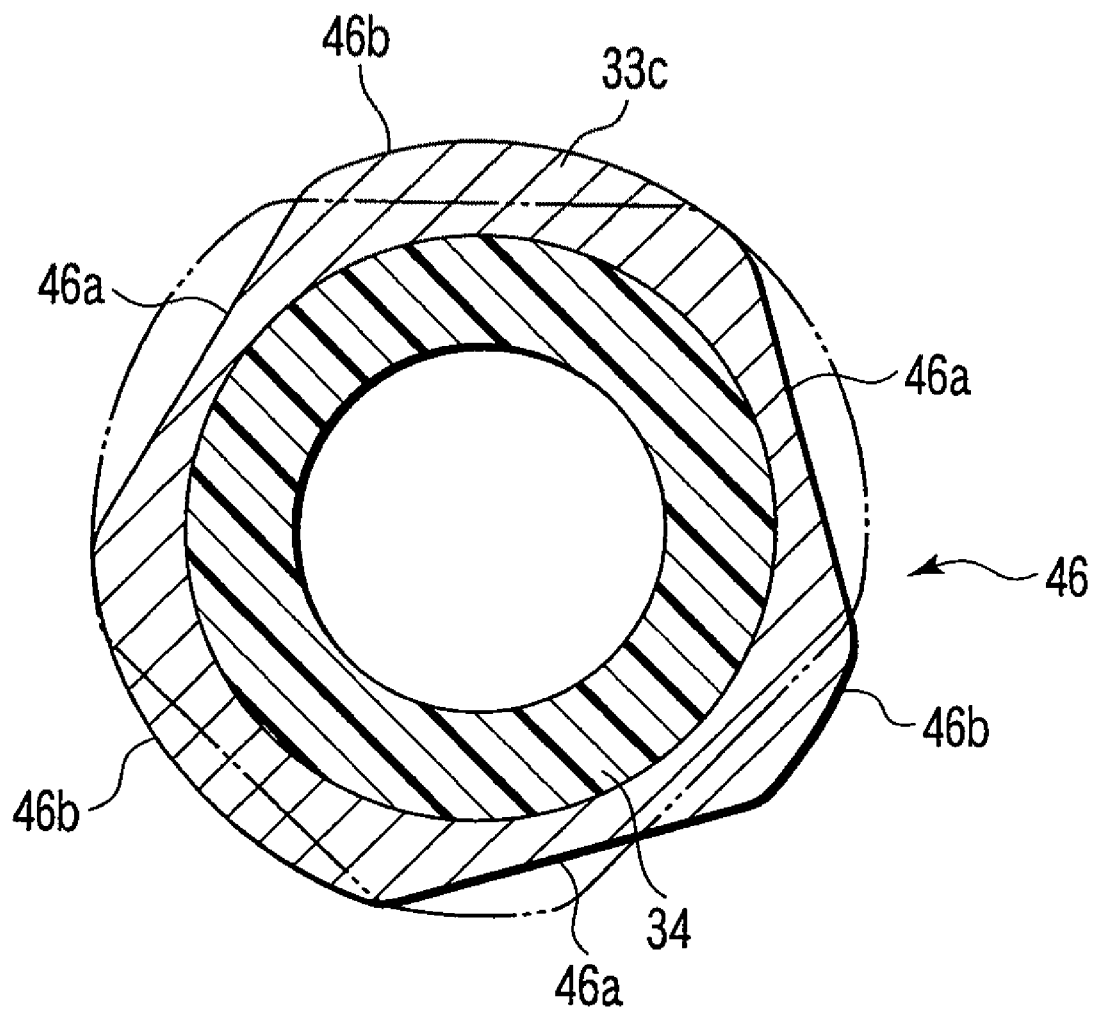
FIG. 9B is a cross-sectional view taken along line IXB-IXB in FIG. 9A.

As shown in FIG. 9B, the connection flange portion 33c of the guide cylindrical body 33 has a non-circular engaging portion 46. The engaging portion 46 has three cut-out flat-surface portions 46a at a plurality of locations on the circular outer peripheral surface of the connection flange portion 33c, for example, at three locations in this embodiment. Corner portions 46b, each having a greater diameter than the flat-surface portion 46a, are formed at connection parts between the three flat-surface portions 46. Thereby, the engaging portion 46 with a substantially triangular cross section is formed on the connection flange portion 33c. It is not necessary that the non-circular engaging portion 46 have a substantially triangular shape. The non-circular engaging portion 46 may have any other non-circular shape, for instance, a polygon such as a rectangle or a pentagon.

Figure 3:
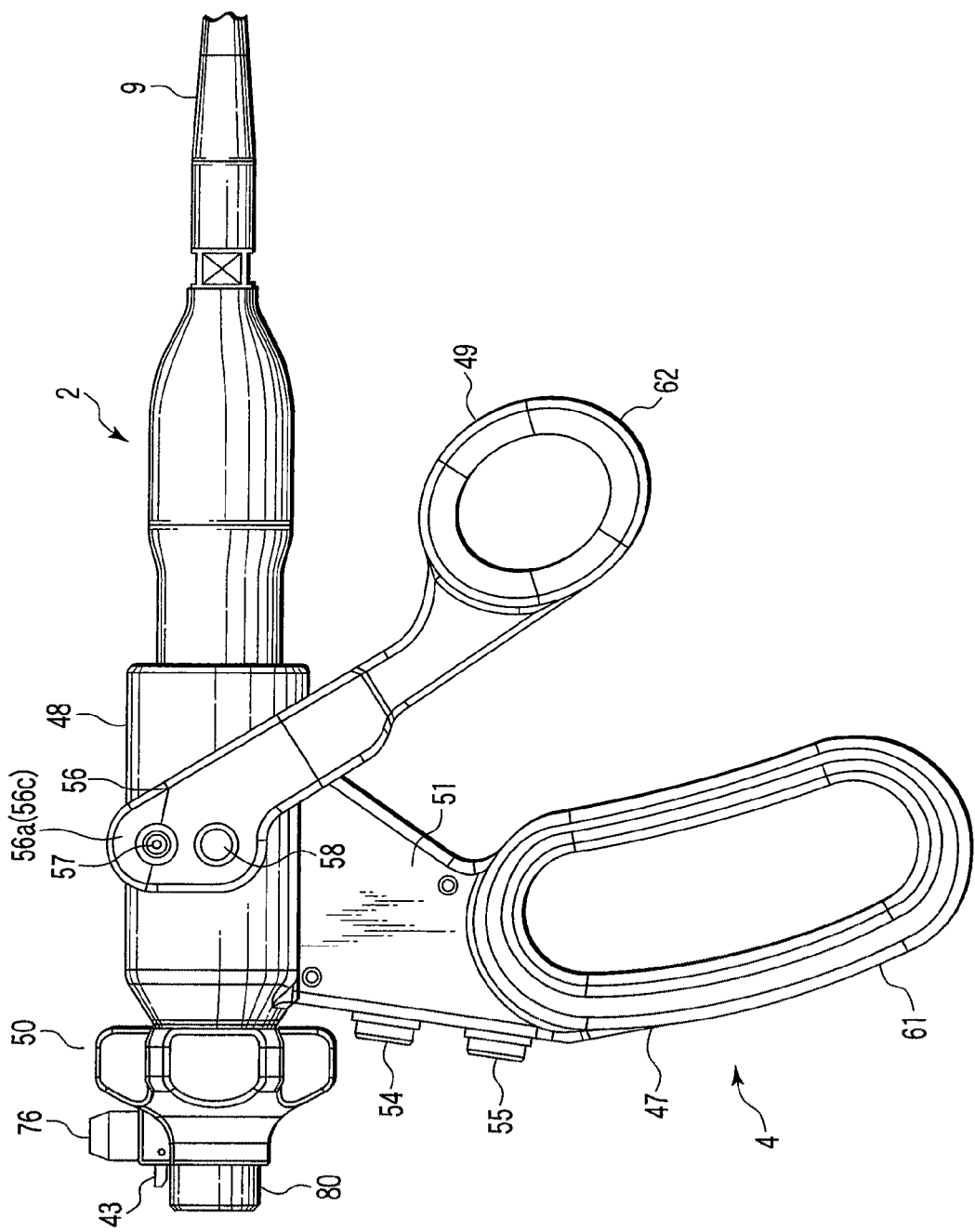
FIG. 3 is a side view showing a coupled state between a handle unit and a transducer unit of the ultrasonic therapeutic apparatus according to the first embodiment.
Figure 36:
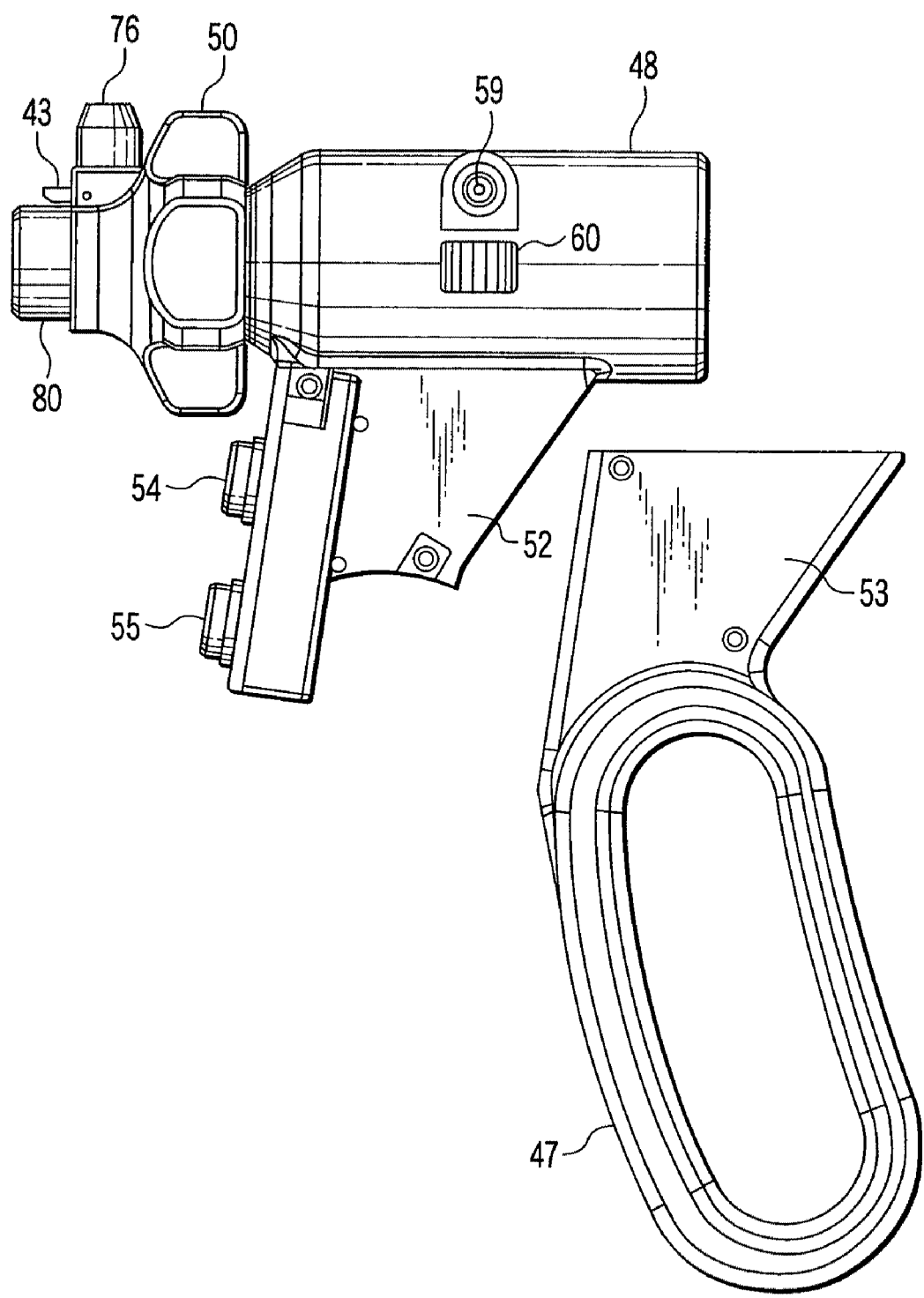
FIG. 36 is a side view showing a state before an attachment member is attached to a base member of a stationary handle of the handle unit of the ultrasonic therapeutic apparatus according to the first embodiment.

As shown in FIG. 3, the handle unit 4 mainly includes a stationary handle 47, a hold cylinder 48, a movable handle 49 and a rotational operation knob 50. The hold cylinder 48 is provided on the upper part of the stationary handle 47. A switch hold section 51 is provided between the stationary handle 47 and the hold cylinder 48. As shown in FIG. 36, the switch hold section 51 includes a switch attachment section 52 which is fixed to a lower end portion of the hold cylinder 48, and a cover member 53 which is fixed to an upper end portion of the stationary handle 47.

As shown in FIG. 37, the switch attachment section 52 has a switch attachment surface 52a on a front side thereof, to which a plurality of hand switches, for example, two hand switches (first switch 54 and second switch 55) in the present embodiment, are attached. The first switch 54 and second switch 55 are switches for selecting therapeutic functions of the therapeutic section 1A of the handpiece 1.

In the switch attachment section 52, the first switch 54 and second switch 55 are arranged in the up-and-down direction. The first switch 54 is disposed on an upper side of the switch attachment surface 52a, and is set to be a switch which selects a first therapeutic function that is frequently used among the plural therapeutic functions. The second switch 55 is disposed on a lower side of the switch attachment surface 52a, and is set to be a switch which selects another second therapeutic function of the plural therapeutic functions.

As shown in FIG. 2, the movable handle 49 has a substantially U-shaped arm section 56 at an upper part thereof. The U-shaped arm section 56 includes two arms 56a and 56b. The movable handle 49 is assembled to the hold cylinder 48 in the state in which the hold cylinder 48 is inserted between the two arms 56a and 56b.

Each of the arms 56a and 56b has a support pin 57 and an operation pin 58. As shown in FIG. 36, a pin receiving hole portion 59 and a window portion 60 are formed in each of both side portions of the hold cylinder 48. The support pin 57 of each arm 56a, 56b is inserted in the pin receiving hole portion 59 of the hold cylinder 48. Thereby, an upper end portion of the movable handle 49 is rotatably supported on the hold cylinder 48 via the support pins 57.

Ring-shaped finger hook portions 61 and 62 are provided on lower end portions of the stationary handle 47 and movable handle 49, respectively. By hooking the fingers on the finger hook portions 61 and 62 and holding them, the movable handle 49 rotates via the support pins 57 and the movable handle 49 is opened/closed relative to the stationary handle 47.

The operation pins 58 of the movable handle 49 extend into the hold cylinder 48 through the window portions 60 of the hold cylinder 48. An operation force transmission mechanism 63, which transmits an operation force of the movable handle 49 to the driving pipe 19 of the jaw 17, is provided inside the hold cylinder 48.

As shown in FIG. 37, the operation force transmission mechanism 63 mainly comprises a metallic cylindrical spring receiving member 64 and a resin-made slider member 65. The spring receiving member 64 is disposed coaxially with the center axis of the hold cylinder 48, and extends in the same direction as the direction of insertion of the probe unit 3.

A coil spring 67, the slider member 65, a stopper 68 and a spring receiver 69 are provided on an outer peripheral surface of the spring receiving member 64. A front end portion of the coil spring 67 is fixed to the spring receiver 69. The stopper 68 restricts the position of movement of a rear end side of the slider member 65. The coil spring 67 is disposed between the spring receiver 69 and the slider member 65 with a fixed amount of mounting force.

Figure 38:
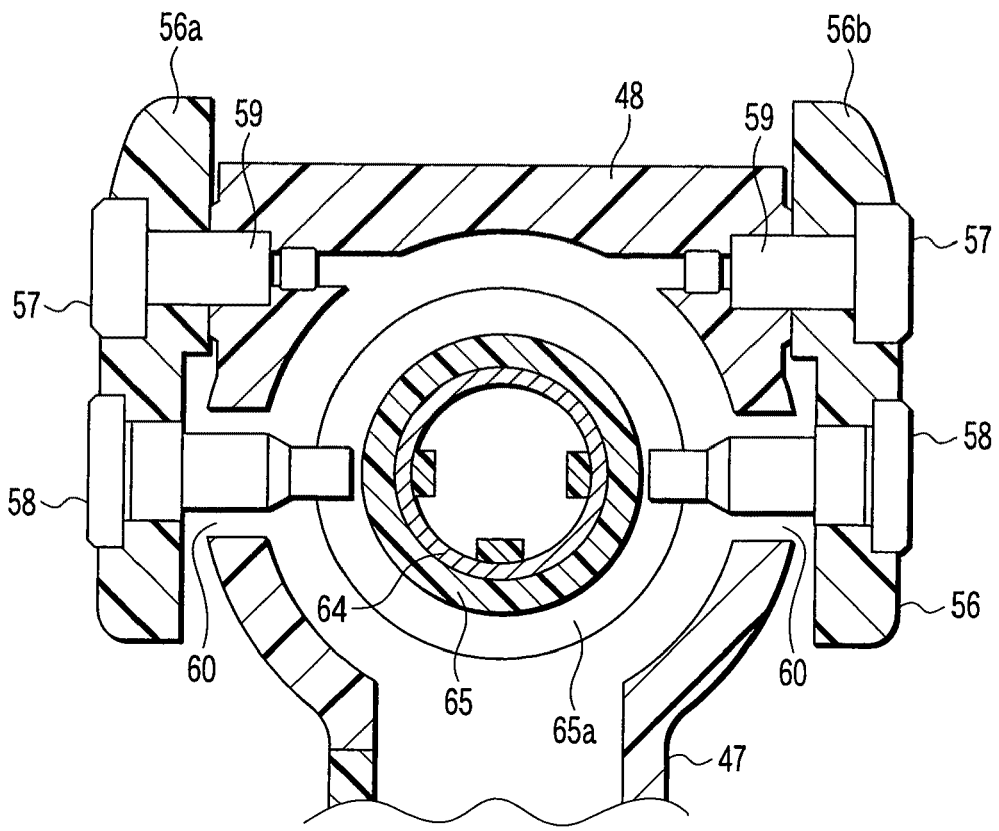
FIG. 38 is a cross-sectional view taken along line 38-38 in FIG. 37.
Figure 40:
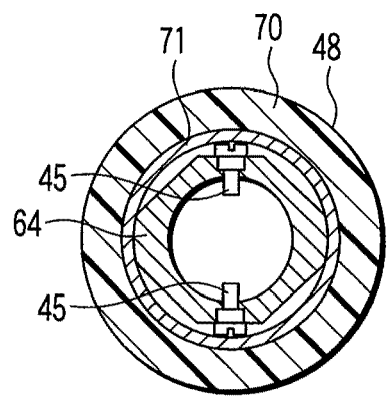
FIG. 40 is a cross-sectional view taken along line 40-40 in FIG. 37.

An annular engaging groove 65a is formed in a circumferential direction in an outer peripheral surface of the slider member 65. As shown in FIG. 38, the operation pins 58 of the movable handle 49 are inserted and engaged in the engaging groove 65a. If the movable handle 49 is held and the movable handle 49 is closed relative to the stationary handle 47, the operation pins 58 rotate about the support pins 57 in accordance with the rotational operation of the movable handle 49 at this time. The slider member 65, which is in interlock with the rotation of the support pins 57, moves forward in the axial direction. At this time, the spring receiving member 64, which is coupled to the slider member 65 via the coil spring 67, moves forward/backward together with the slider member 65. As shown in FIG. 40, a pair of engaging pins 45, which are used when the sheath unit 5 and the handle unit 4 are attached/detached, are fixed to a distal end portion of the spring receiving member 64. Thereby, the operation force of the movable handle 49 is transmitted to the connection tube body 34 of the sheath unit 5 via the pair of engaging pins 45, and the driving pipe 19 of the jaw 17 moves forward. Thereby, the jaw body 201 of the jaw 17 rotates via the support pin 27.

Further, when a living body tissue is clamped between the hold member 202 of the jaw 17 and the probe distal end portion 3a of the probe unit 3 by this operation, the hold member 202 rotates over a certain angle about the pin 214 in accordance with the bending of the probe distal end portion 3a so that force uniformly acts over the entire length of the hold member 202. In this state, ultrasonic is output and a living body tissue, such as a blood vessel, can be coagulated or cut.

An annular bearing portion 70 is formed at a front end portion of the hold cylinder 48. The bearing portion 70 is metallic, and a cylindrical rotation transmission member 71 is coupled to the bearing portion 70 rotatably about the axis. The rotation transmission member 71 includes a projecting portion 72 which projects forward of the bearing portion 70, and a large-diameter portion 73 which extends to the inner side of the hold cylinder 48 from the bearing portion 70.

The rotational operation knob 50 is fitted and fixed on the projecting portion 72. The engaging lever 43 is provided at the front end portion of the rotational operation knob 50. An intermediate portion of the engaging lever 43 is rotatably coupled to the projecting portion 72 via a pin 74. A proximal end portion of the engaging lever 43 extends to the inside of a lever receiving recess portion 75 which is formed in a front surface of the rotational operation knob 50.

An operation button 76 for operating the engaging lever 43 in such a direction as to disengage the engaging lever 43 is provided on an outer peripheral surface of the front end portion of the rotational operation knob 50. An operation pin 77, which is disposed downward, is provided so as to project from the operation button 76. The operation pin 77 extends to the inside of the lever receiving recess portion 75 through a wall hole of the rotational operation knob 50. A proximal end portion of the engaging lever 43 is rotatably coupled to a lower end portion of the operation pin 77 via a pin 78.

A removal prevention ring 80 for the rotational operation knob 50 is provided on a distal end portion of the projecting portion 72. A male threaded portion 79 is formed on the distal end portion of the projecting portion 72. A female threaded portion 80a, which is to be meshed with the male threaded portion 79, is formed on an inner peripheral surface of the removal prevention ring 80. The female threaded portion 80a of the removal prevention ring 80 is meshed and engaged with the male threaded portion 79 of the projecting portion 72, and thereby the rotational operation knob 50 is fixed to the rotation transmission member 71.

Figure 39:
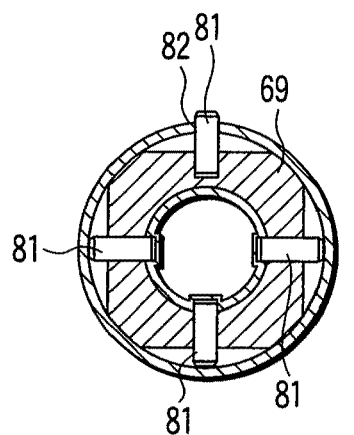
FIG. 39 is a cross-sectional view taken along line 39-39 in FIG. 37.

As shown in FIG. 39, the spring receiver 69 of the spring receiving member 64 is provided with four metallic positioning pins 81 which project radially outward. An elongated engaging hole portion 82, in which one pin 81 of the spring receiving member 64 is inserted, is formed in the large-diameter portion 73 of the rotation transmission member 71. The engaging hole portion 82 extends in the same direction as the direction of insertion of the probe unit 3. Thereby, when the movable handle 49 is operated, the pin 81 is moved along the engaging hole portion 82 and thus the advancing/retreating movement of the spring receiving member 64 is prevented from being transmitted to the rotation transmission member 71.

On the other hand, when the rotational operation knob 50 is rotated, the rotational movement of the rotation transmission member 71, which rotates together with the rotational operation knob 50, is transmitted to the spring receiving member 64 via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob as one body about the axis thereof.

Engaging means 94, which is disengageably engaged with the connection flange portion 33c of the sheath unit 5, is provided on the inner peripheral surface of the rotation transmission member 71. FIGS. 41A and 41B show the engaging means 94. The engaging means 94 includes an insertion hole portion 94a in which the connection flange portion 33c is inserted when the sheath unit 5 and handle unit 4 are coupled, and an electrically conductive rubber ring (urging means) 94b which is disposed within the insertion hole portion 94a.

The shape of the inner peripheral surface of the electrically conductive rubber ring 94b is substantially the same as the shape of the engaging portion 46 of the connection flange portion 33c. Specifically, the inner peripheral surface of the electrically conductive rubber ring 94b has three cut-out flat-surface portions 94b1 at a plurality of locations on the circular outer peripheral surface, for example, at three locations in this embodiment, and three corner portions 94b2 which are located at connection parts between the three flat-surface portions 94b1 and have greater diameters than the flat-surface portions 94b1. Thereby, the electrically conductive rubber ring 94b has a substantially triangular cross-sectional shape. Thus, as shown in FIG. 41A, the electrically conductive rubber ring 94b is held in a natural, non-compressed position in the positional state in which the inner peripheral surface shape of the electrically conductive rubber ring 94b corresponds to the engaging portion 46 of the connection flange portion 33c, that is, in the state in which the three corner portions 46b of the connection flange portion 33c correspond in position to the three corner portions 94b2 of the electrically conductive rubber ring 94b. On the other hand, by rotating the handle unit 4 and the sheath unit 5 relative to each other about the center axis of the sheath unit 5, the position of the electrically conductive rubber ring 94b is switched to a pressure contact position, as shown in FIG. 41B, where the electrically conductive rubber ring 94b is pressed on the three corner portions 46b of the connection flange portion 33c. At this time, the three corner portions 46b of the connection flange portion 33c are put in contact with, and pressed by, the three flat-surface portions 94b1 of the electrically conductive rubber ring 94b.

In the present embodiment, at the time of coupling the sheath unit 5 and handle unit 4, when the connection flange portion 33c of the sheath unit 5 is inserted straight into the electrically conductive rubber ring 94b (see FIG. 29 and FIG. 30), the electrically rubber ring 94b is held in the natural, non-compressed position, as shown in FIG. 41A. At this time, the engaging lever 43 on the handle unit 4 side is held in the state in which the engaging lever 43 rests on the inclined surface of the guide groove 41 of the handle member 32 of the sheath unit 5. Subsequently, the handle member 32 of the sheath unit 5 is rotated about the axis, relative to the handle unit 4. Thereby, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94b is switched to the pressure contact position where the electrically conductive rubber ring 94b is put in pressure contact with the three corner portions 46b of the connection flange portion 33c. Thereby, a sheath-unit-side electric path 40 (formed between the guide cylindrical body 33, fixing screw 39, coupling pipe 38, sheath 18, distal end cover 25, support pin 27 and jaw body 28) and a handle-unit-side electric path 95 (formed between an electrical contact member 96, spring receiving member 64, positioning pin 81 and rotation transmission member 71) are electrically connected via the electrically conductive rubber ring 94b. In this case, a second high-frequency electric path 97, which transmits a high-frequency current, is formed in the coupled body of the sheath unit 5 and handle unit 4.

Figure 42:
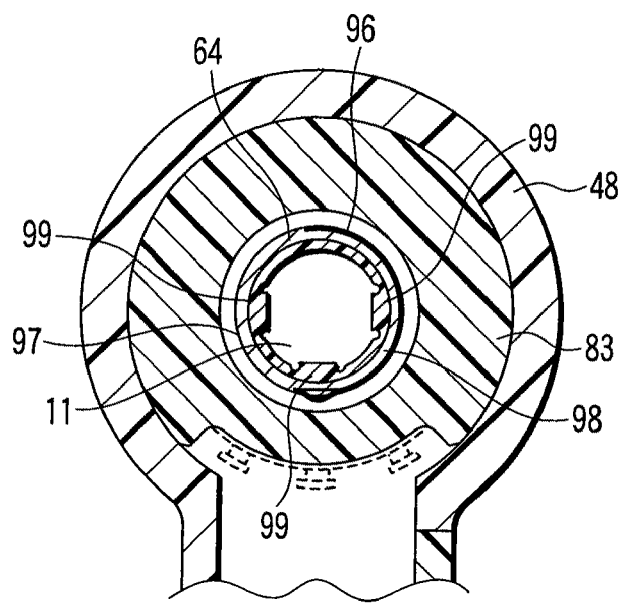
FIG. 42 is a cross-sectional view taken along line 42-42 in FIG. 37.

As shown in FIG. 42, the handle unit 4 includes a tubular member 98 which is formed of an insulating material on the inner peripheral surface of the spring receiving member 64. The tubular member 98 is fixed on the inner peripheral surface of the spring receiving member 64. Thereby, when the probe unit 3 and the handle unit 4 are connected, the first high-frequency electric path 13 and the second high-frequency electric path 97 are insulated by the tubular member 98.

An inner peripheral surface of the tubular member 98 has three engaging projection portions 99 which correspond to the three engaging recess portions 15 (see FIG. 6) of the flange portion 14 of the probe unit 3. When the probe unit 3 and handle unit 4 are connected, the three engaging projection portions 99 of the tubular member 98 are disengageably engaged with the three engaging recess portions 15 of the flange portion 14 of the probe unit 3. Thereby, the rotational-directional position between the probe unit 3 and the tubular member 98 of the handle unit 4 is restricted. Hence, when the rotational operation knob 50 is rotated, the coupled body of the probe unit 3 and transducer unit 2 is rotated as one body together with the assembly unit within the hold cylinder 48.

The engaging section between the flange portion 14 of the probe unit 3 and the tubular member 98 is not limited to the above-described structure. For example, the tubular member 98 may be formed to have a D-shaped cross section, and the flange portion 14 of the probe unit 3 may be formed to have a corresponding D-shaped cross section.

Figure 43:
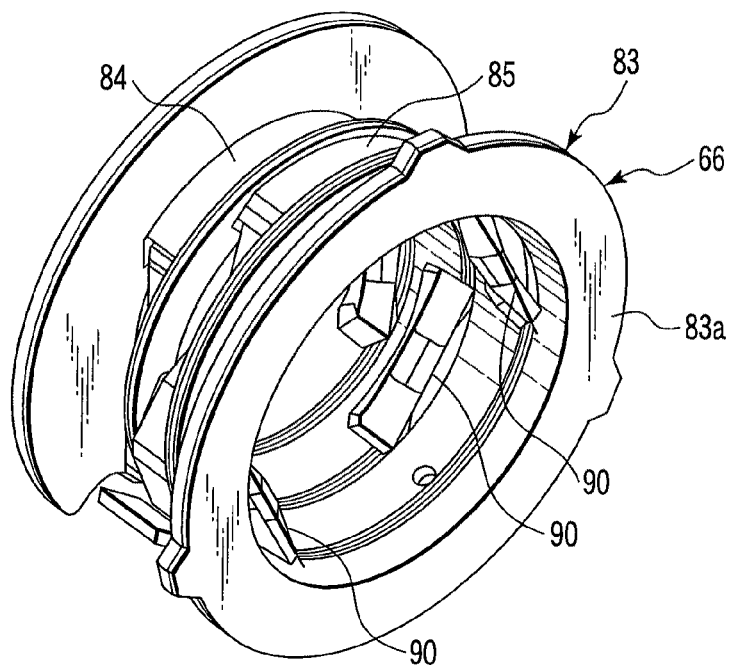
FIG. 43 is a perspective view showing an electrode hold member of the ultrasonic therapeutic apparatus according to the first embodiment.
Figure 44:
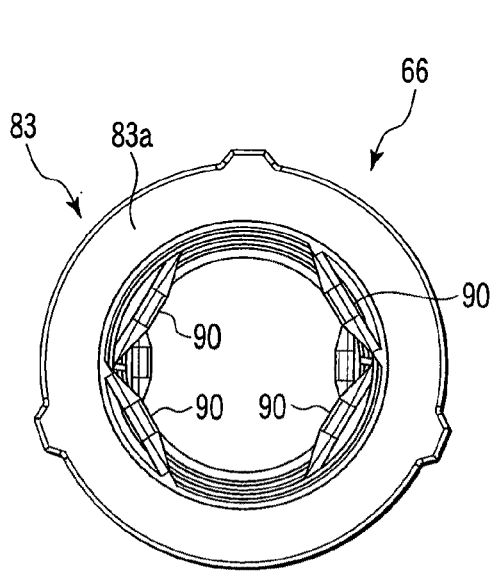
FIG. 44 is a front view showing the electrode hold member of the ultrasonic therapeutic apparatus according to the first embodiment.
Figure 45:
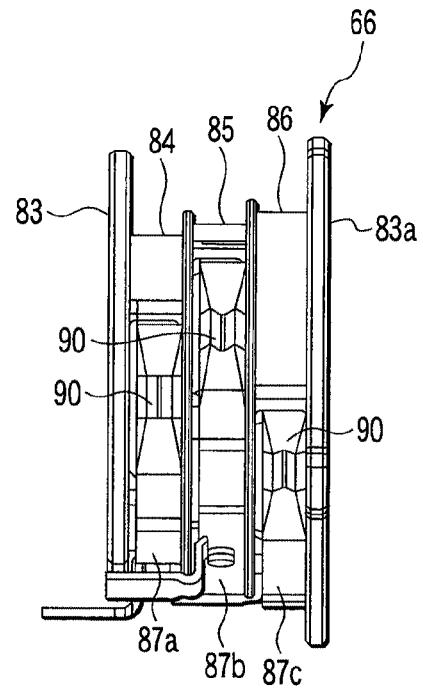
FIG. 45 is a side view showing the electrode hold member of the ultrasonic therapeutic apparatus according to the first embodiment.

FIGS. 43 to 45 show a cylindrical contact-point unit 66 which is assembled to the hold cylinder 48. The contact-point unit 66 includes a cylindrical electrode hold member 83 which is formed of a resin. As shown in FIG. 45, the electrode hold member 83 includes three (first to third) electrode receiving sections 84, 85 and 86 with different outside diameters. The first electrode receiving section 84 on the distal end side has a smallest diameter, and the third electrode receiving section 86 on the rear end side has a greatest diameter.

Figure 48:
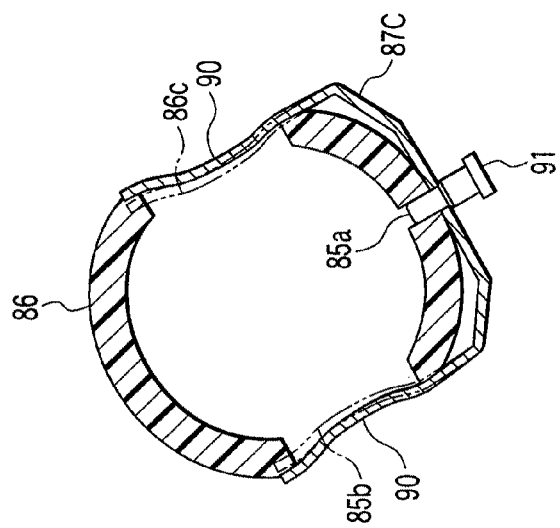
FIG. 48 is a cross-sectional view taken along line 48-48 in FIG. 37.
Figure 47:
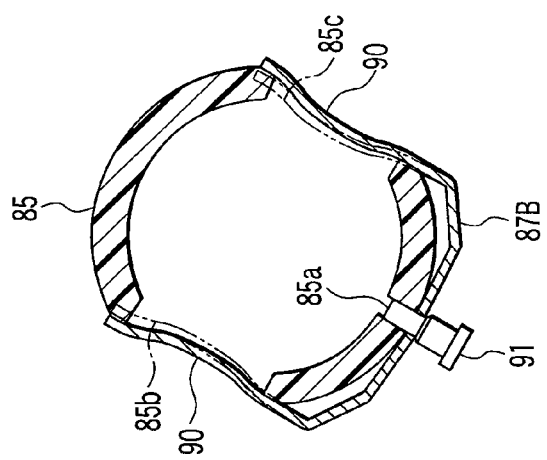
FIG. 47 is a cross-sectional view taken along line 47-47 in FIG. 37.
Figure 46:
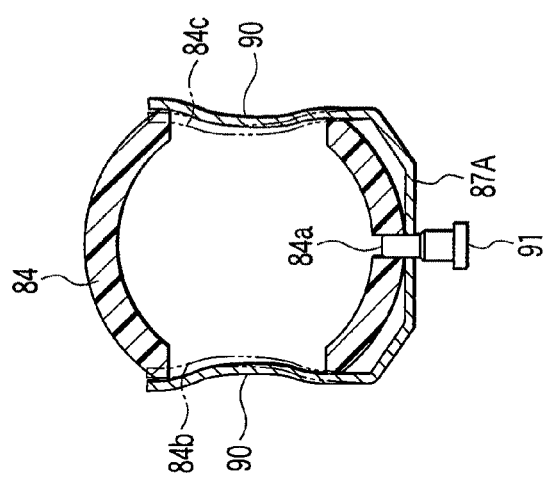
FIG. 46 is a cross-sectional view taken along line 46-46 in FIG. 37.

FIG. 46 shows the first electrode receiving section 84, FIG. 47 shows the second electrode receiving section 85, and FIG. 48 shows the third electrode receiving section 86.

As shown in FIG. 46, the first electrode receiving section 84 has one contact-point member fixing hole 84a, and two through-holes 84b and 84c. A center line of the two through-holes 84b and 84c is set to be perpendicular to a center line of the contact-point member fixing hole 84a.

Similarly, as shown in FIG. 47, the second electrode receiving section 85 has one contact-point member fixing hole 85a, and two through-holes 85b and 85c. As shown in FIG. 48, the third electrode receiving section 86 has one contact-point member fixing hole 86a, and two through-holes 86b and 86c.

The positions of the contact-point member fixing hole 84a of the first electrode receiving section 84, the contact-point member fixing hole 85a of the second electrode receiving section 85 and the contact-point member fixing hole 86a of the third electrode receiving section 86 are displaced in the circumferential direction of the electrode hold member 83.

FIG. 49 and FIG. 50 show electrode members 87A, 87B and 87C which are assembled to the first to third electrode receiving sections 84, 85 and 86. These electrode members 87A, 87B and 87C are formed in the same shape. In the description below, only the electrode member 87A, which is assembled to the first electrode receiving section 84, is described. The common parts of the electrode members 87B and 87C of the other second and third electrode receiving sections 85 and 86 are denoted by like reference numerals, and a description thereof is omitted.

The electrode member 87A includes one straight stationary portion 87a and two bend portions 87b and 87C. One bend portion 87b is disposed at one end of the straight stationary portion 87a, and the other bend portion 87c is disposed at the other end of the straight stationary portion 87a. Thereby, as shown in FIG. 49, the electrode member 87A is formed and bent in a substantially U shape.

A hole 88 and an L-shaped wiring connection portion 89 are provided at a central position of the stationary portion 87a. Inwardly curved waist portions 90 are formed at central positions of the two bend portions 87b and 87c.

When the first electrode receiving section 84 and the electrode member 87A are assembled, a fixing pin 91 is inserted in the hole 88 of the stationary portion 87a of the electrode member 87A and in the contact-point member fixing hole 84a of the first electrode receiving section 84. The electrode member 87A is fixed to the first electrode receiving section 84 by the fixing pin 91. At this time, the waist portion 90 of one bend portion 87b of the electrode member 87A is disposed in one through-hole 84b of the first electrode receiving section 84, and the waist portion 90 of the other bend portion 87c of the electrode member 87A is disposed in the other through-hole 84c. The same applies when the electrode member 87B is assembled to the second electrode receiving section 85 and the electrode member 87C is assembled to the third electrode receiving section 86.

Figure 51:
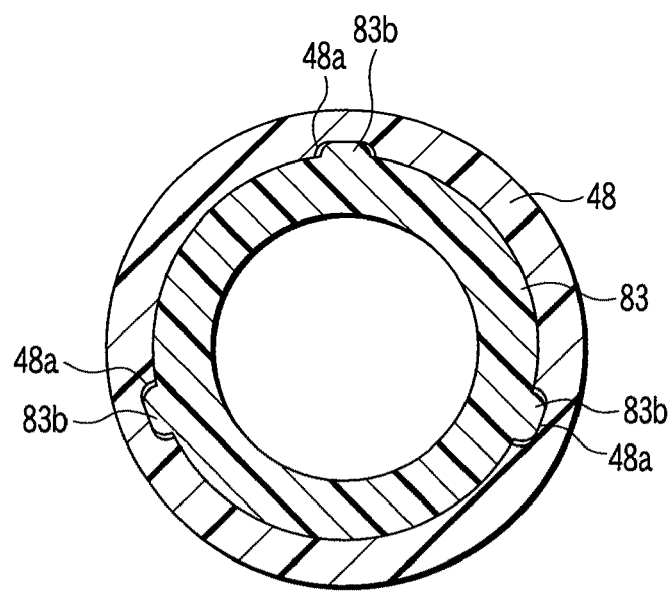
FIG. 51 is a cross-sectional view taken along line 51-51 in FIG. 37.

As shown in FIG. 51, a large-diameter fixing flange portion 83a is formed at a rear end portion of the electrode hold member 83 of the contact-point unit 66. Engaging projection portions 83b are provided to project from the outer peripheral surface of the fixing flange portion 83a at a plurality of locations, for example, at three locations in this embodiment. Engaging recess portions 48a are formed in an inner peripheral surface of the rear end portion of the hold cylinder 48 at positions corresponding to the three engaging projection portions 83b of the stationary flange portion 83a. In the case where the electrode hold member 83 is assembled in the hold cylinder 48, the three engaging projection portions 83b of the stationary flange portion 83a are inserted, engaged and fixed in the engaging recess portions 48a of the hold cylinder 48. Thereby, the rotation of the electrode hold member 83 about the axis thereof, relative to the hold cylinder 48, is restricted.

A stepped portion 43b, which comes in contact with the fixing flange portion 83a of the electrode hold member 83, is formed on the hold cylinder 48. The electrode hold member 83 is fixed to the hold cylinder 48 by a fixing screw 48c in the state in which the fixing flange portion 83a of the electrode hold member 83 abuts upon the stepped portion 43b. Thereby, the axial movement of the electrode hold member 83, relative to the hold cylinder 48, is restricted.

End portions of three wiring lines 93a to 93c, which are assembled in the switch hold section 51, are connected to the wiring connection portions 89 of the three electrode members 87A, 87B and 87C that are assembled to the contact-point unit 66.

Further, as shown in FIG. 42, the contact-point unit 66 is provided with a substantially C-shaped electric contact-point member 96 which is formed of a metallic plate spring. The electric contact-point member 96 is connected to the outer-peripheral surface of the proximal end portion of the spring receiving member 64.

The handle-unit-side electric path 95 is composed of the electrical contact member 96, spring receiving member 64, positioning pin 81 and rotation transmission member 71.

A front end portion of the transducer unit 2 is detachably coupled to the contact-point unit 66. As shown in FIG. 52, two wiring lines 101 and 102 for the ultrasonic transducer, two wiring lines 103 and 104 for high-frequency power and three wiring lines 105, 106 and 107, which are connected to a wiring circuit board within the switch hold section 51, are assembled in the single cable 9 at the rear end of the transducer unit 2. Distal end portions of the two wiring lines 101 and 102 for the ultrasonic transducer are connected to the ultrasonic transducer 6. A distal end portion of one wiring line 103 for high-frequency power is connected to the ultrasonic transducer 6.

First to fourth electrically conductive plates 111 to 114 for electric connection are provided at the rear end of the transducer unit 2. A distal end portion of the other wiring line 104 for high-frequency power is connected to the first conductive plate 111. The three wiring lines 105, 106 and 107 are connected to the second to fourth conductive plates 112 to 114.

FIG. 4 shows the internal structure of a front end portion of the transducer unit 2. A connection cylindrical portion 121 is formed at the distal end portion of the transducer cover 7. A C-ring 122 having a partly cut-out annular plate shape is mounted on the outer peripheral surface of the connection cylindrical body 121. Three (first to third) cylindrical portions 123 to 125 with different outside diameters are projectingly provided on the inside of the connection cylindrical portion 121. The first cylindrical portion 123 has a smallest outside diameter and has a greatest length of projection from the distal end of the connection cylindrical body 121. The second cylindrical portion 124 has an outside diameter, which is greater than the outside diameter of the first cylindrical portion 123, and has a length of projection from the distal end of the connection cylindrical body 121, which is less than the length of projection of the first cylindrical portion 123. The third cylindrical portion 125 has a greatest outside diameter and has a length of projection from the distal end of the connection cylindrical body 121, which is less than the length of projection of the second cylindrical portion 124.

A first cylindrical contact-point member 131 is mounted on the outer peripheral surface of the first cylindrical portion 123. Similarly, a second cylindrical contact-point member 132 is mounted on the outer peripheral surface of the second cylindrical portion 124, and a third cylindrical contact-point member 133 is mounted on the outer peripheral surface of the third cylindrical portion 125. The second conductive plate 112 is connected to the first contact-point member 131, the third conductive plate 113 is connected to the second contact-point member 132, and the fourth conductive plate 114 is connected to the third contact-point member 133.

A fourth contact-point member 134 is mounted on the inner peripheral surface of the first cylindrical body 123. The fourth contact-point member 134 is connected to the first conductive plate 111.

When the handle unit 4 and the transducer unit 2 are coupled, the contact-point unit 66 of the handle unit 4 and the front end portion of the transducer unit 2 are connected. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected.

Next, the operation of the present embodiment is described. The handpiece 1 of the ultrasonic therapeutic apparatus of the present embodiment, as shown in FIG. 2, comprises four units, namely, the transducer unit 2, probe unit 3, handle unit 4 and sheath unit 5, which are detachable. When the handpiece 1 is used, the transducer unit 2 and the probe unit 3 are coupled. Thereby, the first high-frequency electric path 13, which transmits a high-frequency current to the coupled body of the transducer unit 2 and probe unit 3, is formed.

Subsequently, the handle unit 4 and the sheath unit 5 are coupled. When the handle unit 4 and sheath unit 5 are coupled, the connection tube body 34 is inserted in the rotation transmission member 71 of the handle unit 4 in the state in which the handle member 32 of the sheath unit 5 is held. When the sheath unit 5 and handle unit 4 are coupled, the engaging lever 43 on the handle unit 4 side is held in the state in which the engaging lever 43 rests on the inclined surface of the guide groove 41 of the handle member 32 of the sheath unit 5, as shown in FIG. 29 and FIG. 30. At this time, as shown in FIG. 41A, the electrically conductive rubber ring 94b is held in the positional state in which the inner peripheral surface shape of the electrically conductive rubber ring 94b corresponds to the engaging portion 46 of the connection flange portion 33c, that is, in the state in which the three corner portions 46b of the connection flange portion 33c correspond in position to the three corner portions 94b2 of the electrically conductive rubber ring 94b. Accordingly, the connection flange portion 33c of the sheath unit 5 is inserted straight into the electrically conductive rubber ring 94b. At the time of this insertion operation, as shown in FIG. 41A, the conductive rubber ring 94b is held in the natural, non-compressed position. In this state, the sheath-unit-side electric path 40 and the handle-unit-side electric path 95 are not electrically connected.

Subsequently, following this insertion operation, the handle member 32 of the sheath unit 5 is rotated about the axis thereof, relative to the handle unit 4. By this operation, as shown in FIG. 31 and FIG. 32, the engaging lever 43 on the handle unit 4 side is inserted and engaged in the engaging recess portion 42 at one end portion of the guide groove 41. At this time, as shown in FIG. 41B, the electrically conductive rubber ring 94b is switched to the pressure contact position where the electrically conductive rubber ring 94b is put in pressure contact with the three corner portions 46b of the connection flange portion 33c. Thereby, the sheath-unit-side electric path 40 and the handle-unit-side electric path 95 are electrically connected via the electrically conductive rubber ring 94b. As a result, the second high-frequency electric path 97, which transmits a high-frequency current, is formed in the coupled body of the sheath unit 5 and handle unit 4.

When the sheath unit 5 is rotated about the axis thereof, the pair of engaging pins 45 on the handle unit 4 side are, at the same time, disengageably engaged in the engaging groove 44a at the terminal end portion of the guide groove 44 of the sheath unit 5. Thereby, the spring receiving member 64 on the handle unit 4 side and the connection tube body 34 on the sheath unit 5 side are coupled via the engaging pins 45. As a result, the operation force on the handle unit 4 side at the time when the movable handle 49 is closed relative to the stationary handle 47 can be transmitted to the driving pipe 19 of the jaw 17 on the sheath unit 5 side. This state is the coupled state between the sheath unit 5 and the handle unit 4.

Thereafter, the coupled body of the sheath unit 5 and handle unit 4 and the coupled body of the ultrasonic transducer 6 and probe unit 3 are assembled as one body. In this assembling work, the contact-point unit 66 of the handle unit 4 is connected to the front end portion of the transducer unit 2. At this time, the electrode member 87A of the contact-point unit 66 and the first contact-point member 131 of the transducer unit 2 are connected. At the same time, the electrode member 87B of the contact-point unit 66 and the second contact-point member 132 of the transducer unit 2 are connected, the electrode member 87C of the contact-point unit 66 and the third contact-point member 133 of the transducer unit 2 are connected, and the C-shaped electric contact-point member 96 of the contact-point unit 66 and the fourth contact-point member 134 of the transducer unit 2 are connected. Thereby, the second high-frequency electric path 97 of the coupled body of the sheath unit 5 and handle unit 4 is connected to the wiring line 104 for high-frequency power within the cable 9. Further, the three wiring lines 105, 106 and 107 within the cable 9 are connected to the wiring circuit board within the switch hold section 51. This state is the completion state of the assembly of the handpiece 1.

When the handpiece 1 is used, the movable handle 49 is opened/closed relative to the stationary handle 47. The driving pipe 19 is axially moved in interlock with the operation of the movable handle 49, and the jaw 17 is opened/closed, relative to the probe distal end portion 3a of the probe unit 3, in interlock with the advancing/retreating movement of the driving pipe 19 in its axial direction. When the movable handle 49 is closed relative to the stationary handle 47, the driving pipe 19 is pushed forward in interlock with the operation of the movable handle 49. The jaw 17 is rotated and driven (to a closed position) in a direction toward the probe distal end portion 3a of the probe unit 3 in interlock with the pushing operation of the driving pipe 19. By the rotation of the jaw 17 to its closed position, a living body tissue is held between the jaw 17 and the probe distal end portion 3a of the probe unit 3.

In this state, one of the switch button 54 for coagulation and the switch button 55 for incision, which are provided on the stationary handle 47, is selectively pressed. When the switch button 54 for coagulation is pressed, power is supplied to the first high-frequency electric path 13 for supplying a high-frequency current to the probe distal end portion 3a of the probe unit 3 and to the second high-frequency electric path 97 for supplying a high-frequency current to the jaw body 28 of the sheath unit 5. Thereby, the two bipolar electrodes for high-frequency therapeutic treatment are constituted by the probe distal end portion 3a of the probe unit 3 and the jaw body 28 of the sheath unit 5. By supplying a high-frequency current between the two bipolar electrodes which are constituted by the probe distal end portion 3a of the probe unit 3 and the jaw body 28 of the sheath unit 5, bipolar high-frequency therapeutic treatment can be performed for the living body tissue between the jaw 17 and the probe distal end portion 3a of the probe unit 3.

When the switch button 55 for incision is pressed, a driving current is supplied to the ultrasonic transducer 6 at the same time as the supply of high-frequency current, and the ultrasonic transducer 6 is driven. At this time, ultrasonic vibration from the ultrasonic transducer 6 is transmitted to the probe distal end portion 3a via the vibration transmission member 11. Thereby, incision, resection, etc. of the living body tissue can be performed by making use of ultrasonic at the same time as the supply of high-frequency current. In the meantime, coagulation for the living body tissue can be performed by using ultrasonic.

When the movable handle 49 is opened relative to the stationary handle 47, the driving pipe 19 is pulled to the proximal side in interlock with the opening operation of the removable handle 49. The jaw 17 is driven (to an open position) in a direction away from the probe distal end portion 3a of the probe unit 3 in interlock with the pulling operation of the driving pipe 19.

When the rotational operation knob 50 is rotated, the rotational movement of the rotation transmission member 71, which rotates together with the rotational operation knob 50, is transmitted to the spring receiving member 64 side via the pin 81. Thereby, when the rotational operation knob 50 is rotated, the assembly unit of the rotation transmission member 71, pin 81, spring receiving member 64, slider member 65 and coil spring 67 within the hold cylinder 48 is rotated together with the rotational operation knob 50 as one body about the axis thereof. Further, the rotational operation force of the rotational operation knob 50 is transmitted to the vibration transmission member 11 of the probe unit 3 via the tubular member 98 that rotates together with the spring receiving member 64 within the hold cylinder 48. Thereby, the assembly unit within the hold cylinder 48 and the coupled body of the transducer unit 2 and probe unit 3 are rotated about the axis as one body.

At this time, the handle member 32 and guide cylindrical body 33 of the sheath unit 5 rotate together with the rotational operation knob 50. Furthermore, the sheath 18 rotates together with the guide cylindrical body 33, and the rotation of the guide cylindrical body 33 is transmitted to the connection tube body 34 and driving pipe 19 via the threaded pin 235. Thus, the jaw 17 and probe distal end portion 3a of the therapeutic section 1A are rotated about the axis at the same time together with the rotational operation knob 50.

The following advantageous effects can be obtained by the above-described structure. Specifically, in the handpiece 1 of the ultrasonic therapeutic apparatus according to the present embodiment, the operating section 222, which is disposed on the distal end side of the body section 221 of the driving pipe 19, is formed of the U-shaped portion 226 having the U-shaped cross section. In addition, as shown in FIG. 22, the peripheral wall of the tubular distal end portion of the body section 221 includes the crescent-shaped arcuate cross-sectional portion 224, which is formed by leaving a substantially crescent-shaped arcuate cross-sectional portion over a predetermined length in the axial direction, and cutting out the other portion. As shown in FIG. 23, the arcuate cross-sectional portion 224 includes the taper portion 225 with a tapered distal end portion, which is gradually tapered toward the distal end side. As shown in FIG. 22 and FIG. 25, the U-shaped portion 226 is formed at the distal end of the taper portion 225. Thus, there is no acute-angled part between the distal end portion of the driving pipe 19 and the operation section 222 having the connection section 223 that is connected to the jaw 17. Therefore, when the jaw 17 is opened/closed relative to the probe distal end portion 3a via the driving pipe 19 in accordance with the operation of the operation handle 49, no stress concentration occurs at the part between the distal end portion of the driving pipe 19 and the operation section 222. As a result, stress concentration on the driving pipe 19, which rotates the jaw 17, can be prevented, and the operation force of the operation handle 49 can exactly be transmitted to the jaw. Thereby, the handpiece 1 can stably be operated. Moreover, a decrease in durability of the apparatus can be prevented.

In the present embodiment, the operating section 222 has the slit 227 extending in the axial direction of the sheath 18 in the distal end portion of the connecting surface 226c. Thereby, when the jaw 17 is rotated via the coupling pin 217, which is connected to the connection section 223 of the operation section 222, in accordance with the axial advancing/retreating movement of the driving pipe 19, the surrounding of the connection part between the connection section 223 of the operation section 222 and the coupling pin 217 can be made easily deformable. Thus, the rotating operation of the jaw 17 can smoothly be performed.

Further, the slit 227 has the terminal end portion 227a which is located at the position corresponding to the proximal end portion of the inclined surface of the connecting surface 226c. Thereby, when the jaw 17 is rotated, the surrounding of the connection part between the connection section 223 of the operation section 222 and the coupling pin 217 can be made more easily deformable, and the rotating operation of the jaw 17 can smoothly be performed.

A second embodiment of the present invention will now be described with reference from FIG. 53 to FIG. 73. FIG. 53 schematically shows the entire structure of a handpiece 301 of an ultrasonic operating apparatus which is a surgical operating apparatus according to the second embodiment. The ultrasonic operating apparatus of the present embodiment is an ultrasonic coagulation/incision apparatus. This ultrasonic coagulation/incision apparatus can perform therapeutic treatment, such as incision, resection or coagulation, of a living body tissue by making use of ultrasonic, and can also perform therapeutic treatment by high-frequency waves.

Figure 54:
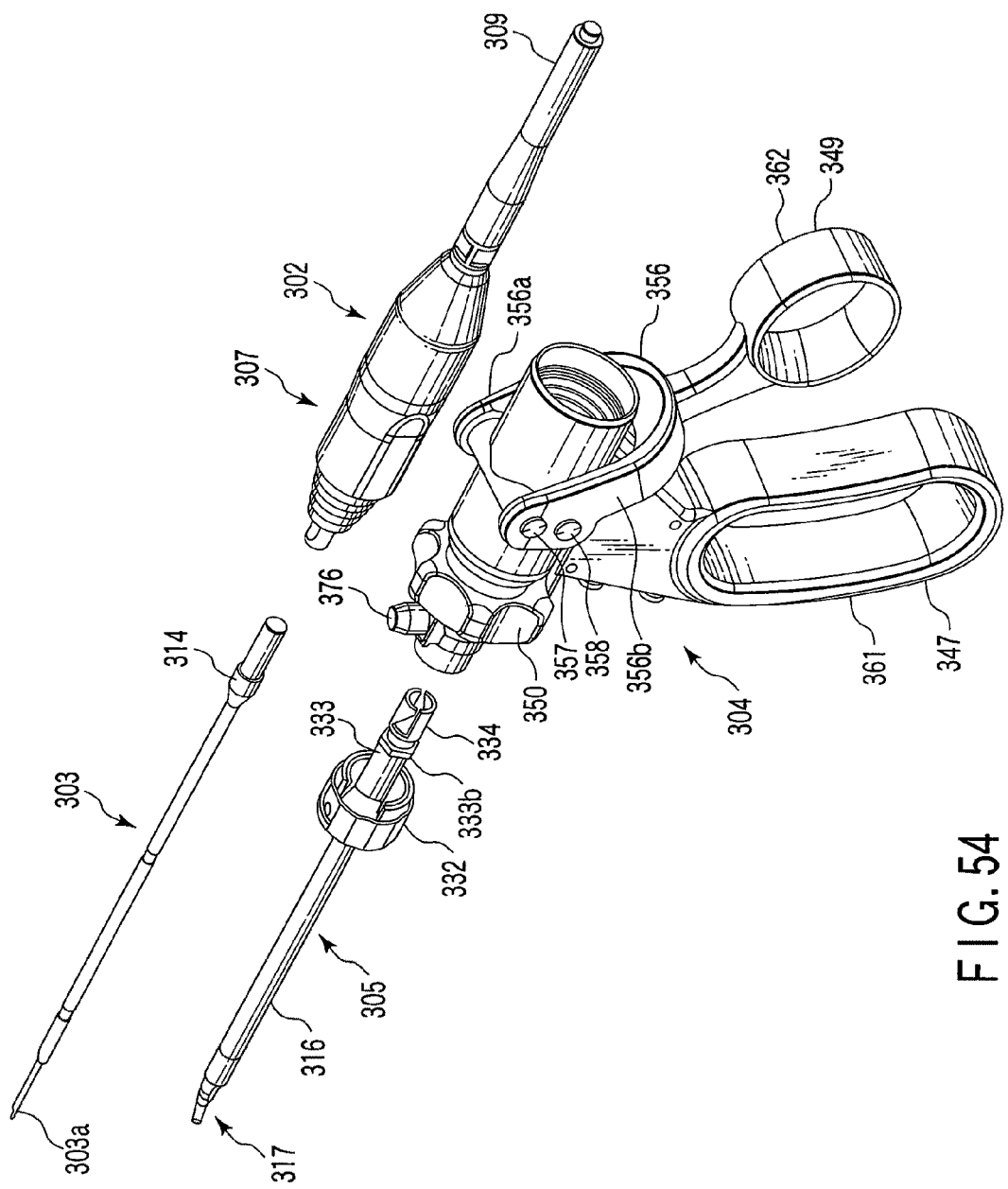
FIG. 54 is a perspective view showing a disassembled state of the surgical operating apparatus according to the second embodiment, with coupling sections of assembly units of the surgical operating apparatus being disconnected.

The handpiece 301, as shown in FIG. 54, comprises four units, namely, a transducer unit 302, a probe unit (probe section) 303, a handle unit (operation section) 304 and a sheath unit (sheath section) 305. These units are detachably coupled.

As shown in FIG. 56, an ultrasonic transducer 306 for generating ultrasonic vibration by a piezoelectric element, which converts an electric current to ultrasonic vibration, is built in the transducer unit 302. An outside of the ultrasonic transducer 306 is covered with a cylindrical transducer cover 307. As shown in FIG. 53, a cable 309, for supplying an electric current for generating ultrasonic vibration from a power supply device body 308, extends from a rear end of the transducer unit 302.

A proximal end portion of a horn 310, which increases the amplitude of ultrasonic vibration, is coupled to a front end portion of the ultrasonic transducer 306. A screw hole portion 310a for attachment of the probe is formed at a distal end portion of the horn 310.

Figure 57:
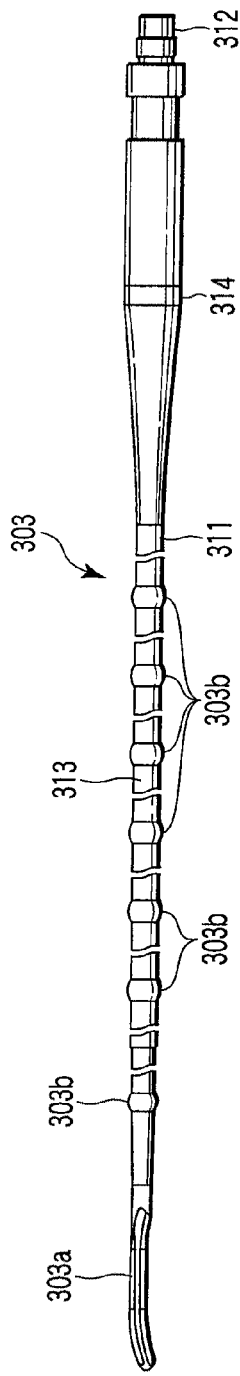
FIG. 57 is a plan view showing a probe unit of the surgical operating apparatus according to the second embodiment.

FIG. 57 shows the external appearance of the entire probe unit 303. The probe unit 303 is designed such that the entire length thereof may become an integer number of times of half-wave length of the ultrasonic vibration. The probe unit 303 has a distal end portion and a proximal end portion, and includes a metallic rod-shaped vibration transmission member 311 having a long axis. A proximal end portion of the vibration transmission member 311 is provided with a screw portion 312 which is to be engaged with the screw hole portion 310a of the horn 310. The screw portion 312 is engaged with the screw hole portion 310a of the horn 310 of the transducer unit 302. Thereby, the probe unit 303 and the transducer unit 302 are assembled. At this time, a first high-frequency electric path 313, through which a high-frequency current is transmitted, is formed in the coupled body of the ultrasonic transducer 306 and the probe unit 303.

A probe distal end portion 303a is provided at a distal end portion of the vibration transmission member 311. A first hold member is formed by the probe distal end portion 303a. The probe distal end portion 303a is formed in a substantially J-shaped curved form. The probe distal end portion 303a constitutes a first electrode section which is one of bipolar electrodes. The cross-sectional area of the probe unit 303 is decreased in the axial direction at several nodes of vibration in the axial direction, so that an amplitude necessary for therapeutic treatment can be obtained at the probe distal end portion 303a. Rubber rings 303b, which are formed of elastic material in an annular shape, are attached to several positions of nodes of vibration along the axial direction of the probe unit 303. The rubber rings 303b prevent interference between the probe unit 303 and the sheath unit 305.

A flange portion 314 is provided at the position of the node of vibration on the most proximal end side in the axial direction of the probe unit 303. Engaging recess portions (not shown) each having a key groove shape are formed on the outer peripheral surface of the flange portion 314, for example, at three positions in the circumferential direction thereof.

Figure 58:
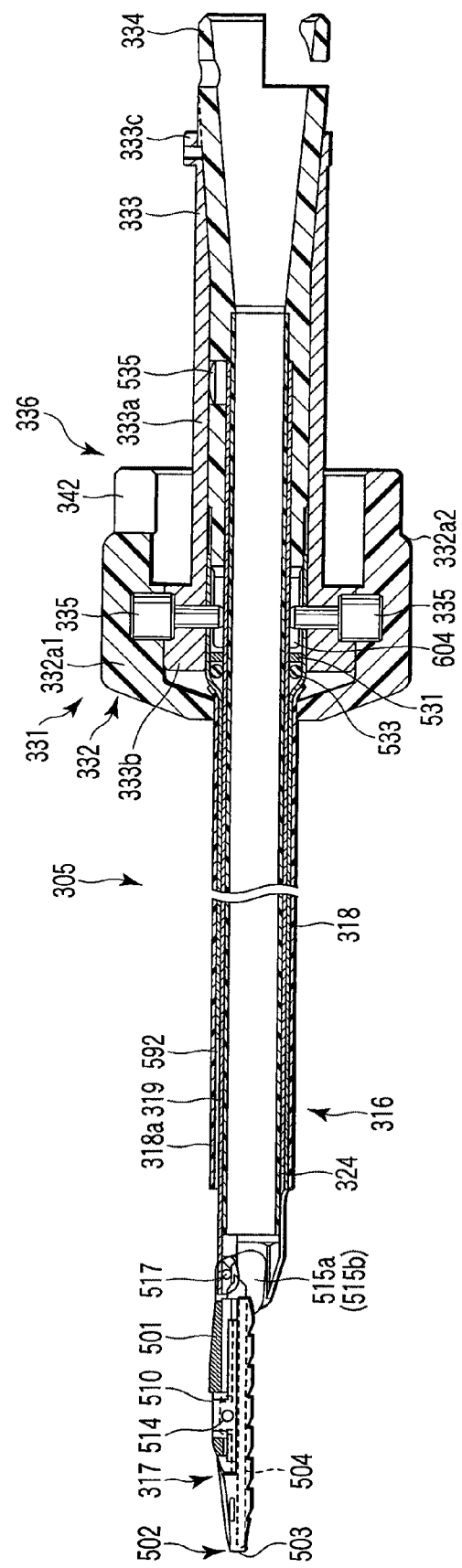
FIG. 58 is a longitudinal cross-sectional view of a sheath unit of the surgical operating apparatus according to the second embodiment.

FIG. 58 is a longitudinal cross-sectional view of the sheath unit 305. The sheath unit 305 includes a sheath body 316, which is formed of a circular cylindrical body, and a jaw 317 which is provided at a distal end of the sheath body 316. The sheath body 316 includes a metallic outer sheath 318 which is an outer cylinder, and a metallic driving pipe (driving member) 319 which is an inner cylinder (inner sheath). The driving pipe 319 is axially movably inserted in the outer sheath 318. FIGS. 59A to 59C and FIG. 60 show the driving pipe 319, and FIGS. 61A to 61D show the outer sheath 318.

The outer peripheral surface of the outer sheath 318 is covered with an outer coating 318a which is formed of an insulating material such as a resin. An insulation tube 324, which is formed of an insulating material, is provided on the inner peripheral side of the driving pipe 319.

Figure 61A:
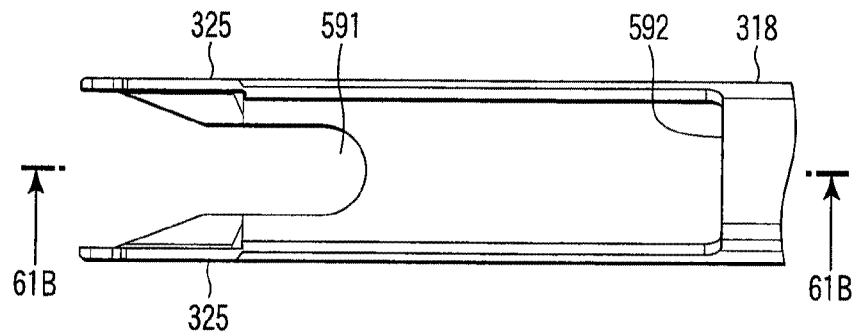
FIG. 61A is a longitudinal cross-sectional view showing a proximal end portion of an outer sheath of the sheath unit of the surgical operating apparatus according to the second embodiment.
Figures 61B, 61C:
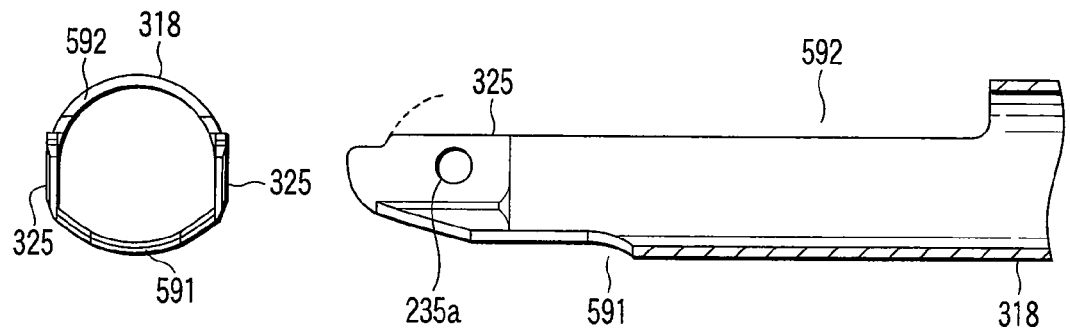
FIG. 61B is a cross-sectional view taken along line 61B-61B in FIG. 61A.
FIG. 61C is a front view showing the outer sheath shown in FIG. 61B.
Figure 61D:
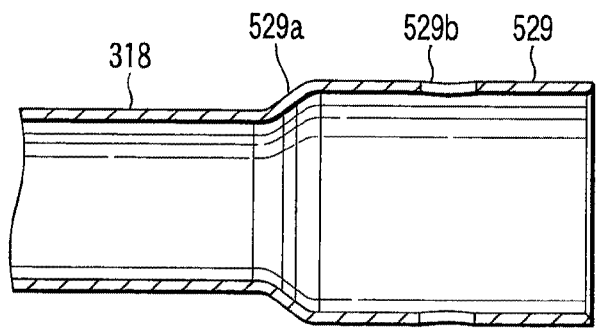
FIG. 61D is a longitudinal cross-sectional view showing a proximal end portion of the outer sheath.

As shown in FIG. 61A, a pair of left and right projection portions 325 are provided at a distal end portion of the outer sheath 318 so as to project in a forward direction of the outer sheath 318. As shown in FIG. 61B, a circular hole 325a is formed in each of the projection portions 325. A proximal end portion of the jaw 317 is rotatably attached to the circular poles 325a of the projection portions 325 via boss portions 327 (to be described later).

Further, a notch portion 592 for smoothing the movement of the driving pipe 319 is formed on an upper side (in FIG. 61B) of the distal end portion of the outer sheath 318. The notch portion 592 is formed to have a greater opening area than an opening portion 591 which is formed on a lower side (in FIG. 61B). As shown in FIG. 65, the notch portion 592 of the outer sheath 318 is covered with the outer coating 318a which is formed of an insulating material. When the probe unit 303 and the sheath unit 305 are assembled, the jaw 317 is positioned to be opposed to the probe distal end portion 303a of the probe unit 303.

Figure 67:
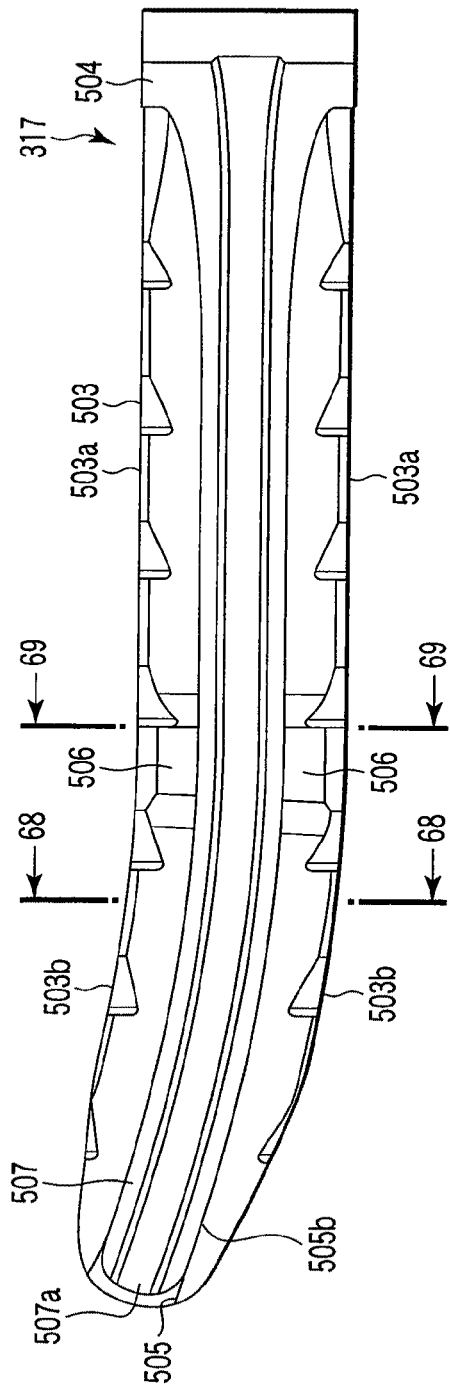
FIG. 67 is a plan view showing that surface of the jaw of the surgical operating apparatus according to the second embodiment, which is opposed to the probe distal end portion.

FIG. 67 shows that surface of the jaw 317, which is opposed to the probe distal end portion 303a. As shown in FIG. 67, the jaw 317 is formed in a substantially J-shaped curved form, which corresponds to the curved shape of the probe distal end portion 303a, in accordance with the curved shape of the probe distal end portion 303a of the probe unit 303. A therapeutic section 301A of the handpiece 301 is constituted by the jaw 317 and the probe distal end portion 303a.

The jaw 317 includes a metallic jaw body 501 (see FIG. 62) which is an electrically conductive member, and a hold member 502 which is attached to the jaw body 501. The hold member 502 is composed of an electrode member 503 (see FIG. 63) for high-frequency therapeutic treatment, and a pad member 504 (see FIG. 64) for ultrasonic therapeutic treatment. The electrode member 503 constitutes a second electrode section which is the other electrode of the bipolar electrodes. The pad member 504 is formed of an insulating material, for instance, a resin material such as polytetrafluoroethylene.

Figure 68:
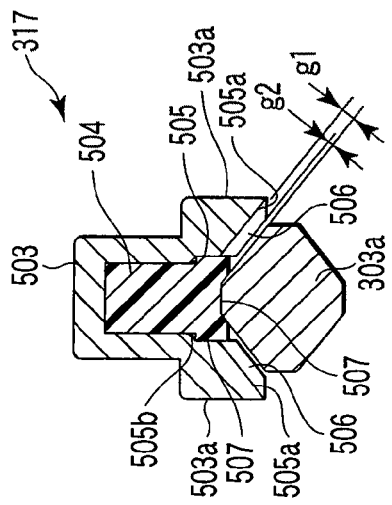
FIG. 68 is a transverse cross-sectional view taken along line 68-68 in FIG. 67, showing a closed state between the jaw and the probe of the surgical operating apparatus according to the second embodiment.

As shown in FIGS. 67 and 68, a groove portion 505, which is formed in accordance with the curved shape of the probe distal end portion 303a, is formed on the lower surface of the electrode member 503. The pad member 504 is inserted and mounted in the groove portion 505.

Inclined surfaces 505a, which are configured to gradually increase the groove width toward a lower-side opening surface, as shown in FIG. 68, are formed on both side wall surfaces of the groove portion 505. In addition, as shown in FIG. 67, tooth portions 503b for preventing a slip are formed on both side walls 503a of the groove portion 505 on the lower-side opening surface side. The tooth portions 503b form a slip-preventing section for preventing a slip of a clamped object between the probe distal end portion 303a and the jaw 317 when the jaw 317 and probe distal end portion 303a are engaged. A wall thickness T of the electrode member 503 is properly determined in consideration of the rigidity and coagulation performance.

Further, in the electrode member 503, a notch portion 505b is formed at a bottom portion of the inclined surface 505a of the groove portion 505. The notch portion 505b is formed in accordance with the curved shape of the probe distal end portion 303a. A push portion 507 of the pad member 504 is disposed at the notch portion 505b. The push portion 507 of the pad member 504 is a probe abutment member, on which the probe distal end portion 303a abuts, as shown in FIG. 68.

An alignment groove 507a is provided at a center of the push portion 507 of the pad member 504. As shown in FIG. 67, the alignment groove 507a is formed over the entire length of the pad member 504 from a front end portion to a rear end portion of the push portion 507. The probe distal end portion 303a is engaged in the alignment groove 507a. In the state in which the probe distal end portion 303a is engaged in the alignment groove 507a of the push portion 507, the probe distal end portion 303a is aligned and prevented from being displaced in the right-and-left direction (in FIG. 68) relative to the electrode member 503. Thereby, a clearance of a predetermined distance g1 is secured between the probe distal end portion 303a and the opposed inclined surface 505a of the electrode member 503, thus preventing contact between the inclined surfaces 505a of the electrode 503 and the probe distal end portion 303a.

The probe distal end portion 303a is formed to have a cross-sectional shape shown in FIG. 68. Specifically, left and right inclined surfaces 303a1, which are parallel to the left and right inclined surfaces 505a of the electrode member 503, are formed on the upper surface side of the probe distal end portion 303a. Left and right inclined surfaces 303a2, which are in opposite directions to the left and right inclined surfaces 303a1, are formed on the lower surface side of the probe distal end portion 303a. A flat surface portion 303a3, which is parallel to the alignment groove 507a of the push portion 507 of the pad member 504, is formed between the left and right inclined surfaces 303a1 on the upper surface side of the probe distal end portion 303a.

Figure 69:
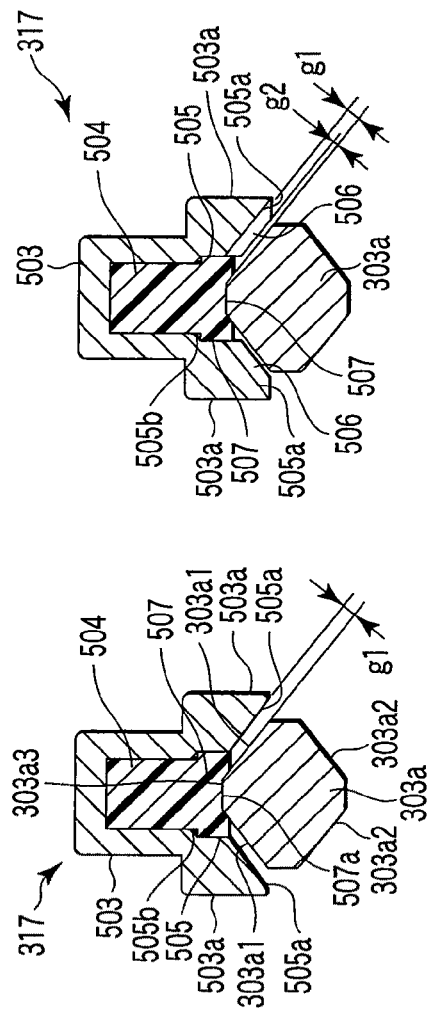
FIG. 69 is a transverse cross-sectional view of a spark point, taken along line 69-69 in FIG. 67, showing a closed state between the jaw and the probe of the surgical operating apparatus according to the second embodiment.

As shown in FIG. 69, projecting electrode portions 506 are formed on parts of the inclined surfaces 505a of the electrode member 503. The projecting electrode portions 506 project toward the opposed surfaces of the probe distal end portion 303a in the state in which the flat surface portion 303a3 at the upper surface of the probe distal end portion 303a is engaged in the alignment groove 507a of the push portion 507. Thereby, a gap g2 between the projecting electrode portion 506 and the probe distal end portion 303a is formed by a narrow width part, which is narrower than the distance g1 between those parts of the inclined surfaces 505a of the electrode member 503, which are other than the projecting electrode portions 506, and the probe distal end portion 303a. In short, the gap g2 of the narrow width part is formed to be g2<g1. The projecting electrode portions 506 are disposed at a position where the probe distal end portion 303a does not easily suffer a stress due to ultrasonic vibration when a living body tissue is clamped between the inclined surfaces 505a of the electrode member 503 and the probe distal end portion 303a.

Figure 63:
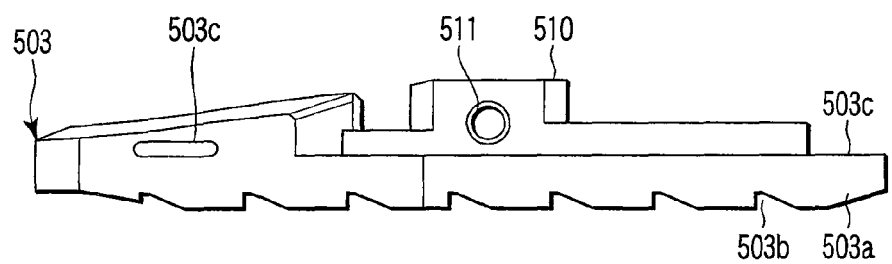
FIG. 63 is a side view showing an electrode member of the jaw of the surgical operating apparatus according to the second embodiment.
Figure 64:
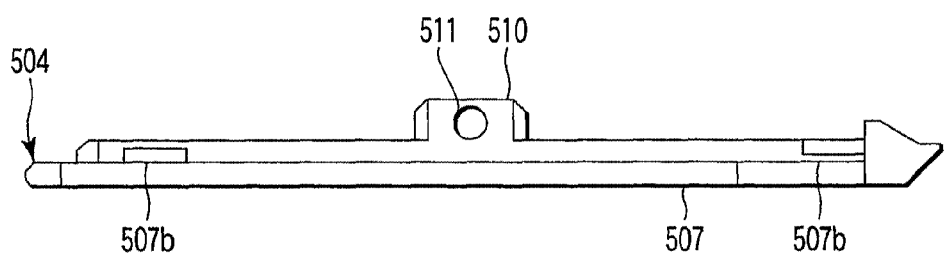
FIG. 64 is a side view showing a pad member of the jaw of the surgical operating apparatus according to the second embodiment.

As shown in FIG. 64, snap fit portions 507b are formed at a front end portion and a rear end portion of the push portion 507 of the pad member 504. As shown in FIG. 63, snap fit engaging portions 503c, which are disengageably engaged with the front and rear snap fit portions 507b of the pad member 504, are formed on the electrode member 503.

When the electrode member 503 and the pad member 504 are assembled, the snap fit portions 507b are engaged with the snap fit engaging portions 503c in the state in which the push portion 507 of the pad member 504 is inserted in the notch portion 505b of the groove portion 505 of the electrode member 503. Thereby, the electrode member 503 and the pad member 504 are integrally assembled and the hold member 502 is formed.

A projection portion 510 for attachment is projectingly provided on that side of the hold member 502, which is opposite to the surface thereof facing the probe distal end portion 303a. A screw insertion hole 511 is formed in the projection portion 510.

Figure 62:
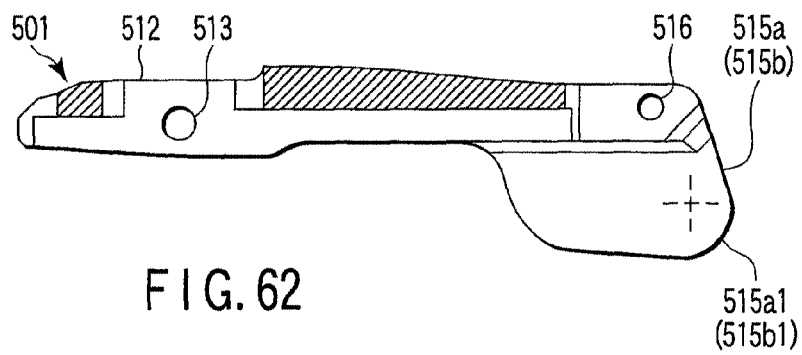
FIG. 62 is a side view showing a jaw body of a jaw of the surgical operating apparatus according to the second embodiment.

As shown in FIG. 62, a hold member engaging portion 512, which engages the projection portion 510 of the hold member 502, is provided on a distal end side of the jaw body 501. The projection portion 510 of the hold member 502 is engaged with the hold member engaging portion 512. Further, a screw hole 513 is formed in side wall portions of the hold member engaging portion 512. As shown in FIG. 65, when the hold member engaging portion 512 of the jaw body 501 and the projection portion 510 of the hold member 502 are engaged, a fixing screw 514, which is engaged in the screw hole 513 of the jaw body 501, is inserted in the screw insertion hole 511 of the hold member 502. In this state, the fixing screw 514 is fastened in the screw hole 513, and thereby the hold member 502 is attached to the jaw body 501. The electrode member 503 of the hold member 502 and the jaw body 501 are electrically connected via the fixing screw 514.

A proximal end portion of the jaw body 501 has two-forked arm portions 515a and 515b. The respective arm portions 515a and 515b have extension portions 515a1 and 515b1, which extend obliquely downward from the position of a center line of the jaw body 501. As shown in FIG. 66, the boss portions 327 are outwardly projectingly formed on outer surfaces of the extension portions 515a1 and 515b1. The boss portions 327 of the extension portions 515a1 and 515b1 are inserted and engaged in the circular holes 525a of the left and right projection portions 325 at the distal end portion of the outer sheath 318. Thereby, the jaw body 501 is rotatably attached by the boss portions 327 to the left and right projection portions 325 at the distal end portion of the outer sheath 318.

An operation pin insertion hole 516 is formed in a proximal portion of each of the two arm portions 515a and 515b. An operation pin 517 for coupling the jaw body 501 and the driving pipe 319 is inserted in the operation pin insertion holes 516. The jaw body 501 and the driving pipe 319 are electrically connected via the operation pin 517.

Thereby, the driving force of the driving pipe 319 is transmitted to the jaw 317 via the operation pin 517 by the advancing/retreating in the axial direction of the driving pipe 319. Accordingly, the jaw 317 is rotated about the boss portions 327. In this case, when the driving pipe 319 is pulled rearward, the jaw 317 is rotated about the boss portions 327 and driven (to an open position) in a direction away from the probe distal end portion 303a. Conversely, when the driving pipe 319 is pushed forward, the jaw 317 is rotated about the boss portions 327 and driven (to a closed position) in a direction toward the probe distal end portion 303a. A living body tissue is held between the jaw 317 and the probe distal end portion 303a of the probe unit 303 when the jaw 317 is rotated to the closed position.

The therapeutic section 301A of the handpiece 301 is constituted by the jaw 317 and the probe distal end portion 303a of the probe unit 303. The therapeutic section 301A is configured to selectively perform a plurality of therapeutic functions, for example, two therapeutic functions (a first therapeutic function and a second therapeutic function) in this embodiment. For instance, the first therapeutic function is set to be a function of simultaneously outputting an ultrasonic therapeutic output and a high-frequency therapeutic output. The second therapeutic function is set to be a function of outputting only the high-frequency therapeutic output.

The first therapeutic function and second therapeutic function of the therapeutic section 301A are not limited to the above-described configuration. For example, the first therapeutic function may be set to be a function of outputting an ultrasonic therapeutic output in a maximum output state, and the second therapeutic function may be set to be a function of outputting the ultrasonic therapeutic output in a preset arbitrary output state which is lower than the maximum output state.

As shown in FIGS. 59A to 59C and FIG. 60, the driving pipe 319 includes a tubular body section 521 and an operating section 522. The body section 521 is inserted in the outer sheath 318 so as to be slidable in the axial direction of the outer sheath 318. The operating section 522 is disposed on the distal end side of the body section 521, and includes a connection section 523 which is connected to the jaw 317.

Figure 59A:
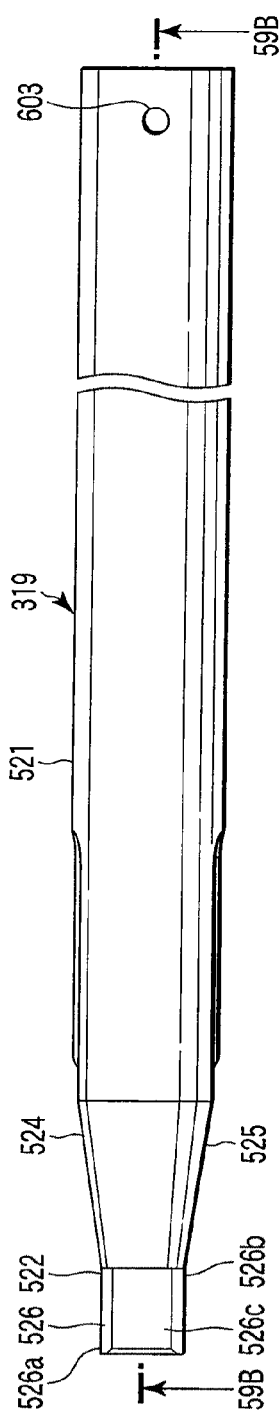
FIG. 59A is a plan view showing a driving pipe of the surgical operating apparatus according to the second embodiment.
Figure 59B:
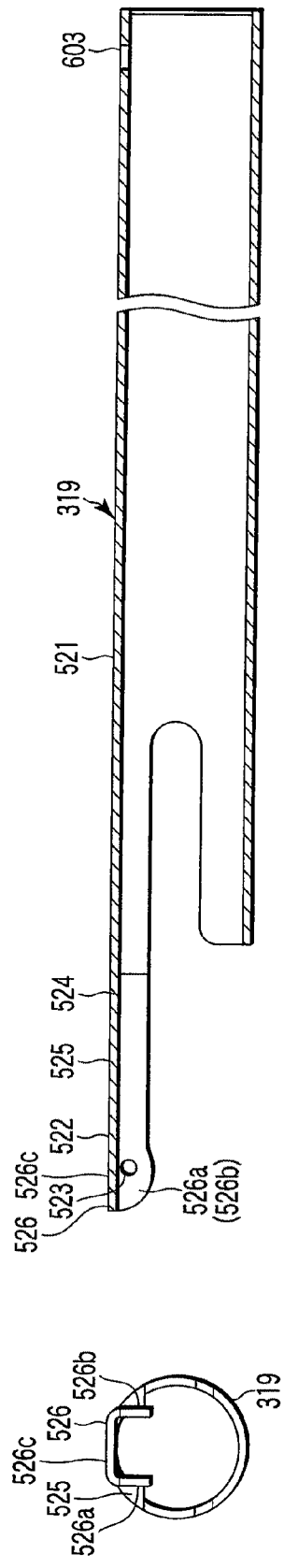
FIG. 59B is a cross-sectional view taken along line 59B-59B in FIG. 59A.
Figure 59C:
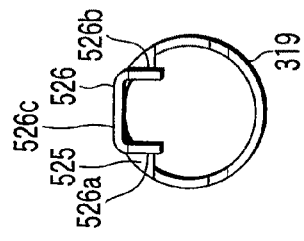
FIG. 59C is a front view showing the driving pipe shown in FIG. 59B.

The peripheral wall of a tubular distal end portion of the body section 521 includes a crescent-shaped arcuate cross-sectional portion 524, which is formed by leaving a substantially crescent-shaped arcuate cross-sectional portion over a predetermined length along the axial direction, and cutting out the other portion. As shown in FIG. 59A, the arcuate cross-sectional portion 524 includes a taper portion 525 with a tapered distal end side, which is processed to gradually taper toward the distal end side. As shown in FIG. 59C, a U-shaped portion 526 having a U-shaped cross section is formed at a distal end of the taper portion 525. The operating section 522 is constituted by the U-shaped portion 526.

As shown in FIG. 59C, the U-shaped portion 526 has two side surfaces 526a and 526b, which are opposed to each other, and a connecting surface 526c which connects the two side surfaces 526a and 526b. The connection section 523 is formed in each of the two side surfaces 526a and 526b of the U-shaped portion 526.

Figure 60:
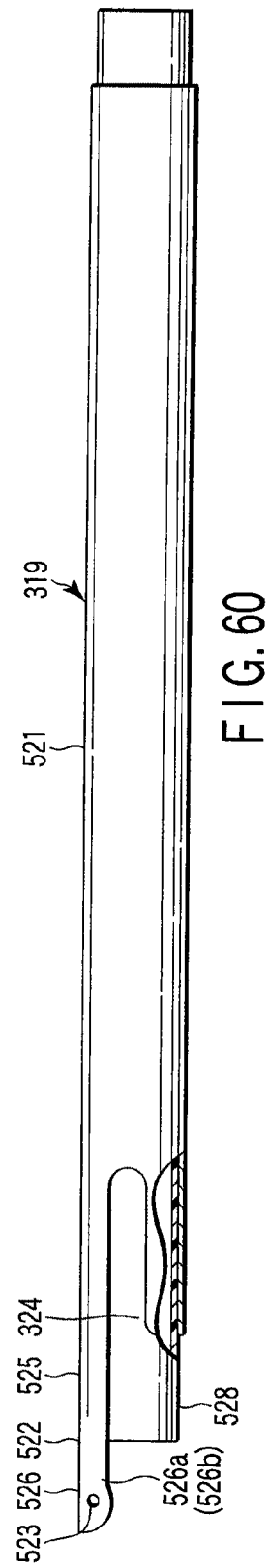
FIG. 60 is a side view showing, partly in cross section, an assembled state between the driving pipe and an insulation tube of the surgical operating apparatus according to the second embodiment.

As shown in FIG. 60, the insulation tube 324 includes a projection portion 528 which projects forward of the body section 521 of the driving pipe 319. The projection portion 528 extends up to a rear end position of the U-shaped portion 526.

Further, a proximal end portion of the insulation tube 324 extends to a proximal end side of the sheath body 316. The driving pipe 319 and probe unit 303 are electrically insulated by the insulation tube 324.

Figure 70:
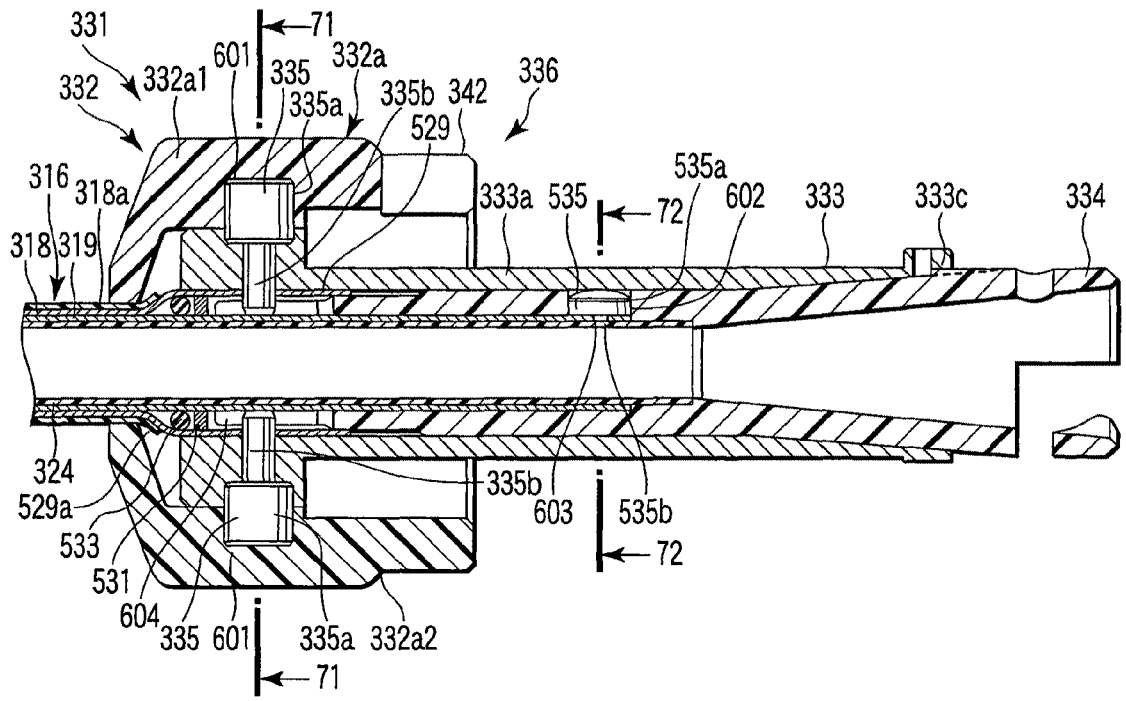
FIG. 70 is a longitudinal cross-sectional view showing a proximal end portion of the sheath unit of the surgical operating apparatus according to the second embodiment.

FIG. 70 shows a proximal end portion of the sheath body 316. The proximal end portion of the outer sheath 318 includes a flare portion 529 which has a greater inside diameter than the other portion (see FIG. 61D). A proximal end portion of the driving pipe 319 extends more rearward than the flare portion 529 of the outer sheath 318.

In addition, the proximal end portion of the sheath body 316 is provided with an attachment/detachment mechanism section 331 for attachment/detachment to/from the handle unit 304. The attachment/detachment mechanism section 331 includes a circular cylindrical large-diameter knob member 332, a guide cylindrical body (first tubular member) 333 which is formed of a metallic circular cylindrical body, and a circular cylindrical connection tube body (second tubular member) 334 which is formed of a resin material.

Figure 71:
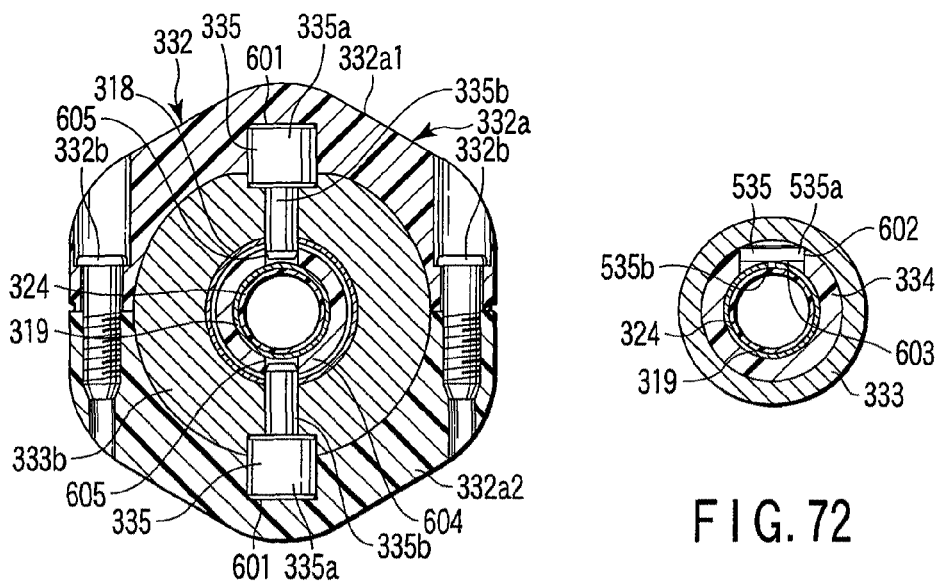
FIG. 71 is a cross-sectional view taken along line 71-71 in FIG. 70.
Figure 72:
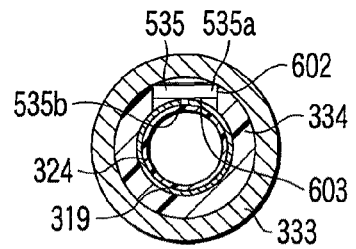
FIG. 72 is a cross-sectional view taken along line 72-72 in FIG. 70.

As shown in FIG. 71, the knob member 332 includes an annular knob body 332a. As shown in FIG. 72, the knob body 332a includes two C-shaped members 332a1 and 332a2 each having a substantially C shape. The two C-shaped members 332a1 and 332a2 are formed of a resin material, and the annular knob body 332a is formed in the state to which both end portions of the two C-shaped members 332a1 and 332a2 are coupled. The two C-shaped members 332a1 and 332a2 are coupled by two fixing screws 332b.

As shown in FIG. 73, engaging holes 601 are formed in inner peripheral surfaces of the two C-shaped members 332a1 and 332a2. Head portions 335a of pins 335, which restrict movement of internal parts, are engaged in the engaging holes 601. Thereby, the positions of the pins 335 can be restricted.

The guide cylinder 333 includes a tubular body 333a which is fitted over the flare portion 529 of the proximal end portion of the outer sheath 318 and extends rearwards. The distal end portion of the tubular body 333a is provided with a large-diameter portion 333b which has a greater outside diameter than the other portion. The knob member 332 is fitted on the large-diameter portion 333b. A connection flange portion 333c, which projects outward, is formed on the outer peripheral surface of a rear end portion of the guide cylinder 333.

Two pin insertion holes 333b1, which extend in the radial direction, are formed in the large-diameter portion 333b of the tubular body 333a. Shaft portion 335b of the pins 335 is inserted in the two pin insertion holes 333b1.

Two pin insertion holes are similarly formed in the flare portion 529 of the outer sheath 318 at positions corresponding to the two pin insertion holes 333b1 of the tubular body 333a. Shaft portions 335b of the pins 335 project inward through the two pin insertion holes 333b1 of the tuber body 333a and the two pin insertion holes of the outer sheath 318. Thereby, the knob member 332, the guide cylinder 333 and the flare portion 529 of the outer sheath 318 are integrally assembled by the pins 335 in the state in which the movement of the outer sheath 318 in the axial direction of the outer sheath 318 and the rotation thereof about the axis of the outer sheath 318 are restricted.

The connection tube body 334 is engaged in the guide cylinder 333 so as to be slidable in the axial direction of the outer sheath 318. The proximal end portion of the driving pipe 319 is inserted and fitted in the inner peripheral surface of the distal end portion of the connection tube body 334.

As shown in FIG. 70, a rotation restriction pin 535 is fixed on the proximal end portion of the driving pipe 319. As shown in FIG. 72, the rotation restriction pin 535 includes a large-diameter head portion 535a and a small-diameter shaft portion 535b. An engaging hole portion 602 for engagement with the head portion 535a of the rotation restriction pin 535 is formed in the connection tube body 334. A pin engaging hole 603 for engagement with the shaft portion 535b of the rotation restriction pin 535 is formed in the proximal end portion of the driving pipe 319. The driving pipe 319 and the connection tube body 334 are coupled via the rotation restriction pin 535. At this time, the driving pipe 319 and the connection tube body 334 are integrally assembled in the state in which the movement of the driving pipe 319 and the connection tube body 334 in the axial direction of the driving pipe 319 and the rotation of thereof about the axis of the driving pipe 319 are restricted by the rotation restriction pin 535.

The distal end portion of the connection tube body 334 is inserted into the inside of the flare portion 529 of the outer sheath 318 and extends to the vicinity of a stepped portion 529a between the outer sheath 318 and the flare portion 529.

Seal means 530 for effecting sealing between the outer sheath 318 and the driving pipe 319 is provided between the flare portion 529 and the driving pipe 319. The seal means 530 includes one backup ring 531 and one ring 533. The O ring 533 is provided between the stepped portion 529a of the flare portion 529 and the backup ring 531 so as to be movable in the axial direction of the outer sheath 318. The position of the backup ring 531 of the O ring 533 is restricted at the distal end portion of the connection tube body 334. Further, the shape of the stepped portion 529a of the flare portion 529 is so used as to function as a front-side backup ring of the O ring 533. Thereby, only one backup ring 531 may be provided as the backup ring of the O ring 533.

The distal end portion of the connection tube body 334 has two slits 605 which extend along the axis of the driving pipe 319. Inner end portions of the shaft portions 335b of the pins 335 are inserted and engaged in the slits 605. Thereby, the movement in the rotational direction of the three parts, namely, the guide cylinder 333, outer sheath 318 and connection tube body 334, relative to the knob member 332, can be restricted by the pin 335.

An attachment/detachment section 336 for attachment/detachment to/from the handle unit 304 is disposed at the rear end portion of the knob member 332. The attachment/detachment section 336 of the knob member 332 has a guide groove (not shown) with an inclined surface, and an engaging recess portion 342. The guide groove is provided extending in a circumferential direction on the outer peripheral surface of the proximal end portion of the knob member 332. In addition, the guide groove has a tapered inclined surface with an outside diameter gradually decreasing toward the rear end portion side of the knob member 332.

The engaging recess portion 342 is formed at one end portion of the guide groove. The engaging recess portion 342 is formed of a recess portion having a smaller diameter than the inclined surface of the guide groove. The engaging recess portion 342 is configured such that an engaging lever 343 (to be described later) on the handle unit 304 side is disengageably engaged in the engaging recess portion 342.

Figure 55:
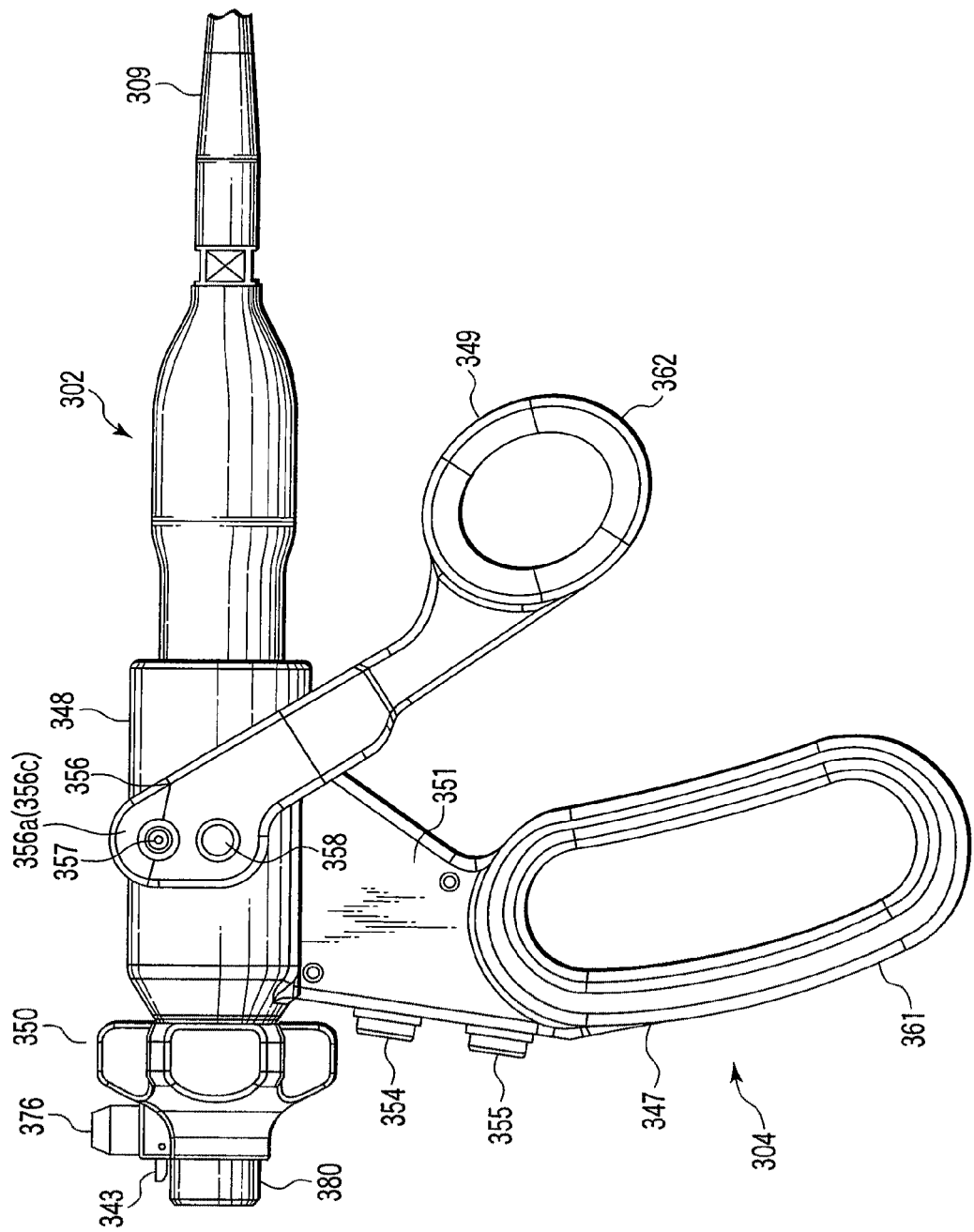
FIG. 55 is a side view showing a coupled state between a handle unit and a transducer unit of the surgical operating apparatus according to the second embodiment.

As shown in FIG. 55, the handle unit 304 mainly includes a stationary handle 347, a hold cylinder 348, a movable handle 349 and a rotational operation knob 350. The hold cylinder 348 is provided on the upper part of the stationary handle 347. A switch hold section 351 is provided between the stationary handle 347 and the hold cylinder 348.

As shown in FIG. 55, the switch hold section 351 has a switch attachment surface on a front side thereof, to which a plurality of hand switches, for example, two hand switches (first switch 354 and second switch 355) in the present embodiment, are attached. The first switch 354 and second switch 355 are switches for selecting therapeutic functions of the therapeutic section 301A of the handpiece 301.

In the switch hold section 351, the first switch 354 and second switch 355 are arranged in the up-and-down direction. The first switch 354 is disposed on an upper side of the switch hold section 351, and is set to be a switch which selects a first therapeutic function that is frequently used among the plural therapeutic functions. The second switch 355 is disposed on a lower side of the switch hold section 351, and is set to be a switch which selects another second therapeutic function of the plural therapeutic functions. For example, the first switch 354 is set to be a switch button for incision, and the second switch 355 is set to be a switch button for coagulation.

As shown in FIG. 54, the movable handle 349 has a substantially U-shaped arm section 356 at an upper part thereof. The U-shaped arm section 356 includes two arms 356a and 356b. The movable handle 349 is assembled to the hold cylinder 348 in the state in which the hold cylinder 348 is inserted between the two arms 356a and 356b.

Each of the arms 356a and 356b has a support pin 357 and an operation pin 358. A pin receiving hole portion (not shown) and a window portion (not shown) are formed in each of both side portions of the hold cylinder 348. The support pin 357 of each arm 356a, 356b is inserted in the pin receiving hole portion of the hold cylinder 348. Thereby, an upper end portion of the movable handle 349 is rotatably supported on the hold cylinder 348 via the support pins 357.

Ring-shaped finger hook portions 361 and 362 are provided on lower end portions of the stationary handle 347 and movable handle 349, respectively. By hooking the fingers on the finger hook portions 361 and 362 and holding them, the movable handle 349 rotates via the support pins 357 and the movable handle 349 is opened/closed relative to the stationary handle 347.

The operation pins 358 of the movable handle 349 extend into the hold cylinder 348 through the window portions of the hold cylinder 348. An operation force transmission mechanism (not shown), which transmits an operation force of the movable handle 349 to the driving pipe 319 of the jaw 317, is provided inside the hold cylinder 348.

If the movable handle 349 is held and the movable handle 349 is closed relative to the stationary handle 347, the operation pins 358 rotate about the support pins 357 in accordance with the rotational operation of the movable handle 349 at this time. A slider member (not shown) of the operation force transmission mechanism, which is in interlock with the rotation of the support pins 357, moves forward in the axial direction. At this time, the operation force of the movable handle 349 is transmitted to the connection tube body 334 of the sheath unit 305 via the operation force transmission mechanism, and the driving pipe 319 of the jaw 317 moves forward. Thereby, the jaw body 501 of the jaw 317 rotates via the boss portions 327.

Further, when a living body tissue is clamped between the hold member 502 of the jaw 317 and the probe distal end portion 303a of the probe unit 303 by this operation, the hold member 502 rotates over a certain angle about the fixing screw 514 in accordance with the bending of the probe distal end portion 303a so that force uniformly acts over the entire length of the hold member 502. In this state, ultrasonic is output and a living body tissue, such as a blood vessel, can be coagulated or incised.

The rotational operation knob 350 is fitted and fixed on the front end portion of the hold cylinder 348. The engaging lever 343 and an operation button 376 for operating the engaging lever 343 in such a direction as to release engagement of the engaging lever 343 are provided at the front end portion of the rotational operation knob 350.

Next, the operation of the present embodiment is described. The handpiece 301 of the ultrasonic operating apparatus of the present embodiment, as shown in FIG. 54, comprises four units, namely, the transducer unit 302, probe unit 303, handle unit 304 and sheath unit 305, which are detachable. When the handpiece 301 is used, the transducer unit 302 and the probe unit 303 are coupled. Thereby, the first high-frequency electric path 313, which transmits a high-frequency current to the coupled body of the transducer unit 302 and probe unit 303, is formed.

Subsequently, the handle unit 304 and the sheath unit 305 are coupled. When the handle unit 304 and sheath unit 305 are coupled, the connection tube body 334 is inserted in the hold cylinder 348 of the handle unit 304 in the state in which the knob member 332 of the sheath unit 305 is held. After this insertion operation, the knob member 332 of the sheath unit 305 is rotated about the axis, relative to the handle unit 304. By this operation, the engaging lever 343 on the handle unit 304 side is inserted and engaged in the engaging recess portion 342 of the knob member 332. Thereby, the sheath-unit-side electric path (not shown) and the handle-unit-side electric path are electrically connected. As a result, the second high-frequency electric path, which transmits a high-frequency current, is formed in the coupled body of the sheath unit 305 and handle unit 304.

When the sheath unit 305 is rotated about the axis thereof, the operation force on the handle unit 304 side at the time when the movable handle 349 is closed relative to the stationary handle 347 can be transmitted, at the same time, to the driving pipe 319 of the jaw 317 on the sheath unit 305 side. This state is the coupled state between the sheath unit 305 and the handle unit 304.

Thereafter, the coupled body of the sheath unit 305 and handle unit 304 and the coupled body of the ultrasonic transducer 306 and probe unit 303 are assembled as one body. In this assembling work, the second high-frequency electric path of the coupled body of the sheath unit 305 and handle unit 304 is connected to the wiring line for high-frequency power within the cable 309.

When the handpiece 301 is used, the movable handle 349 is opened/closed relative to the stationary handle 347. The driving pipe 319 is axially moved in interlock with the operation of the movable handle 349, and the jaw 317 is opened/closed, relative to the probe distal end portion 303*a* of the probe unit 303, in interlock with the advancing/retreating movement of the driving pipe 319 in its axial direction.

When the movable handle 349 is closed relative to the stationary handle 347, the driving pipe 319 is pushed forward in interlock with the operation of the movable handle 349. The jaw 317 is rotated and driven (to a closed position) in a direction toward the probe distal end portion 303*a* of the probe unit 303 in interlock with the pushing operation of the driving pipe 319. By the rotation of the jaw 317 to its closed position, a living body tissue is held between the jaw 317 and the probe distal end portion 303*a* of the probe unit 303.

In this state, one of the switch button 54 for incision and the switch button 55 for coagulation, which are provided on the stationary handle 347, is selectively pressed. When the switch button 55 for coagulation is pressed, power is supplied to the first high-frequency electric path 313 for supplying a high-frequency current to the probe distal end portion 303*a* of the probe unit 303 and to the second high-frequency electric path for supplying a high-frequency current to the jaw body 28 of the sheath unit 305. Thereby, the two bipolar electrodes for high-frequency therapeutic treatment are constituted by the probe distal end portion 303*a* of the probe unit 303 and the jaw body 28 of the sheath unit 305. By supplying a high-frequency current between the two bipolar electrodes which are constituted by the probe distal end portion 303*a* of the probe unit 303 and the jaw body 28 of the sheath unit 305, bipolar high-frequency therapeutic treatment can be performed on the living body tissue between the jaw 317 and the probe distal end portion 303*a* of the probe unit 303.

When the switch button 54 for incision is pressed, a driving current is supplied to the ultrasonic transducer 306 at the same time as the supply of high-frequency current, and the ultrasonic transducer 306 is driven. At this time, ultrasonic vibration from the ultrasonic transducer 306 is transmitted to the probe distal end portion 303*a* via the vibration transmission member 311. Thereby, incision, resection, etc. of the living body tissue can be performed by making use of ultrasonic wave at the same time as the supply of high-frequency current. In the meantime, coagulation for the living body tissue can be performed by using ultrasonic wave.

When the movable handle 349 is opened relative to the stationary handle 347, the driving pipe 319 is pulled to the proximal side in interlock with the opening operation of the movable handle 349. The jaw 317 is driven (to an open position) in a direction away from the probe distal end portion 303*a* of the probe unit 303 in interlock with the pulling operation of the driving pipe 319.

When the rotational operation knob 350 is rotated, the assembly unit within the hold cylinder 348 is rotated together with the rotational operation knob 350 as one body about the axis thereof. Further, the rotational operation force of the rotational operation knob 350 is transmitted to the vibration transmission member 311 of the probe unit 303. Thereby, the assembly unit within the hold cylinder 348 and the coupled body of the transducer unit 302 and probe unit 303 are rotated about the axis as one body.

At this time, the knob member 332 and guide cylindrical body 333 of the sheath unit 305 rotate together with the rotational operation knob 350. Furthermore, the outer sheath 318 rotates together with the guide cylindrical body 333, and the rotation of the guide cylindrical body 333 is transmitted to the connection tube body 334 and driving pipe 319 via the rotation restriction pin 535. Thus, the jaw 317 and probe distal end portion 303*a* of the therapeutic section 301A are rotated about the axis at the same time together with the rotational operation knob 350.

The following advantageous effects can be obtained with the above-described structure. Specifically, in the handpiece 301 of the ultrasonic operating apparatus of the present embodiment, the projecting electrode portions 506 are formed on the electrode member 503 of the jaw 317 of the therapeutic section 301A. The projecting electrode portions 506 project from the inclined surfaces 505*a* of the electrode member 503 toward the opposed surfaces of the probe distal end portion 303*a* in the state in which the probe distal end portion 303*a* is engaged in the alignment groove 507*a* of the push portion 507. Thereby, the gap g2 between the projecting electrode portion 506 and the probe distal end portion 303*a* is formed by the narrow width part, which is narrower than the distance g1 between those parts of the inclined surfaces 505*a* of the electrode member 503, which are other than the projecting electrode portions 506, and the probe distal end portion 303*a*. The projecting electrode portions 506 are formed at a position where the probe distal end portion 303*a* does not easily suffer a stress when a living body tissue is clamped between the inclined surfaces 505*a* of the electrode member 503 and the probe distal end portion 303*a*. For example, the projecting electrode portions 506 are disposed at a position, such as a distal end side position of the probe distal end portion 303*a*, which is away from a proximal end side position of the curved shape (indicated by the arrow P in FIG. 69) where a stress due to ultrasonic vibration tends to concentrate.

Thus, when the pad member 504 is worn due to ultrasonic therapeutic treatment, the parts of the projecting electrode portions 506 can be first put in contact with the probe distal end portion 303*a*, and a spark can be occurred. As a result, the position of occurrence of a spark (the position where a crack occurs in the probe distal end portion 303*a*) can be controlled. Thereby, it becomes possible to surely prevent the occurrence of a spark at the proximal end side position of the curved shape (indicated by the arrow P in FIG. 69) where a stress due to ultrasonic vibration tends to concentrate. Therefore, a crack does not easily occur in the probe distal end portion 303*a*, and the durability can be improved. Moreover, in case a crack occurs in the probe distal end portion 303*a*, the crack can exactly be detected by the probe breakage detection section of the apparatus body.

The probe breakage detection section of the apparatus body is constituted as follows. Specifically, the probe breakage detection section detects the frequency of ultrasonic vibration. In general, the frequency of the probe+transducer is designed at a predetermined preset value, e.g. 47±1 kHz. As long as the frequency of ultrasonic vibration, which is detected by the probe breakage detection section, falls within the above range, ultrasonic vibration can be output. However, if a crack occurs in the probe, the frequency increases (the wavelength decreases), and the frequency falls out of the above range. Consequently, the body stops the output. However, if a crack occurs at a distal end side position of the curved shape of the probe distal end portion, the degree of increase of the frequency of ultrasonic vibration is small, and it becomes difficult for the probe breakage detection section to detect the broken state of the probe. In the present embodiment, as described above, the position where a spark occurs (the position where a crack occurs in the probe distal end portion 303a) can be controlled. Therefore, it is possible to surely prevent the occurrence of a spark at the distal end side position of the curved shape of the probe distal end portion. As a result, the safety can be ensured.

Besides, in the present embodiment, the alignment groove 507a is provided at a center of the push portion 507 of the pad member 504. Thus, the probe distal end portion 303a is engaged and fitted in the alignment groove 507a. By engaging the probe distal end portion 303a in the alignment groove 507a of the push portion 507, the probe distal end portion 303a can be prevented from being displaced in the right-and-left direction (in FIG. 68) relative to the electrode member 503. As a result, the clearance between the electrode member 503 and the probe distal end portion 303a can be exactly controlled.

Further, in the present embodiment, the boss portions 327 are outwardly projectingly formed on the arm portions 515a and 515b at the proximal end portion of the jaw body 501. The boss portions 327 are inserted and engaged in the circular holes 525a of the left and right projection portions 325 at the distal end portion of the outer sheath 318. Thereby, the jaw body 501 is rotatably attached by the boss portions 327 to the left and right projection portions 325 at the distal end portion of the outer sheath 318. Therefore, the number of parts can be reduced, compared to the case in which the proximal end portion of the jaw body 501 is connected to the distal end portion of the outer sheath 318 by separate parts such as pins. Thereby, the work of assembly between the jaw body 501 and the distal end portion of the outer sheath 318 can be facilitated.

In the present embodiment, as shown in FIG. 64, the snap fit portions 507b are formed at the front end portion and the rear end portion of the push portion 507 of the pad member 504. As shown in FIG. 63, the snap fit engaging portions 503c are formed on the electrode member 503. When the electrode member 503 and the pad member 504 are assembled, the snap fit portions 507b are engaged with the snap fit engaging portions 503c. Thereby, the electrode member 503 and the pad member 504 are integrally assembled. Therefore, the work of assembly between the electrode member 503 and the pad member 504 can be made easier than in the prior art.

In the present embodiment, as shown in FIG. 72, in the knob member 332 at the proximal end portion of the sheath body 316, the two C-shaped members 332a1 and 332a2 each having a substantially C shape are coupled by the two fixing screws 332b, and thus the annular knob body 332a is formed as shown in FIG. 71. Further, the engaging holes 601 are formed in inner peripheral surfaces of the two C-shaped members 332a1 and 332a2. The head portions 335a of the pins 335, which restrict movement of internal parts, are engaged in the engaging holes 601. Thereby, the positions of the pins 335 can be restricted. Therefore, the number of internal parts assembled in the knob member 332 can be made less than in the prior art, and the assembly can be made easier.

In the present embodiment, since the position of the backup ring 531 of the O ring 533 is restricted at the distal end portion of the connection tube body 334, there is no need to provide other parts for restricting the position of the backup ring 531. Therefore, the number of parts can be reduced and the assembly can be made easier.

In the present embodiment, the movement of the three parts, namely, the knob member 332, the guide cylinder 333 and the flare portion 529 of the outer sheath 318 in the axial direction of the outer sheath 318 and the movement thereof about the axis of the outer sheath 318 are restricted by the pins 335. Thereby, compared to the prior art, the number of parts can be reduced and the assembly can be made easier.

In the present embodiment, the stepped portion 529a between the outer sheath 318 and the flare portion 529 can be made to serve also as a front-side backup ring of the O ring 533. Thus, it should suffice to provide only one backup ring 531 on the rear side of the O ring 533. Thereby, compared to the case in which backup rings are provided in front of and behind the O ring 533, the number of parts can be reduced and the assembly can be made easier.

In the present embodiment, the diameter of the head portion 535a of the rotation restriction pin 535, which couples between the driving pipe 319 and connection tube body 334 and restricts the axial movement of the driving pipe 319 and the rotation of the driving pipe 319 about its axis, is increased. Thereby, swinging of the head portion 535a of the rotation restriction pin 535 can be prevented.

Further, in the present embodiment, the notch portion 592 for smoothing the movement of the driving pipe 319 is formed on the upper side (in FIG. 61B) of the distal end portion of the outer sheath 318. When the jaw 317 is rotated, the coupling portion between the connection section 523 of the U-shaped portion 526 of the driving pipe 319 and the operation pin 517 of the jaw 317 makes arcuate movement. Consequently, the U-shaped portion 526 of the driving pipe 319 moves up and down. At this time, when the U-shaped portion 526 of the driving pipe 319 moves upward, the notch portion 592 at the distal end portion of the outer sheath 318 can prevent contact between the outer sheath 318 and the driving pipe 319. Therefore, when the U-shaped portion 526 of the driving pipe 319 moves upward, it is possible to prevent occurrence of frictional force due to contact between the outer sheath 318 and the driving pipe 319, which leads to non-smooth sliding movement. As a result, the rotational operation of the jaw 317 can smoothly be performed.

In the present embodiment, there is no need to form a slit in the U-shaped portion 526 of the driving pipe 319. Accordingly, a decrease in strength of the U-shaped portion 526 of the driving pipe 319 can be prevented.

In the present embodiment, as shown in FIG. 65, the notch portion 592 of the outer sheath 318 is covered with the outer coating 318a which is formed of an insulating material. Thus, it is possible to prevent the notch portion 592 of the outer sheath 318 from being caught by, for instance, a trocar.

Needless to say, the present invention is not limited to the above-described embodiments, and various modifications may be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical operating apparatus comprising:
a sheath having a distal end and a proximal end;
a rod-shaped probe main body configured to be inserted into the sheath and having a distal end and a proximal end, and which is configured to transmit ultrasonic vibration;
a jaw pivoted to the distal end of the sheath;

a probe distal end which is provided at the distal end of the probe main body and meshes with the jaw; and a driving member including a tubular main body portion configured to be inserted into the sheath slidably along an axial direction of the sheath and an acting portion which is provided at a distal end of the main body portion and has a connection portion connected to the jaw, the connection portion positioned and configured to rotate the jaw according to a sliding action of the main body portion, wherein the sheath includes a notched portion positioned and configured to prevent the sheath from contacting a proximal portion of the jaw member when the connection portion of the driving member with the jaw moves in a direction perpendicular to a sliding direction of the driving member at a rotation time of the jaw, wherein the acting portion comprises a tapered shape portion gradually and gently narrowed toward a distal end of a tubular body of the main body portion;

the tapered shape portion comprises a U-shaped extension portion with U-shaped in sectional configuration at the distal end of the tubular body of the main body portion;

the U-shaped extension portion has two side faces disposed so as to be opposed to each other and a connected face connecting the two side faces;

the connected face includes an inclined face where a distance between the two side faces is gradually tapered toward a distal end of the connected face; and the connection portion is formed on each of the two side faces disposed at distal ends of the connected face.

2. The surgical operating apparatus according to claim 1, wherein the notched portion is formed on a peripheral wall face of the distal end of the sheath corresponding to a moving direction of the jaw at the moving time of the jaw in an opening operation direction of the jaw.

3. The surgical operating apparatus according to claim 1, wherein the sheath comprising an outer skin covering the sheath, the outer skin formed from insulating material, and the notched portion is covered with the outer skin.

* * * * *